United States Patent
Kassab et al.

(10) Patent No.: US 11,103,375 B2
(45) Date of Patent: *Aug. 31, 2021

(54) DEVICES AND SYSTEMS CONFIGURED TO FIT AROUND A TISSUE OR ORGAN AND METHODS OF THE SAME

(71) Applicant: CVDevices, LLC, San Diego, CA (US)

(72) Inventors: Ghassan S. Kassab, La Jolla, CA (US); Thomas A. Kramer, San Carlos, CA (US)

(73) Assignee: CVDevices, LLC, San Diego, CA (US)

( * ) Notice: Subject to any disclaimer, the term of this patent is extended or adjusted under 35 U.S.C. 154(b) by 486 days.

This patent is subject to a terminal disclaimer.

(21) Appl. No.: 15/991,226

(22) Filed: May 29, 2018

(65) Prior Publication Data

US 2018/0271686 A1    Sep. 27, 2018

Related U.S. Application Data

(63) Continuation of application No. 14/215,829, filed on Mar. 17, 2014, now Pat. No. 9,980,841, which is a
(Continued)

(51) Int. Cl.
*A61F 5/00*      (2006.01)
*A61B 17/122*   (2006.01)

(52) U.S. Cl.
CPC .......... *A61F 5/0086* (2013.01); *A61B 17/122* (2013.01); *A61F 5/0013* (2013.01); *A61B 17/1227* (2013.01)

(58) Field of Classification Search
CPC ..... A61B 17/122; A61B 17/12; A61B 17/132; A61B 17/1322; A61B 17/1325;
(Continued)

(56) References Cited

U.S. PATENT DOCUMENTS 3,149,390 A   9/1964 McCoy
3,326,217 A   6/1967 Sydney
(Continued)

FOREIGN PATENT DOCUMENTS

WO   WO 2006/111961   11/2006
WO   WO 2003/147582   12/2008
WO   WO 2011/025778   3/2011

OTHER PUBLICATIONS

International Searching Authority, International Search Report, dated Oct. 20, 2010 (PCT/US2010/046479).
(Continued)

*Primary Examiner* — Dianne Dornbusch
(74) *Attorney, Agent, or Firm* — Reichel Stohry Dean LLP; Mark C. Reichel; Natalie J. Dean

(57) ABSTRACT

Devices and systems to fit around a tissue or organ and methods of using the same. In at least one embodiment of an implantable device of the present disclosure, the implantable device comprises a first engaging component comprising a first rigid inner plate at least partially surrounded by a first flexible coating, a second engaging component comprising a second rigid inner plate at least partially surrounded by a coating selected from the group consisting of the first flexible coating and the second flexible coating, a first c-ring and a second c-ring coupled to the engaging components, and a cover flap coupled to either the first engaging component or the second engaging component and capable of either further coupling to the second engaging component when initially coupled to the first engaging component or further coupling to the first engaging component when initially coupled to the second engaging component.

20 Claims, 37 Drawing Sheets

Related U.S. Application Data continuation-in-part of application No. 13/080,586, filed on Apr. 5, 2011, now Pat. No. 8,979,876, which is a continuation-in-part of application No. 12/861,251, filed on Aug. 23, 2010, now Pat. No. 9,089,391, which is a continuation-in-part of application No. 12/546,139, filed on Aug. 24, 2009, now Pat. No. 9,402,757.

(60) Provisional application No. 61/800,687, filed on Mar. 15, 2013.

(58) Field of Classification Search
CPC . A61B 17/1327; A61B 17/1227; A61B 17/02; A61B 17/0206; A61B 2017/12004; A61F 5/0083; A61F 5/0086; A61F 5/0053; A61F 5/0063; A61F 5/0066; A61F 2/0054
See application file for complete search history.

(56) References Cited

U.S. PATENT DOCUMENTS

| | | |
|---|---|---|
| 3,916,908 A | 11/1975 | Leveen |
| 4,390,019 A | 6/1983 | LeVeen |
| 4,458,681 A | 7/1984 | Hopkins |
| 4,681,109 A | 7/1987 | Arroyo |
| 4,821,720 A | 4/1989 | Hajduch |
| 4,827,930 A | 5/1989 | Kees, Jr. |
| 4,924,864 A | 5/1990 | Danzig |
| 4,943,298 A | 7/1990 | Fujita |
| 4,944,741 A | 7/1990 | Hasson |
| 4,961,743 A | 10/1990 | Kees et al. |
| 5,057,118 A | 10/1991 | Picha |
| 5,217,473 A | 6/1993 | Yoon |
| 5,242,456 A | 9/1993 | Nash et al. |
| 5,411,481 A | 5/1995 | Allen et al. |
| 5,415,666 A | 5/1995 | Gourlay et al. |
| 5,487,746 A | 1/1996 | Yu et al. |
| 5,549,621 A | 8/1996 | Bessler et al. |
| 5,569,274 A | 10/1996 | Rapacki et al. |
| 5,776,147 A | 7/1998 | Dolendo |
| 5,921,996 A | 7/1999 | Sherman |
| 5,984,934 A | 11/1999 | Ashby et al. |
| 6,077,241 A | 6/2000 | Fareed |
| 6,159,217 A | 12/2000 | Robie et al. |
| 6,193,732 B1 | 2/2001 | Frantzen et al. |
| 6,206,897 B1 | 3/2001 | Jamiolkowski et al. |
| 6,440,145 B1 | 8/2002 | Assawah |
| 6,626,916 B1 | 9/2003 | Yeung et al. |
| 6,869,438 B2 | 3/2005 | Chao |
| 7,120,969 B2 | 10/2006 | Carls |
| 7,153,313 B2 | 12/2006 | Whitton |
| 7,288,100 B2 | 10/2007 | Trigueros |
| 7,488,334 B2 | 2/2009 | Jugenheimer et al. |
| 7,992,757 B2 | 8/2011 | Wheeler |
| 8,097,004 B2 | 1/2012 | Wild |
| 8,187,290 B2 | 5/2012 | Buchman |
| 2002/0068946 A1 | 6/2002 | Kortenbach et al. |
| 2003/0195558 A1 | 10/2003 | Curtis |
| 2003/0220678 A1 | 11/2003 | Tronnes et al. |
| 2004/0073241 A1 | 4/2004 | Barr |
| 2004/0147942 A1 | 7/2004 | Chao |
| 2004/0158286 A1 | 8/2004 | Roux et al. |
| 2004/0243152 A1 | 12/2004 | Taylor et al. |
| 2004/0267291 A1 | 12/2004 | Byrum et al. |
| 2005/0085835 A1 | 4/2005 | Rennich |
| 2005/0119674 A1 | 6/2005 | Gingras |
| 2005/0149068 A1 | 7/2005 | Williams et al. |
| 2005/0149069 A1 | 7/2005 | Bertolero et al. |
| 2005/0251183 A1 | 11/2005 | Buckman et al. |
| 2005/0256365 A1 | 11/2005 | Timm |
| 2005/0277959 A1 | 12/2005 | Cosgrove et al. |
| 2006/0009793 A1 | 1/2006 | Rennich |
| 2006/0020271 A1 | 1/2006 | Stewart et al. |
| 2006/0116679 A1 | 6/2006 | Lutz et al. |
| 2006/0130288 A1 | 6/2006 | Carls |
| 2006/0264699 A1 | 11/2006 | Gertner |
| 2006/0264981 A1 | 11/2006 | Viola |
| 2007/0021761 A1 | 1/2007 | Phillips |
| 2007/0032807 A1 | 2/2007 | Ortiz et al. |
| 2007/0213585 A1 | 9/2007 | Monassevitch |
| 2007/0213747 A1 | 9/2007 | Monassevitch et al. |
| 2008/0004637 A1 | 1/2008 | Klassen et al. |
| 2008/0033457 A1 | 2/2008 | Francischelli et al. |
| 2008/0132915 A1 | 6/2008 | Buckman et al. |
| 2008/0177292 A1 | 7/2008 | Jacobs |
| 2008/0208324 A1 | 8/2008 | Glithero et al. |
| 2008/0269788 A1 | 10/2008 | Greven |
| 2008/0275480 A1 | 11/2008 | Jacobs et al. |
| 2008/0275555 A1 | 11/2008 | Makower et al. |
| 2009/0012545 A1 | 1/2009 | Williamson et al. |
| 2009/0125038 A1 | 5/2009 | Ewers et al. |
| 2009/0157107 A1 | 6/2009 | Kierath |
| 2009/0292163 A1 | 11/2009 | Kassab |
| 2010/0174295 A1 | 7/2010 | Kassab et al. |
| 2011/0046641 A1 | 2/2011 | Kassab |
| 2011/0112559 A1 | 5/2011 | Monassevitch et al. |
| 2011/0178552 A1 | 7/2011 | Biscup et al. |
| 2012/0109161 A1 | 5/2012 | Privitera |
| 2012/0109164 A1 | 5/2012 | Kassab |

OTHER PUBLICATIONS

International Searching Authority, Written Opinion of the International Searching Authority, dated Oct. 20, 2010 (PCT/US2010/046479).

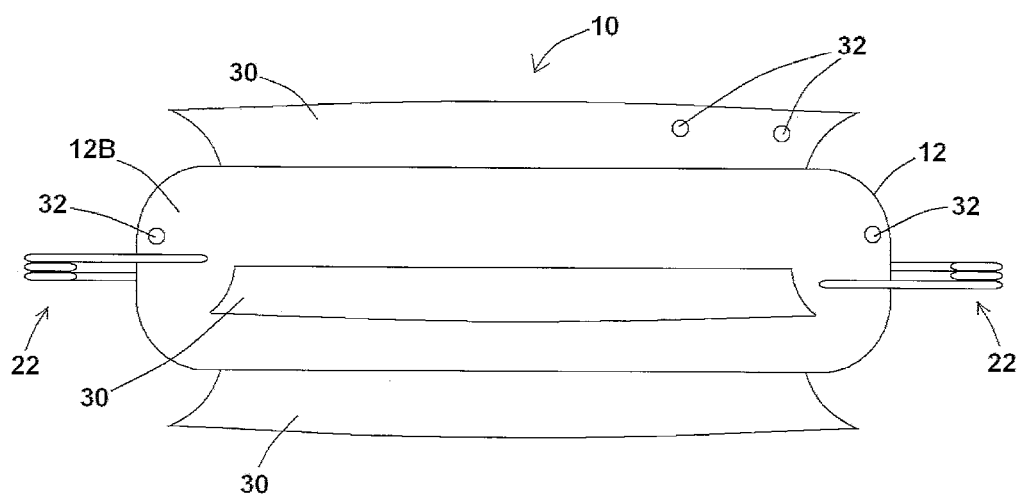
Fig. 3A
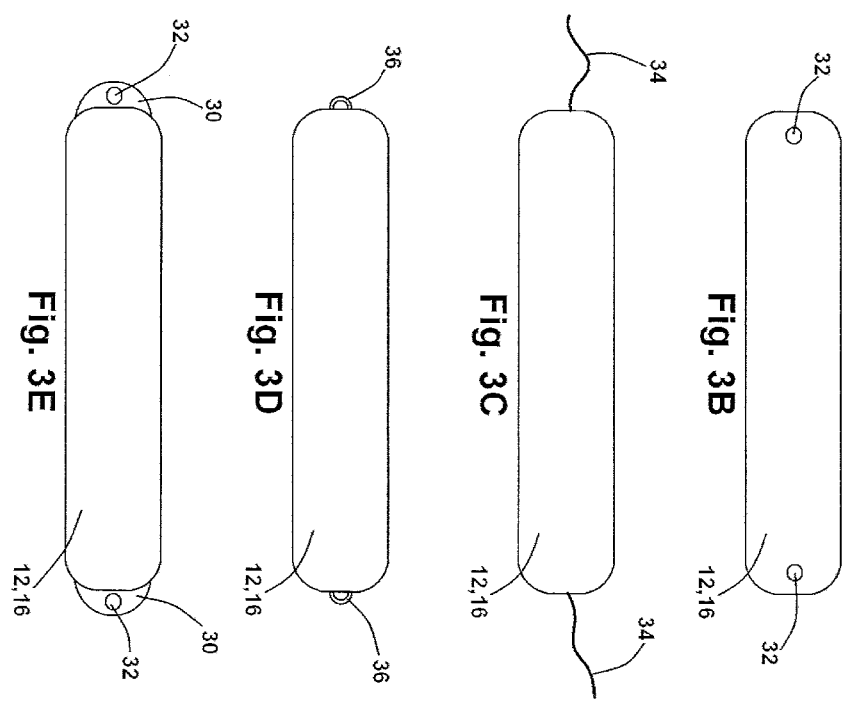

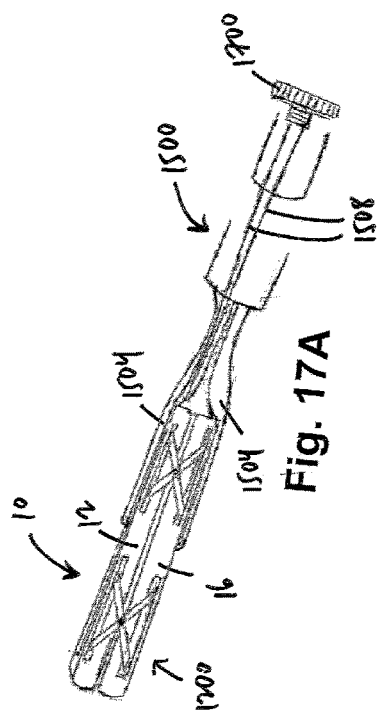
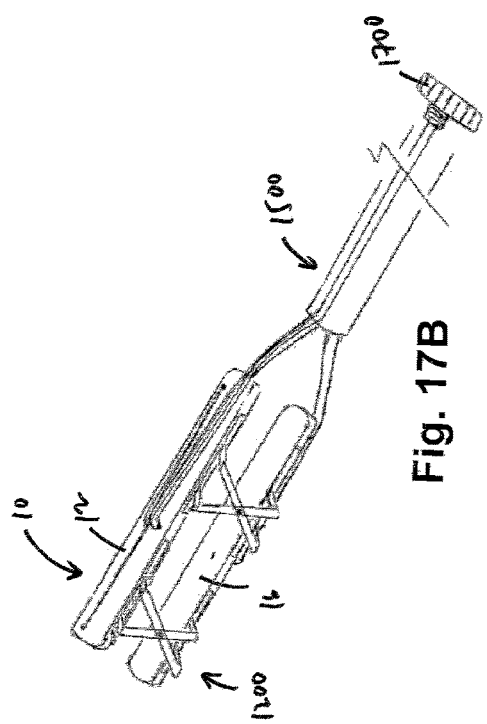
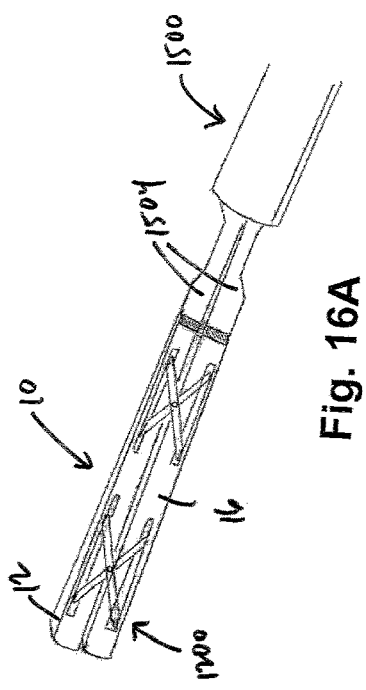
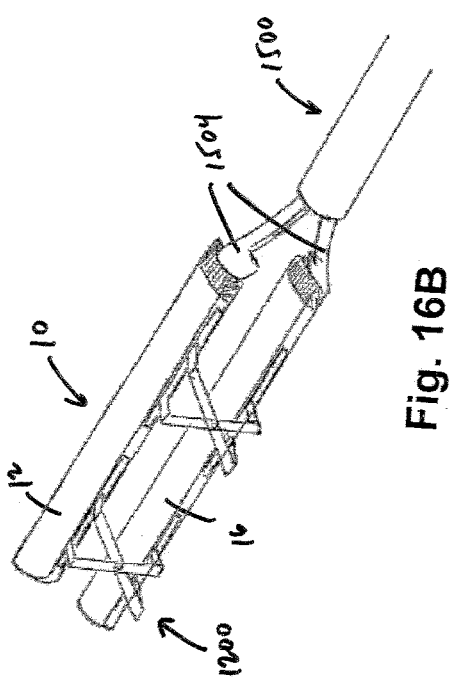

DEVICES AND SYSTEMS CONFIGURED TO FIT AROUND A TISSUE OR ORGAN AND METHODS OF THE SAME

PRIORITY

The present application is related to, claims the priority benefit of, and is a U.S. continuation application of, U.S. patent application Ser. No. 14/215,829, filed Mar. 17, 2014 and issued as U.S. Pat. No. 9,980,841 on May 29, 2018, which a) is related to, and claims the priority benefit of, U.S. Provisional Patent Application Ser. No. 61/800,687 filed Mar. 15, 2013, and b) is related to, claims the priority benefit of, and is a U.S. continuation-in-part patent application of, U.S. patent application Ser. No. 13/080,586, filed Apr. 5, 2011, which is related to, claims the priority benefit of, and is a U.S. continuation-in-part patent application of, U.S. patent application Ser. No. 12/861,251, filed Aug. 23, 2010, which is related to, claims the priority benefit of, and is a U.S. continuation-in-part patent application of, U.S. patent application Ser. No. 12/546,139, filed Aug. 24, 2009. The contents of each of these applications and patents are hereby incorporated by reference in their entirety into this disclosure.

BACKGROUND

Organ and tissue surgical restoration are clinical techniques that may be applied to numerous different body tissues, ranging from blood vessels to whole organs. Conventionally, such surgical techniques require the use of incisions, pins, staples and/or significant sutures in order to alter the tissue's anatomy. For example, surgical gastric restoration often employed to treat obesity and typically involves the reorganization of the digestive tract. Conventional examples of such procedures involve attempts to either 1) restrict food intake into the body via a restrictive bariatric procedure (a "Restrictive Procedure"), or 2) alter the anatomy of the small intestine or divert the peristalsis of a person's normal food intake past the small intestine to decrease caloric absorption via a malabsorptive bariatric procedure, which is commonly known as a gastric bypass (a "Malabsorptive Procedure"). It is also known to combine the two procedures such that both of the aforementioned techniques are employed jointly.

Malabsorptive Procedures entail an intestinal bypass that results in the exclusion of almost all of the small intestine from the digestive tract. In most Malabsorbptive Procedures, a portion of the stomach or small intestine is removed from the digestive tract through a surgical procedure that requires cutting the digestive tissue and thereafter closing any holes or securing the newly formed anatomy with staples and/or sutures. Conversely, Restrictive Procedures generally involve the creation of a passageway extending from the upper portion of the stomach to the lower portion of the stomach in order to decrease the size of the organ and thus prevent the stomach from storing large amounts of food. Conventional Restrictive Procedures rely on the banding, suturing and/or stapling of the stomach to create a small pouch on the superior portion of the stomach near the gastroesophageal junction.

Combined operations consisting of Malabsorptive and Restrictive Procedures are the most common bariatric procedures performed today. An example of a combined procedure is the Extended (Distal) Roux-en-Y Gastric Bypass in which a stapling creates a small stomach pouch (approximately 15 to 20 cc) completely separated from the remainder of the stomach. In addition, the small intestine is divided just beyond the duodenum (the hollow tube connecting the stomach to the jejunum), re-arranged into a Y-configuration, and sutured to the small upper stomach pouch to enable the outflow of food therefrom through the newly formed "Roux limb."

Accordingly, most digestive tract restoration procedures require that the stomach and/or tissue of the intestine is cut and thereafter sutured or stapled back together. As the digestive tract contains numerous enzymes, strong acids and multiple species of bacteria that assist with digestion, the perforation of an organ and/or tissue thereof is particularly problematic due to the likelihood of leakage therefrom and/or increased risk of serious infection. As such, conventional gastric surgical restoration procedures have high rates of post-operative complications that may require prolonged hospitalization and even additional operations, and are often irreversible and/or permanently affect the restored tissue and/or organ. Accordingly, a need exists for safe and effective devices and methods for restoring organs and tissue that are reversible and do not require cutting or penetrating the underlying tissue with significant sutures, staples and/or pins.

It will be appreciated that the foregoing examples are only provided as examples and that there are numerous other indications where intervention is necessary either to restore the underlying organ or tissue and/or to provide support thereto.

BRIEF SUMMARY

In at least one embodiment of an implantable restraining device of the present disclosure, the device comprises a first engaging component and a second engaging component, the first and second engaging components configured for laparoscopic insertion into a body cavity, and at least one connector coupled to the first engaging component and the second engaging component. In at least one embodiment, the at least one connector is capable of comprising a first configuration relative to the first engaging component and the second engaging component whereby the first engaging component and the second engaging component are positioned relative to one another to fit within a laparoscopic port, and is further capable of comprising a second configuration relative to the first engaging component and the second engaging component whereby the first engaging component and the second engaging component are spaced apart from one another so that an interior space having a value is defined therebetween. In an additional embodiment, the at least one connector is capable of moving between a first position that is substantially parallel with the first engaging component and the second engaging component, and a second position that is substantially perpendicular with the first engaging component and the second engaging component. In yet another embodiment, the first engaging component and the second engaging component are configured to engage a targeted tissue therebetween when the at least one connector is/are in a second configuration relative to the first engaging component and the second engaging component.

In at least one embodiment of an implantable restraining device of the present disclosure, at least one of the first engaging component and the second engaging component further comprises one or more suturing elements chosen from the group of one or more pads, one or more apertures, and/or one or more suture members, each of the one or more suturing elements capable of receiving a suture therethrough. In another embodiment, the first engaging component and the second engaging component further comprise one or more strings, wherein said strings may be coupled to one another to secure the device about a stomach. In yet another embodiment, the first engaging component and the second engaging component each comprise a proximal end, a distal end, and a body extending therebetween, wherein the body of the first engaging component is configured to conform to a first targeted tissue surface, and the body of the second engaging component is configured to conform to a second targeted tissue surface. In an additional embodiment, the at least one connector is rotatably coupled with the body of the first engaging component and the body of the second engaging component. In yet an additional embodiment, the at least one connector comprises a first connector and a second connector, wherein the first connector is coupled to the distal end of the first engaging component and the distal end of the second engaging component, and wherein the second connector is coupled to the proximal end of the first engaging component and the proximal end of the second engaging component.

In at least one embodiment of an implantable restraining device of the present disclosure, each of the first engaging component and the second engaging component comprise a configuration chosen from a straight bar configuration, a curved configuration, or a circular configuration. In an additional embodiment, the first engaging component and the second engaging component are flexible or semi-flexible. In yet an additional embodiment, the first engaging component, the second engaging component, and the at least one connector each comprise a material suitable to resist corrosion, the material chosen from polyurethane, polyethylene, polytetrafluoroethylene, nitinol, silastic, titanium, and/or stainless steel. In another embodiment, when a force is applied to the at least one connector, the value of the interior space is increased.

In at least one embodiment of an implantable restraining device of the present disclosure, the at least one connector comprises at least one spring having at least one coil. In another embodiment, the at least one spring comprises at least one torsion spring. In yet another embodiment, the at least one coil of the at least one spring comprises three or more coils. In an additional embodiment, an outermost diameter of the at least one spring is less than about 15 millimeters. In a further embodiment, the at least one spring comprises a first rod and a second rod extending from the coil, wherein the first rod is coupled to the first engaging component and the second rod is coupled to the second engaging component.

In at least one embodiment of an implantable restraining device of the present disclosure, the value of the interior space defined between the first engaging component and the second engaging component when the at least one connector comprises a second configuration corresponds to an outer dimension of a stomach so that the device, when positioned about a stomach, fits about the stomach without providing any clamping pressure upon said stomach. In an additional embodiment, each of the first engaging component and the second engaging component have a width between 5 mm and 15 mm and have a length between 30 mm and 200 mm. In yet an additional embodiment, when the at least one connector comprises a first configuration, the at least one connector operates to compress the first engaging component and the second engaging component toward one another so that the value of the interior space approaches zero. In another embodiment, the first engaging component further comprises one or more pads affixed thereto, each of the one or more pads capable of receiving a suture therethrough.

In at least one embodiment of an implantable restraining device of the present disclosure, the at least one connector comprises at least one strut, the at least one strut rotatably coupled to the first engaging component and the second engaging component. In another embodiment, the at least one strut comprises at least two struts, and wherein the device further comprises a mesh curtain coupled to at least two of the at least two struts, the mesh curtain operable to limit organ distension or remodeling when the device is positioned about an organ. In an additional embodiment, the mesh curtain defines at least one mesh aperture, the at least one mesh aperture sized to permit a user to grasp an organ within the at least one mesh aperture to facilitate positioning the device about the organ. In yet an additional embodiment, said device is sized and shaped so that a demi shaft may engage the device so that the device may be positioned within a body cavity, and removal of the demi shaft from the device allows the first engaging component and the second engaging component to separate from one another.

In at least one embodiment of an implantable restraining device of the present disclosure, the device further comprises a mesh curtain coupled to the first engaging component and the second engaging component, the mesh curtain operable to limit organ distension or remodeling when the device is positioned about an organ. In another embodiment, the device further comprises pliable junctions within the first engaging component and the second engaging component to divide each component into two separate subcomponents, wherein each of the two separate subcomponents of the first engaging component and the second engaging component are connected to one another by way of a flexible structure.

In at least one embodiment of an implantable restraining device of the present disclosure, the at least one connector comprises at least two connectors, the at least two connectors each comprising a coupler, said coupler comprising at least two coupler arms connected to a coupler bar. In an additional embodiment, each of the first engaging component and the second engaging component define apertures sized and shaped to fit said coupler arms so that said coupler arms may inserted within said apertures. In yet an additional embodiment, at least one of the at least two coupler arms comprises a coupler protrusion positioned at or near a distal end of said arms, and wherein the first engaging component and the second engaging component comprise at least one stop at the corresponding aperture where said arm comprises a coupler protrusion, the coupler protrusion sized and shaped to restrict removal of coupler from the first engaging component and the second engaging component upon engagement of said stop. In another embodiment, the at least two coupler arms of each coupler comprise a pivot member positioned therethrough so that the at least two coupler arms may pivot about one another at the pivot member. In yet another embodiment, each of the first engaging component and the second engaging component define apertures sized and shaped to fit said coupler arms so that said coupler arms may inserted within said apertures and so that said coupler arms may move in a lateral direction corresponding to the first engaging component and the second engaging component. In an additional embodiment, one or more protrusions positioned within at least one aperture are capable of facilitating fixation of coupler arms in a desired position.

In at least one embodiment of an implantable restraining device of the present disclosure, the device comprises the first engaging component and the second engaging component each define an opening, said opening sized and shaped to accept arms of an apparatus useful to position the device within a body cavity. In an additional embodiment, the at least one connector comprises a resorbable material, and wherein when the device is positioned about a stomach, the at least one connector resorbs within a body over time so that the at least one connector is no longer coupled to the first engaging component and the second engaging component. In yet an additional embodiment, the first engaging component and the second engaging component comprise a resorbable material, and when the device is positioned about a stomach, the first engaging component and the second engaging component resorb within a body over time so that the first engaging component and the second engaging component are no longer coupled to one another by way of the at least one connector. In another embodiment, at least one of the first engaging component, the second engaging component, and the at least one connector comprise a resorbable material chosen from polyglycolide (PGA), polylactide (PLA), l-lactide (LPLA), poly(dl-lactide) (DLPLA), poly(.epsilon.-caprolactone) (PCL), poly(dioxanone) (PDO), polyglycolide-trimethylene carbonate (PGA-TMC), or poly(d,l-lactide-co-glycolide) (DLPLG).

In at least one embodiment of an apparatus for delivering a restraining device of the present disclosure, the apparatus comprises a shaft comprising a distal end, the shaft defining a lumen positioned therethrough, at least one arm operably coupled to the shaft at or near the distal end of the shaft, the at least one arm configured to engage a restraining device comprising a first engaging component, a second engaging component, and at least one connector coupled to the first engaging component and the second engaging component, and at least one pull bar having a distal end, the at least one pull par positioned at least partially within the lumen of the shaft. In at least another embodiment, when a string coupled to the at least one connector is engaged by the at least one pull bar at or near the distal end of the at least one pull bar, the at least one pull bar is operable to change the configuration of the at least one connector upon retraction of the at least one pull bar within the lumen of the shaft. In an additional embodiment, the at least one arm comprises a first arm and a second arm, the first arm operable to engage the first engaging component of the restraining device and the second arm operable to engage the second engaging component of the restraining device. In yet an additional embodiment, movement of the first arm and the second arm in a first direction facilitates the separation of the first engaging component from the second engaging component.

In at least one embodiment of an apparatus for delivering a restraining device of the present disclosure, the apparatus comprises a shaft comprising a proximal end and a distal end, the shaft defining a lumen positioned therethrough, at least one arm operably coupled to the shaft at or near the distal end of the shaft, the at least one arm configured to engage a restraining device comprising a first engaging component, a second engaging component, and at least one connector coupled to the first engaging component and the second engaging component, and at least one string rotator, the at least one string rotator positioned at or near the proximal end of the shaft, wherein when a string coupled to the at least one connector is engaged by the at least string rotator, the at least one string rotator is operable to change the configuration of the at least one connector upon rotation of the at least one string rotator.

In at least one embodiment of a system for restoring a tissue of the present disclosure, the system comprises an exemplary implantable restraining device of the present disclosure and an exemplary an apparatus for delivering the restraining device of the present disclosure.

In at least one embodiment of a method for restoring a targeted tissue of the present disclosure, the method comprising the steps of inserting an exemplary implantable restraining device of the present disclosure into a body cavity, increasing the value of the interior space between the first engaging component and the second engaging component of the device by positioning the at least one connector in a second configuration, and positioning the first engaging component and the second engaging component of the device over the targeted tissue such that the targeted tissue is positioned within the interior space, wherein when the targeted tissue expands in a direction between the first engaging component and the second engaging component, the targeted tissue exerts a force upon the first engaging component and the second engaging component. In another embodiment, the targeted tissue is a stomach, and expansion of the stomach, with said device positioned thereon, functionally divides the stomach into a first stomach portion and a second stomach portion. In yet another embodiment, the targeted tissue is a stomach and wherein the first engaging component and the second engaging component comprise one or more suturing elements positioned at or near the distal ends of each said component, the one or more suturing elements capable of receiving a suture therethrough to approximate the distal ends of said components toward one another. In an additional embodiment, said approximation of the distal ends of the first engaging component and the second engaging component toward one another prevents a fistula so that food entering the stomach enters a first stomach portion and not the stomach fundus. In yet an additional embodiment, the distal ends of the first engaging component and the second engaging component extend beyond the stomach when the device is positioned over the stomach.

In at least one embodiment of an implantable restraining device of the present disclosure, the device comprises a first engaging component and a second engaging component configured for laparoscopic insertion into a body cavity, wherein at least one of the first engaging component and/or the second engaging component comprises one or more suturing elements, and wherein the first engaging component and the second engaging component each comprise a material suitable to resist corrosion, and at least one connector coupled to the first engaging component and the second engaging component, the at least one connector capable of comprising a first configuration relative to the first engaging component and the second engaging component whereby the first engaging component and the second engaging component are positioned relative to one another to fit within a laparoscopic port, the at least one connector capable of comprising a second configuration relative to the first engaging component and the second engaging component whereby the first engaging component and the second engaging component are spaced apart from one another so that an interior space having a value is defined therebetween, wherein when the device is positioned about a stomach, the device fits about the stomach without providing any clamping pressure upon said stomach.

In at least one embodiment of a method for removing a restraining device from a body of the present disclosure, the method comprising the steps of withdrawing a restraining device from a tissue or organ to which it is positioned, configuring the restraining device fit within a laparoscopic port, and removing restraining device from the body through the laparoscopic port. In another embodiment, said method is preceded by the step of positioning the laparoscopic port within the body to facilitate removal of the restraining device. In yet another embodiment, the method further comprises the step of removing the laparoscopic port from the body.

In at least one exemplary embodiment of an implantable restraining device of the present disclosure, the device comprises a first engaging component and a second engaging component, each component configured for laparoscopic insertion into a body cavity, a first swivel arm defining a first bend and a second swivel arm defining a second bend, the first swivel arm coupled to the first engaging component at a first pivot point and coupled to the second engaging component at a second pivot point, and the second swivel arm coupled to the first engaging component at a third pivot point and coupled to the second engaging component at a fourth pivot point, and a first interconnection arm and a second interconnection arm, the first interconnection arm connected to the first swivel arm relative to the first bend, and the second interconnection arm connected to the second swivel arm relative to the second bend. In another embodiment, the first swivel arm and the second swivel arm are capable of moving between a first position that is substantially parallel with the first engaging component and the second engaging component and a second position that is substantially perpendicular with the first engaging component and the second engaging component. In yet another embodiment, the first engaging component and the second engaging component are configured to engage a targeted tissue therebetween when the first swivel arm and the second swivel arm are in a configuration relatively perpendicular to the first engaging component and the second engaging component. In an additional embodiment, the first engaging component and the second engaging component each define one or more studs sized and shaped to permit the first swivel arm and the second swivel arm to be coupled thereto.

In at least one exemplary embodiment of an implantable restraining device of the present disclosure, the first swivel arm and the second swivel arm further define one or more curvatures, whereby the first bend, the second bend, and the one or more curvatures define a native U-shaped configuration. In an additional embodiment, the device further comprises a tape positioned around at least part of the device so that the tape engages the first interconnection arm and the second interconnection arm. In another embodiment, the tape is capable of decreasing an interior space defined between the first engaging component and the second engaging component when the tape applies a force to the first interconnection arm and the second interconnection arm. In yet another embodiment, the tape further comprises one or more detectable portions positioned/imprinted thereon. In various embodiments, the one or more detectable portions are radiopaque.

In at least one exemplary embodiment of an implantable restraining device of the present disclosure, the device further comprises a cover flap, the cover flap coupled to either the first engaging component or the second engaging component, the cover flap capable of either further coupling to the second engaging component when initially coupled to the first engaging component or further coupling to the first engaging component when initially coupled to the second engaging component. In another embodiment, the at least one of the first engaging component and the second engaging component define one or more suture apertures therethrough. In yet another embodiment, the first engaging component and the second engaging component each comprise a proximal end, a distal end, and a body extending therebetween, wherein the body of the first engaging component is configured to conform to a first targeted tissue surface, and the body of the second engaging component is configured to conform to a second targeted tissue surface.

In at least one exemplary embodiment of an implantable restraining device of the present disclosure, the device further comprises a first adjustment rod and a second adjustment rod, each of the first adjustment rod and the second adjustment rod comprising a distal end, a proximal end, and threading therebetween, and a dial rotatably coupled thereto at or near the threading. In another embodiment, the first adjustment rod is coupled to the first swivel arm and the first interconnection arm, and wherein the second adjustment rod is coupled to the second swivel arm and the second interconnection arm. In yet another embodiment, rotation of the dial on either or both of the first adjustment rod and/or the second adjustment rod facilitates movement of the first engaging component and the second engaging component. In an additional embodiment, rotation of the dial in a first direction causes the first engaging component and the second engaging component to move toward one another, and wherein rotation of the dial in a second direction causes the first engaging component and the second engaging component to move away from one another.

In at least one exemplary embodiment of an implantable restraining device of the present disclosure, each of the first adjustment rod and the second adjustment rod further comprises a bar coupled thereto at or near the distal ends of said rods. In an additional embodiment the bar coupled to the first adjustment rod is positioned distal to the first interconnection arm, and wherein the bar coupled to the second adjustment rod is positioned distal to the second interconnection arm, and wherein rotation of the dial on either or both of the first adjustment rod and/or the second adjustment rod facilitates movement of the first engaging component and the second engaging component. In yet an additional embodiment each of the first adjustment rod and the second adjustment rod further comprises a cap coupled thereto at or near the proximal ends of said rods, said caps configured to prevent said dials from disengaging said adjustment rods. In another embodiment, said dials define a dial aperture therethrough, the dial configured to permit an indicia present upon said adjustment rods to be viewed therethrough. In yet another embodiment, each of the first engaging component and the second engaging component define one or more facets along at least part of a length of said engaging components, said facets providing a generally arcuate profile of said engaging components.

In at least one exemplary embodiment of an implantable restraining device of the present disclosure, each of the first engaging component and the second engaging component comprise a configuration chosen from a straight bar configuration, a curved configuration, or a circular configuration. In an additional embodiment, the first engaging component and the second engaging component are flexible or semi-flexible. In various embodiments, the first engaging component, the second engaging component, the first swivel arm, and the second swivel arm each comprise a material suitable to resist corrosion selected from the group consisting of polyurethane, polyethylene, polytetrafluoroethylene, nitinol, silastic, titanium, and stainless steel. In various embodiments, the first engaging component, the second engaging component, the first swivel arm, and the second swivel arm comprise a resorbable material selected from the group consisting of polyglycolide (PGA), polylactide (PLA), l-lactide (LPLA), poly(dl-lactide) (DLPLA), poly(c- caprolactone) (PCL), poly(dioxanone) (PDO), polylglycolide-trimethylene carbonate (PGA-TMC), or poly(d,l-lactide-co-glycolide) (DLPLG).

In at least one exemplary embodiment of implantable restraining device of the present disclosure, the device comprises a first engaging component defining a first bend and a second engaging component defining a second bend, the first and second engaging components configured for laparoscopic insertion into a body cavity, a first swivel arm and a second swivel arm, the first swivel arm coupled to the first engaging component at a first pivot point and coupled to the second engaging component at a second pivot point, and the second swivel arm coupled to the first engaging component at a third pivot point and coupled to the second engaging component at a fourth pivot point, a first interconnection arm and a second interconnection arm, the first interconnection arm connected to the first swivel arm relative to the first bend, and the second interconnection arm connected to the second swivel arm relative to the second bend, a tape positioned around at least part of the device so that the tape engages the first interconnection arm and the second interconnection arm, and a cover flap, the cover flap coupled to either the first engaging component or the second engaging component, the cover flap capable of either further coupling to the second engaging component when initially coupled to the first engaging component or further coupling to the first engaging component when initially coupled to the second engaging component, wherein the first swivel arm and the second swivel arm are capable of moving between a first position that is substantially parallel with the first engaging component and the second engaging component and a second position that is substantially perpendicular with the first engaging component and the second engaging component.

In at least one exemplary embodiment of implantable restraining device of the present disclosure, the device comprises a first engaging component and a second engaging component, each component configured for laparoscopic insertion into a body cavity, a first swivel arm defining a first bend and a second swivel arm defining a second bend, the first swivel arm coupled to the first engaging component at a first pivot point and coupled to the second engaging component at a second pivot point, and the second swivel arm coupled to the first engaging component at a third pivot point and coupled to the second engaging component at a fourth pivot point, a first interconnection arm and a second interconnection arm, the first interconnection arm connected to the first swivel arm relative to the first bend, and the second interconnection arm connected to the second swivel arm relative to the second bend, a first adjustment rod and a second adjustment rod, each of the first adjustment rod and the second adjustment rod comprising a distal end, a proximal end, and threading therebetween, a dial rotatably coupled thereto at or near the threading, and a bar coupled thereto at or near the distal ends of said adjustment rods, wherein the first adjustment rod is coupled to the first swivel arm and the first interconnection arm, and wherein the second adjustment rod is coupled to the second swivel arm and the second interconnection arm, wherein rotation of the dial in a first direction causes the first engaging component and the second engaging component to move toward one another, and wherein rotation of the dial in a second direction causes the first engaging component and the second engaging component to move away from one another, and wherein the first swivel arm and the second swivel arm are capable of moving between a first position that is substantially parallel with the first engaging component and the second engaging component and a second position that is substantially perpendicular with the first engaging component and the second engaging component.

In at least one exemplary embodiment of a method for restoring a targeted tissue of the present disclosure, the method comprises the steps of inserting an implantable restraining device into a body cavity of a mammalian body, the implantable restraining device comprising a first engaging component defining a first bend and a second engaging component defining a second bend, the first and second engaging components configured for laparoscopic insertion into a body cavity, a first swivel arm and a second swivel arm, the first swivel arm coupled to the first engaging component at a first pivot point and coupled to the second engaging component at a second pivot point, and the second swivel arm coupled to the first engaging component at a third pivot point and coupled to the second engaging component at a fourth pivot point, and a first interconnection arm and a second interconnection arm, the first interconnection arm connected to the first swivel arm relative to the first bend, and the second interconnection arm connected to the second swivel arm relative to the second bend, advancing the implantable restraining device to a location within the mammalian body adjacent to a targeted tissue, swiveling the first swivel arm and the second swivel arm so that the first swivel arm and the second swivel arm are substantially perpendicular to the first engaging component and the second engaging component, and positioning the first engaging component and the second engaging component over the targeted tissue such that at least a portion of the targeted tissue is positioned therebetween, wherein when the targeted tissue expands in a direction between the first engaging component and the second engaging component, the targeted tissue exerts a force upon the first engaging component and the second engaging component. In another embodiment, the method further comprises the step of securing one or more sutures to connect the first engaging component and/or the second engaging component to the targeted tissue. In yet another embodiment, the method further comprises the step of securing a cover flap coupled to either the first engaging component or the second engaging component so that the cover flap capable is either further coupled to the second engaging component when initially coupled to the first engaging component or further coupled to the first engaging component when initially coupled to the second engaging component. In an additional embodiment, the method further comprises the step of adjusting a tape positioned around at least part of the device whereby the tape engages the first interconnection arm and the second interconnection arm, wherein adjustment of the tape decreases an interior space defined between the first engaging component and the second engaging component when the tape applies a force to the first interconnection arm and the second interconnection arm, and wherein adjustment of the tape increases an interior space defined between the first engaging component and the second engaging component when the force is removed or reduced. In various embodiments, the targeted tissue is a stomach, and wherein expansion of the stomach, with said device positioned thereon, functionally divides the stomach into a first stomach portion and a second stomach portion. In at least another embodiment, the implantable restraining device further comprises a first adjustment rod and a second adjustment rod, each of the first adjustment rod and the second adjustment rod having a dial rotatably coupled thereto, wherein the first adjustment rod is coupled to the first swivel arm and the first interconnection arm, and wherein the second adjustment rod is coupled to the second swivel arm and the second interconnection arm, and wherein the method further comprises the step, of rotating said dials to adjust an interior space between the first engaging component and the second engaging component.

In at least one exemplary embodiment of an implantable restraining device of the present disclosure, the device comprises a first engaging component and a second engaging component at least substantially parallel to one another, a first swivel arm, comprising a first fixed arm, a first expandable arm, and a first hub, wherein the first fixed arm is pivotally connected to the first engaging component at or near a first fixed arm first end and is coupled to the first hub at or near a first fixed arm second end, and wherein the first expandable arm is pivotally connected to the second engaging component at or near a first expandable arm first end and is connected to the first hub at or near a first expandable arm second end by way of a first hub bracket, a second swivel arm, comprising a second fixed arm, a second expandable arm, and a second hub, wherein the second fixed arm is pivotally connected to the first engaging component at or near a second fixed arm first end and is coupled to the second hub at or near a second fixed arm second end, and wherein the second expandable arm is pivotally connected to the second engaging component at or near a second expandable arm first end and is connected to the second hub at or near a second expandable arm second end by way of a second hub bracket, and wherein the first expandable arm and the second expandable are capable of movement relative to the first hub and the second hub respectively so that a distance between the first engaging component and the second engaging component may change relative to movement of the first expandable arm and the second expandable arm. In another embodiment, the first swivel arm is capable of rotation in a first direction, and wherein the second swivel arm is capable of rotation in an opposing second direction. In yet another embodiment, the first swivel arm and the second swivel arm are capable of rotation so that the first swivel arm, the second swivel arm, the first engaging component, and the second engaging component share a common linear axis. In an additional embodiment, the first swivel arm and the second swivel arm are capable of rotation so that the first swivel arm and the second swivel arm are substantially or fully perpendicular to the first engaging component and the second engaging component. In an additional embodiment, the first fixed arm is relatively shorter than the second fixed arm, and wherein the first expandable arm is relatively shorter than the second expandable arm.

In at least one exemplary embodiment of an implantable restraining device of the present disclosure, the device further comprises a first arm flange at or near the first expandable arm second end, the first arm flange configured to limit expansion of the first expandable arm relative to the first fixed arm, and a second arm flange at or near the second expandable arm second end, the second arm flange configured to limit expansion of the second expandable arm relative to the second fixed arm. In an additional embodiment, the device is sized and shaped to fit within a laparoscopic bodily port.

In at least one exemplary embodiment of an implantable restraining device of the present disclosure, the device further comprises a first strap positioned at a first end of the first engaging component and at a first end of the second engaging component, the first strap configured to limit movement of the first engaging component and the second engaging component when the first strap is coupled to the first engaging component and the second engaging component. In an additional embodiment, the first strap is fixedly coupled to one of the first end of the first engaging component or the first end of the second engaging component. In yet an additional embodiment, the first strap is coupled to one of the first end of the first engaging component or the first end of the second engaging component by way of at least one suture. In another embodiment, the first strap has at least one suture aperture defined therethrough, and wherein at least one of the first engaging component and the second engaging component has at least one plate aperture defined therethrough, the at least one suture aperture and the at least one plate aperture configured to permit a suture to be placed therethrough to couple the first strap to either the first engaging component or the second engaging component.

In at least one exemplary embodiment of an implantable restraining device of the present disclosure, the device further comprises a first pad coupled to one or both of the first fixed arm and the first expandable arm, and a second pad coupled to one or both of the second fixed arm and the second expandable arm, wherein the first pad and the second pad are configured to engage at least a portion of a mammalian bodily organ positioned therebetween. In another embodiment, the first engaging component and the second engaging component are configured to engage a targeted tissue therebetween when the first swivel arm and the second swivel arm are in a configuration relatively perpendicular to the first engaging component and the second engaging component. In yet another embodiment, the first engaging component, the second engaging component, the first swivel arm, and the second swivel arm each comprise a material suitable to resist corrosion selected from the group consisting of polyurethane, polyethylene, polytetrafluoroethylene, polyaryletherketone, carbothane, tecothane, nitinol, silastic, titanium, and stainless steel.

In at least one exemplary embodiment of an implantable restraining device of the present disclosure, each of the first engaging component and the second engaging component define one or more facets along at least part of a length of said engaging components, said facets providing a generally arcuate profile of said engaging components. In an additional embodiment, each of the first engaging component and the second engaging component comprise a configuration chosen from a straight bar configuration, a curved configuration, or a circular configuration. In yet an additional embodiment, the first engaging component and the second engaging component are flexible or semi-flexible.

In at least one exemplary embodiment of an implantable restraining device of the present disclosure, the device comprises a first engaging component and a second engaging component at least substantially parallel to one another, a first swivel arm, comprising a first fixed arm, a first expandable arm, and a first hub, wherein the first fixed arm is pivotally connected to the first engaging component at or near a first fixed arm first end and is coupled to the first hub at or near a first fixed arm second end, and wherein the first expandable arm is pivotally connected to the second engaging component at or near a first expandable arm first end and is connected to the first hub at or near a first expandable arm second end by way of a first hub bracket, a second swivel arm, comprising a second fixed arm, a second expandable arm, and a second hub, wherein the second fixed arm is pivotally connected to the first engaging component at or near a second fixed arm first end and is coupled to the second hub at or near a second fixed arm second end, and wherein the second expandable arm is pivotally connected to the second engaging component at or near a second expandable arm first end and is connected to the second hub at or near a second expandable arm second end by way of a second hub bracket, and a first strap positioned at one or both of a first end of the first engaging component and at a first end of the second engaging component, the first strap configured to limit movement of the first engaging component and the second engaging component when the first strap is coupled to the first engaging component and the second engaging component. wherein the first expandable arm and the second expandable are capable of movement relative to the first hub and the second hub respectively so that a distance between the first engaging component and the second engaging component may change relative to movement of the first expandable arm and the second expandable arm, and wherein the first swivel arm is capable of rotation in a first direction so that the first swivel arm, the second swivel arm, the first engaging component, and the second engaging component share a common linear axis, and wherein the second swivel arm is capable of rotation in an opposing second direction so that the first swivel arm and the second swivel arm are substantially or fully perpendicular to the first engaging component and the second engaging component.

In at least one embodiment of a method for restoring a targeted tissue of the present disclosure, the method comprises the steps of inserting an implantable restraining device into a body cavity of a mammalian body, the implantable restraining device comprising a first engaging component and a second engaging component at least substantially parallel to one another, a first swivel arm, comprising a first fixed arm, a first expandable arm, and a first hub, wherein the first fixed arm is pivotally connected to the first engaging component at or near a first fixed arm first end and is coupled to the first hub at or near a first fixed arm second end, and wherein the first expandable arm is pivotally connected to the second engaging component at or near a first expandable arm first end and is connected to the first hub at or near a first expandable arm second end by way of a first hub bracket, a second swivel arm, comprising a second fixed arm, a second expandable arm, and a second hub, wherein the second fixed arm is pivotally connected to the first engaging component at or near a second fixed arm first end and is coupled to the second hub at or near a second fixed arm second end, and wherein the second expandable arm is pivotally connected to the second engaging component at or near a second expandable arm first end and is connected to the second hub at or near a second expandable arm second end by way of a second hub bracket, advancing the implantable restraining device to a location within the mammalian body adjacent to a targeted tissue, swiveling the first swivel arm and the second swivel arm so that the first swivel arm and the second swivel arm are substantially perpendicular to the first engaging component and the second engaging component, and positioning the first engaging component and the second engaging component over the targeted tissue such that at least a portion of the targeted tissue is positioned therebetween, wherein when the targeted tissue expands in a direction between the first engaging component and the second engaging component, the targeted tissue exerts a force upon the first engaging component and the second engaging component so that the first expandable arm moves relative to the first hub and so that the second expandable arm moves relative to the second hub. In another embodiment, the targeted tissue is a stomach, and wherein expansion of the stomach, with said device positioned thereon, functionally divides the stomach into a first stomach portion and a second stomach portion.

In at least one embodiment of an implantable device of the present disclosure, the implantable device comprises a first engaging component comprising a first rigid inner plate at least partially surrounded by a first flexible coating, a second engaging component comprising a second rigid inner plate at least partially surrounded by a coating selected from the group consisting of the first flexible coating and the second flexible coating, a first c-ring and a second c-ring, the first c-ring coupled to the first engaging component at a first pivot point and coupled to the second engaging component at a second pivot point, and the second c-ring coupled to the first engaging component at a third pivot point and coupled to the second engaging component at a fourth pivot point, and a cover flap, the cover flap coupled to either the first engaging component or the second engaging component, the cover flap capable of either further coupling to the second engaging component when initially coupled to the first engaging component or further coupling to the first engaging component when initially coupled to the second engaging component, wherein each of the first engaging component and the second engaging component define a longitudinal axis, wherein the device is further configured for placement around at least part of a stomach, and wherein the first c-ring and the second c-ring are configured to move from a first position that is substantially coplanar with the first engaging component and the second engaging component to a second position that is substantially perpendicular with the first engaging component and the second engaging component so to open the device, said movement in a plane perpendicular to a plane defined by an interior space between the first engaging component and the second engaging component. In an additional embodiment, when the first c-ring and the second c-ring are not positioned within the interior space between the first engaging component and the second engaging component when in the second position when the device is open. In yet an additional embodiment, the first flexible coating extends beyond a perimeter of the first rigid plate and wherein the second flexible coating extends beyond a perimeter of the second rigid plate. In an additional embodiment, when the first flexible coating extends beyond a perimeter of the first rigid plate and when the second flexible coating extends beyond a perimeter of the second rigid plate, the first flexible coating and the second flexible coating prevents shearing and migration of the device when the first engaging component and the second engaging component contact the stomach.

In at least one embodiment of an implantable device of the present disclosure, the device further comprises a first swivel stop positioned along at least one of the first engaging component and the second engaging component, the first swivel stop configured to limit swiveling of the first c-ring, and a second swivel stop positioned along at least one of the first engaging component and the second engaging component, the second swivel stop configured to limit swiveling of the second c-ring. In an additional embodiment, at least one of the first c-ring and the second c-ring comprises at least one suture feature. In yet an additional embodiment, the cover flap comprises a first material surrounded at least substantially by a coating selected from the group consisting of the first flexible coating, the second flexible coating, and a third coating. In an additional embodiment, at least one tab aperture is defined within the cover flap, wherein one of the first engaging component and the second engaging component further comprises a tab, and wherein the tab is configured for insertion into the tab aperture. In yet an additional embodiment, one of the first engaging component and the second engaging component further comprises a loop coupled thereto, wherein at least a portion of the cover flap is configured to fit within the loop.

In at least one embodiment of an implantable device of the present disclosure, one of the first engaging component and the second engaging component comprises a component tab configured to fit within a tab receiver of at the other of the first engaging component and the second engaging component. In an additional embodiment, at least one of the first c-ring and the second c-ring comprises a first c-ring portion and a second c-ring portion. In yet an additional embodiment, the first c-ring portion and the second c-ring portion are coupled to one another by a coupler positioned at a pivot point. In an additional embodiment, the first c-ring portion and the second c-ring portion are configured to pivot about one another at the pivot point. In yet an additional embodiment, one of the first c-ring portion and the second c-ring portion comprises a post, wherein the other of the first c-ring portion and the second c-ring portion has a post aperture defined therein, and wherein the post aperture is configured to receive the post.

In at least one embodiment of an implantable device of the present disclosure, the first c-ring portion and the second c-ring portion are configured to move relative to one another when the post moves relative to the post aperture. In an additional embodiment, the first c-ring portion and the second c-ring portion are coupled to one another by a slider coupler coupled to one of the first c-ring portion and the second c-ring portion. In yet an additional embodiment, an engagement mechanism of one of the first c-ring portion and the second c-ring portion is configured to engage the slider coupler. In an additional embodiment, one of the first c-ring portion and the second c-ring portion comprises a joiner defining an inner threaded portion, wherein the other of the first c-ring portion and the second c-ring portion has an outer threaded portion, and wherein the inner threaded portion is configured to receive the outer threaded portion. In yet an additional embodiment, one of the first c-ring portion and the second c-ring portion comprises a c-ring stub, wherein the other of the first c-ring portion and the second c-ring portion has a post c-ring stub aperture defined therein, and wherein the c-ring stub aperture is configured to receive the c-ring stub.

In at least one embodiment of an implantable device of the present disclosure, the first c-ring portion and the second c-ring portion are configured to move relative to one another when the c-ring stub moves relative to the c-ring stub aperture. In an additional embodiment, the device further comprises a cover positioned around a portion of the first c-ring and the second c-ring at or near the c-ring stub. In yet an additional embodiment, the first c-ring portion and the second c-ring portion are coupled to one another by hinge coupled to the first c-ring portion and the second c-ring portion. In an additional embodiment, the first c-ring portion and the second c-ring portion can move relative to one another and relative to the hinge by way of at least two pivot points. In yet an additional embodiment, at least one of the first c-ring and the second c-ring comprises or is coupled to an elongated coupler having at least one living hinge defined therein.

In at least one embodiment of an implantable device of the present disclosure, the elongated coupler is configured to bend at the at least one living hinge. In an additional embodiment, the elongated coupler is configured to connect to a portion of a second elongated coupler coupled to the first c-ring or the second c-ring that is not coupled to the elongated coupler. In yet an additional embodiment, at least one of the first c-ring and the second c-ring comprises a metal insert at least substantially surrounded by a coating selected from the group consisting of the first flexible coating, the second flexible coating, and a third coating. In an additional embodiment, the first engaging component and the second engaging component are configured to engage a targeted tissue therebetween when the first c-ring and the second c-ring are in a configuration relatively perpendicular to the first engaging component and the second engaging component. In yet an additional embodiment, at least one of the first engaging component and the second engaging component define one or more suture apertures therethrough.

In at least one embodiment of an implantable device of the present disclosure, the first engaging component and the second engaging component each comprise a proximal end, a distal end, and a body extending therebetween, wherein the body of the first engaging component is configured to conform to a first targeted tissue surface, and the body of the second engaging component is configured to conform to a second targeted tissue surface. In an additional embodiment, each of the first engaging component and the second engaging component define one or more facets along at least part of a length of said engaging components, said facets providing a generally arcuate profile of said engaging components. In yet an additional embodiment, each of the first engaging component and the second engaging component comprise a configuration chosen from a straight bar configuration, a curved configuration, or a circular configuration. In an additional embodiment, the first engaging component and the second engaging component are flexible or semi-flexible. In yet an additional embodiment, the first engaging component, the second engaging component, the first c-ring, and the second c-ring each comprise a material suitable to resist corrosion selected from the group consisting of polyurethane, polyethylene, polytetrafluoroethylene, nitinol, silastic, titanium, and stainless steel.

In at least one embodiment of an implantable device of the present disclosure, the first engaging component, the second engaging component, the first c-ring, and the second c-ring comprise a resorbable material selected from the group consisting of polyglycolide (PGA), polylactide (PLA), l-lactide (LPLA), poly(dl-lactide) (DLPLA), poly(.epsilon.-caprolactone) (PCL), poly(dioxanone) (PDO), polylglycolide-trimethylene carbonate (PGA-TMC), or poly(d,l-lactide-co-glycolide) (DLPLG). In an additional embodiment, the device is configured for laparascopic insertion into a body cavity.

In at least one embodiment of method for using an implantable device of the present disclosure, the method comprising the steps of inserting an implantable device into a mammalian body, the implantable device comprising a first engaging component comprising a first rigid inner plate at least partially surrounded by a first flexible coating, a second engaging component comprising a second rigid inner plate at least partially surrounded by a coating selected from the group consisting of the first flexible coating and the second flexible coating, a first c-ring and a second c-ring, the first c-ring coupled to the first engaging component at a first pivot point and coupled to the second engaging component at a second pivot point, and the second c-ring coupled to the first engaging component at a third pivot point and coupled to the second engaging component at a fourth pivot point, and a cover flap, the cover flap coupled to either the first engaging component or the second engaging component, the cover flap capable of either further coupling to the second engaging component when initially coupled to the first engaging component or further coupling to the first engaging component when initially coupled to the second engaging component, wherein each of the first engaging component and the second engaging component define a longitudinal axis, advancing the implantable device to a location within the mammalian body adjacent to a targeted tissue, swiveling the first c-ring and the second c-ring so that the first c-ring and the second c-ring are substantially perpendicular to the first engaging component and the second engaging component, and positioning the first engaging component and the second engaging component over the targeted tissue such that at least a portion of the targeted tissue is positioned therebetween. In another embodiment, when the targeted tissue expands in a direction between the first engaging component and the second engaging component, the targeted tissue exerts a force upon the first engaging component and the second engaging component. In yet another embodiment, the step of inserting is performed laparoscopically. In an additional embodiment, the step of inserting is performed surgically.

In at least one embodiment of method for using an implantable device of the present disclosure, the step of positioning is performed to position the first engaging component and the second engaging component over at least part of a stomach. In an additional embodiment, the method is performed to treat an obese patient. In yet an additional embodiment, the method is performed so that a patient using the implantable device can achieve satiety faster than if the implantable device was not used. In another embodiment, the method is performed to reduce a potential amount of food intake by reducing or eliminating an amount of food that can enter a fundus of the stomach. In yet another embodiment, the step of swiveling is performed to move the first c-ring and the second c-ring from a first position that is substantially coplanar with the first engaging component and the second engaging component to a second position that is substantially perpendicular with the first engaging component and the second engaging component so to open the implantable device, said movement in a plane perpendicular to a plane defined by an interior space between the first engaging component and the second engaging component.

In at least one embodiment of method for using an implantable device of the present disclosure, the method further comprises the step of securing one or more sutures to connect the first engaging component and/or the second engaging component to the targeted tissue. In another embodiment, the method further comprises the step of securing the cover flap so that the cover flap is secured to the first engaging component and the second engaging component. In yet another embodiment, wherein the targeted tissue is a stomach, and wherein expansion of the stomach, with said device positioned thereon, functionally divides the stomach into a first stomach portion and a second stomach portion. In an additional embodiment, the method further comprises the step of securing the cover flap over a fundus of the stomach so that the cover flap is secured to the first engaging component and the second engaging component.

BRIEF DESCRIPTION OF THE DRAWINGS

FIG. 3A shows a top view of at least one embodiment of a restraining device for restoring and/or supporting a tissue or organ according to the present disclosure;

FIGS. 3B through 3E show various embodiments of engaging components according to the present disclosure;

FIGS. 16A and 16B show exemplary embodiments of an apparatus for delivering a restraining device comprising a coupler according to the present disclosure;

FIGS. 17A and 17B show additional exemplary embodiments of an apparatus for delivering a restraining device according to the present disclosure;

DETAILED DESCRIPTION

Figure 1:
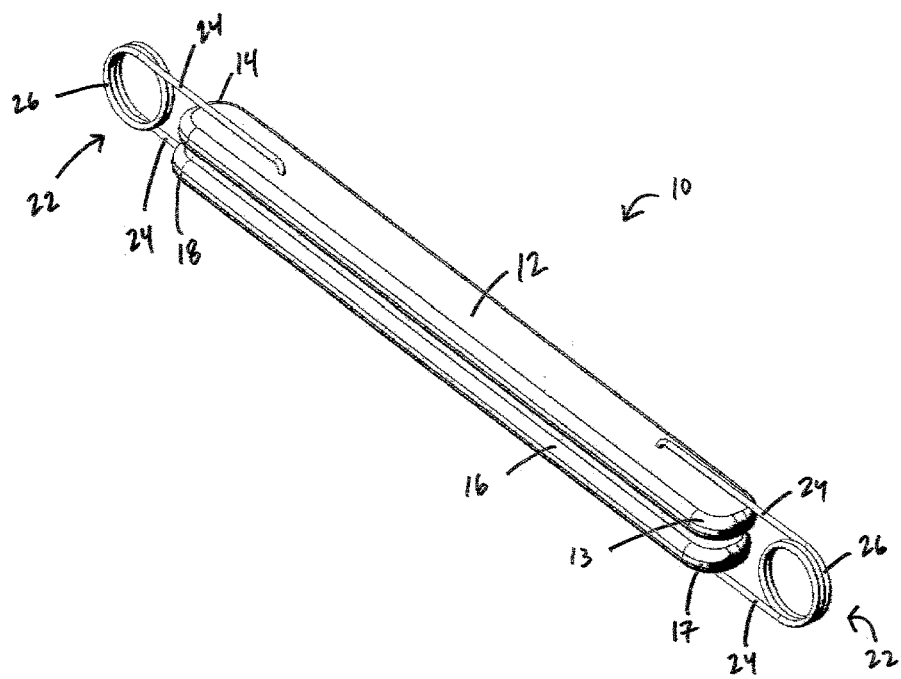
FIGS. 1 and 2 show perspective views of at least one embodiment of a restraining device for restoring and/or supporting a tissue or organ of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Figure 2:
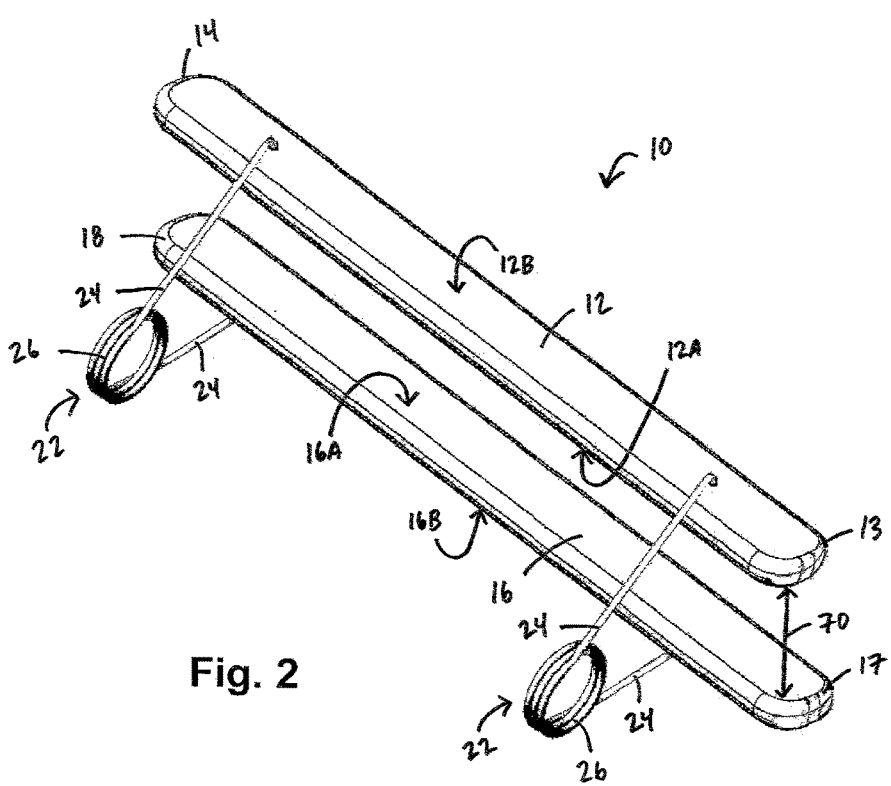

FIGS. 1 and 2 show perspective views of at least one embodiment of a restraining device 10 for restoring a tissue or organ. In at least one embodiment of the restraining device 10, the restraining device 10 comprises an implantable device and does not require substantial sutures, staples or pins to be secured on the targeted tissue or organ of interest. Further, the restraining device 10 described herein is configured to loosely, albeit securely, engage to the targeted tissue such that the underlying tissue is either uncompressed or only loosely compressed. The various embodiments of the restraining device 10 described herein may be available for temporary or chronic placement within a patient's body, and the restoration procedures performed through the use of an exemplary device 10 are reversible through minimally invasive procedures.

As shown in FIGS. 1 and 2, at least one embodiment of the restraining device 10 comprises a first engaging component 12 and a second engaging component 16. The first engaging component 12 may comprise a first shape and the second engaging component 16 may comprise a second shape that corresponds to at least a portion of the first shape of the first engaging component 12. For example, and without limitation, the first and second engaging components 12, 16 may be configured in a bar configuration as shown in FIGS. 1 and 2. Alternatively, the first and second engaging components 12, 16 may be configured in a contoured, circular or any other configuration suitable for use as referenced herein. Additionally, the first and second engaging components 12, 16 may be configured such that the shape of each of the components 12, 16 defines an interior area (not shown). It will be understood that the first and second engaging components 12, 16 of an exemplary restraining device 10 may be configured in any shape and may also be flexible, semi-flexible, or articulated. Furthermore, it is contemplated that a clinician may select the desired configuration of the components 12, 16 of the restraining device 10 based on the particular patient to be treated and/or pursuant to the specific application for which the restraining device 10 will be used to ensure that the restraining device 10 appropriately conforms to the tissue or organ of interest. For example, an exemplary embodiment of a restraining device 10 of the present disclosure may comprise first and second engaging components 12, 16 having a width of approximately 14 mm and a length of approximately 120 mm. In at least one additional embodiment, the first and second engaging components 12, 16 may have a width between 5 mm and 15 mm, and may have a length between 30 mm and 200 mm, with any number of potential widths and lengths contemplated by the present disclosure suitable for use with an exemplary restraining device 10 of the present disclosure.

In at least one embodiment of a restraining device 10 of the present disclosure, and as shown in FIG. 2, the first engaging component 12 of the restraining device 10 comprises a proximal end 13, a body having a first side 12A and a second side 12B, and a distal end 14. The first side 12A of the first engaging component 12 is configured to be positioned adjacent to or in contact with a tissue or organ of interest. Likewise, the second engaging component 16 comprises a proximal end 17, a body having a first side 16A and a second side 16B, and a distal end 18. The first side 16A of the second engaging component 16 is configured to be positioned adjacent to or in contact with the tissue or organ of interest.

The first engaging component 12 and the second engaging component 16 each comprise a material suitable to resist corrosion, such as and without limitation polyurethane, polyethylene, polytetrafluoroethylene ("PTFE"), nitinol, silastic, titanium, stainless steel or any other material suitable for use in the medical arts that is corrosion resistant. Accordingly, the restraining device 10 can withstand chronic placement within a body without the risk of deterioration. In at least one embodiment, the first and second engaging components 12, 16 of the restraining device 10 are comprised of ultra high density polyethylene.

Figure 7A:
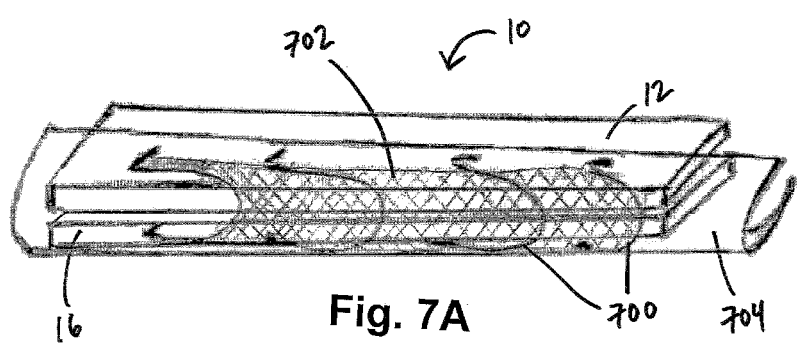
FIGS. 7A, 7B, and 8 show various embodiments of a restraining device comprising one or more struts according to the present disclosure.
Figure 7B:
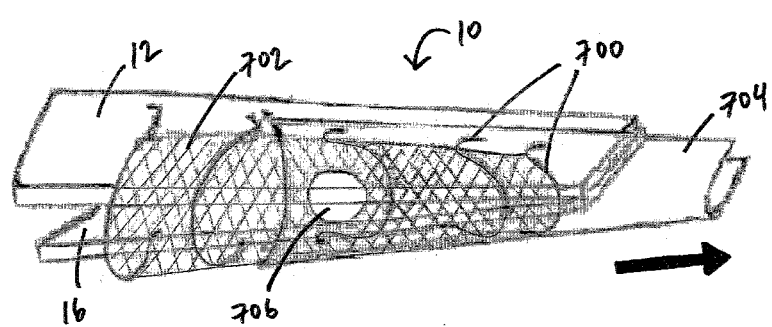

The first and second engaging components 12, 16 of the restraining device 10 may be coupled to one or more springs 22, wherein the one or more springs 22 engage the first and second engaging components 12, 16 at their distal ends 14, 18 and proximal ends 13, 17. Springs 22, as well as struts 700 (as shown in FIGS. 7A and 7B) and couplers 1200 (as shown in FIGS. 14A through 16B), as referenced herein, may be generally referred to as "connector(s)" as they connect, in various embodiments, first engaging components 12 and second engaging components 16 of various restraining devices 10 of the present disclosure. The springs 22 may comprise torsion springs or any other type of spring known or developed that is capable of supporting the first and second engaging components 12, 16 a prescribed distance apart from each other, which may vary depending upon the orientation of the springs 22 about the first and second engaging components 12, 16. As described in more detail herein, due to the configuration and resistance of the springs 22, the first and second engaging components 12, 16 of the restraining device may be held such that little or no space is defined between the first sides 12A, 16A of the first and second engaging components 12, 16 based upon a first orientation of springs 22, and the first and second engaging components 12, 16 of the restraining device 10 may be held such that an interior space 70 is defined between the first sides 12A, 16A of the first and second engaging components 12, 16 based upon a second orientation of springs 22.

Further, each of the one or more springs 22 may have any number of coils configured in any fashion, provided the spring configuration and stiffness are suitable for the desired application of the restraining device 10. For example, and without limitation, in at least one embodiment each of the one or more springs 22 comprises a torsion, resistance spring having three (3) closely-coiled coils. It will be appreciated that, in practice, a clinician may alter the number of coils and/or configuration of each spring 22 to achieve to a desired flexibility or rigidity of the springs 22 and, in this manner, the restraining device 10 may be customized for a particular patient and/or application for which the restraining device 10 is to be applied.

Each of the springs 22 of the restraining device 10 may comprise at least one rod 24 extending from each of the ends of its coils. The length of each rod 24 may be selected depending on the particular application for which the restraining device 10 is to be applied. As shown in the exemplary embodiments of a restraining device 10 in FIGS. 1 and 2, each rod 24 is coupled with either the first or second engaging component 12, 16. For example, as shown in FIG. 2, the first rod 24 of one of the springs 22 may be coupled with the second side 12B of the first engaging component 12 at or near a location on the distal end 14 of the first engaging component 12, and the second rod 24 of the same spring 22 may be coupled with the second side 16B of the second engaging component 16 at or near a location on the distal end 18 of the second engaging component 16. Furthermore, the rods 24 facilitate the formation of the interior space 70 (as shown in FIG. 2) between the first and second engaging components 12, 16 by holding the first and second engaging components 12, 16 in accordance with the tension of the springs 22.

The springs 22 of the restraining device 10 may comprise any dimensions so long as the restraining device 10 is of a sufficient size to move through a laparoscopic port and the springs 22 are capable of holding the first side 12A of the first engaging component 12 and the second side 16A of the second engaging component 16 a distance apart when the restraining device 10 has a configuration whereby the springs 22 are positioned about the first and second engaging components 12, 16. For example, springs 22 may have a "first" configuration as shown in FIG. 1, whereby springs 22 and the first and second engaging components 12, 16 are oriented in the same or substantially the same direction/plane so that the restraining device 10 may pass through a laparoscopic port. In such a first configuration, springs 22 engage the first and second engaging components 12, 16 so that the first and second engaging components 12, 16 either engage one another or have a relatively small space between them. Springs 22 may have a "second" configuration, for example and as shown in FIG. 2, when springs 22 are rotated about first and second engaging components 12, 16 and are not in the same direction/plane as the configuration of restraining device shown in FIG. 1. In such a second configuration, the first and second engaging components 12, 16 may define an interior space 70 when the restraining device 10 is "at rest," with the interior space 70 increasing upon positioning the restraining device 10 around a stomach 100 (as shown in FIGS. 4A through 5A) for example, and potentially increasing only slightly further upon introduction of food, for example, into the stomach 100.

Accordingly, the dimensions of the springs 22 may dictate the native value of the interior space 70 between the first and second engaging components 12, 16. In at least one embodiment, the springs 22 may comprise a maximum outside diameter that is less than about 14 millimeters to allow a "collapsed" or "compressed" restraining device 10 to pass within a 15 mm diameter abdominal port. Furthermore, each of the springs 22 may comprise any material having a strength that is consonant with the application for which the restraining device 10 will be employed. In at least one embodiment, the springs 22 are comprised of a rigid or semi-rigid material that is suitable to resist corrosion, such as and without limitation, polyurethane, PTFE, nitinol, silastic, titanium, stainless steel or any other material suitable for use in the medical arts that is corrosion resistant.

Referring back to FIG. 2, and as previously described, the springs 22 of the restraining device 10 are biased to maintain the first and second engaging components 12, 16 at a prescribed distance apart under a native, and as described above, "second" configuration. In this manner, when no pressure is applied to an exemplary restraining device 10—or when the restraining device 10 is "at rest"—the interior space 70 having a prescribed value is formed between the first and second engaging components 12, 16. The value of the interior space 70 may, in at least one embodiment, correlate with the outside diameter of the springs 22, minus the thickness of the first and second engaging components 12, 16. It will be understood that the value of the interior space 70 can be manipulated by a clinician depending on the thickness of tissue and/or organ to be treated or other factors. For example, to achieve an interior space 70 having a larger prescribed value, the outer diameter of the spring 22 may be increased and/or the thickness of the first and/or second engaging components 12, 16 may be adjusted. Accordingly, a clinician can easily modify the restraining device 10 such that it may be optimally configured for a particular application on a particular tissue.

Due to the nature of the springs 22 (depending on the material and rigidity selected), the first and second engaging components 12, 16 may exhibit some degree of "give" such that the first and second engaging components 12, 16 are capable of moving relative to each other when pressure is applied. While the first and second engaging components 12, 16 are biased to return to their resting position such that the interior space 70 is substantially equivalent to its prescribed/native value when no pressure is applied to the springs 22, the springs 22 of the restraining device 10 are also capable of allowing the first and second engaging components 12, 16 to move in response to force applied thereto. For example, and without limitation, if a force is applied against the first sides 12A, 16A of the first and second engaging components 12, 16, this force is translated to the springs 22 which enables the components 12, 16 of the restraining device 10 to move apart such that the interior space 70 is increased. Furthermore, if a force is applied directly to the springs 22 such that the coils are twisted about their axis in a direction counter to the coil configuration, similar to the above-listed example, the resultant effect on the restraining device 10 is that the first and second engaging components 12, 16 are moved apart and the interior space 70 is increased. However, due to the inherent bias provided by the springs 22 of the restraining device 10, after the pressure affecting the springs 22 is released, the springs 22—and thus the components 12, 16—return to their resting positions such that the interior space 70 reverts to its original prescribed value. It will be appreciated that the specific configuration and/or materials comprising each of the springs 22 may be selected to achieve the desired degree of elasticity depending on the application for which the restraining device 10 is to be applied.

As shown in FIG. 2, each rod 24 of spring 22 is rotatably coupled with the relevant component 12, 16 of the restraining device 10 such that each of the rods 24 is capable of pivotal movement with respect to the relevant component 12, 16 of the restraining device 10. The rotational coupling of the rods 24 with the first and second engaging components 12, 16 may be achieved through any means known in the art. For example and without limitation, the end of each rod 24 may comprise a pin that is capable of insertion into and rotation within a hole formed within the respective second side 12B, 16B of the applicable component 12, 16.

As each of the rods 24 is coupled with a spring 22, when the rods 24 rotate with respect to the components 12, 16, this effectively enables the respective spring 22 to move in an orbital manner with respect to the proximal or distal end of the restraining device 10. Accordingly, the springs 22 are capable of rotating between a position that is substantially parallel with the first and second engaging components 12, 16 (as shown in FIG. 1, referred to as a "first" configuration herein) and a position that is substantially perpendicular to the first and second engaging components 12, 16 (as shown in FIG. 2, referred to as a "second" configuration).

The position of the springs 22 relative to the first and second engaging components 12, 16 has the potential to significantly affect the overall width of the restraining device 10. For example and without limitation, when the springs 22 are positioned in the substantially perpendicular position (i.e., a "second" configuration), the restraining device 10 may have a width that is more than twice the width of the same restraining device 10 when its springs 22 are positioned in the substantially parallel position. Accordingly, the rotational coupling of the rods 24 with the first and second engaging components 12, 16 provides a clinician with the ability to manipulate the overall width of the restraining device 10 during laparoscopic delivery and/or implantation and further enables the restraining device 10 to be applied to tissues and/or organs having a length that is longer than the length of the restraining device 10 (as the proximal ends 13, 17 and the distal ends 14,18 of the first and second engaging components 12, 16 of the restraining device 10 are not obstructed by the springs 22). In at least one embodiment, the widest part of the restraining device 10 is less than about 15 millimeters when the springs 22 are in the substantially parallel position such that the restraining device 10 can be easily inserted into a body cavity through a 15 millimeter trocar or port.

Now referring to FIG. 3A, a top view of at least one embodiment of a restraining device 10 of the present disclosure is shown. Here, the first and/or second engaging components 12, 16 of the restraining device 10 further comprise one or more pads 30 extending therefrom. As shown in FIG. 3A, the one or more pads 30 may extend in a perpendicular fashion from the second side(s) 12B, 16B of the components 12, 16 and/or in a lateral fashion from the components 12, 16. Each of the pads 30 are comprised of a flexible material and configured to provide an anchor through which sutures or any other type of anchoring device may be inserted. For example, and in at least one embodiment, one or more pads 30 may be comprised of polyurethane or any other material that is capable of securely holding sutures or another type of anchoring device therein. One or more sutures may be placed within suture apertures 32 as shown in FIG. 3A, whereby said suture apertures 32 may be positioned along pads 30 and/or one or both of components 12, 16 as shown in FIG. 3A. Accordingly, after the first and second engaging components 12, 16 are properly positioned about a targeted tissue or organ, sutures may be inserted through suture apertures 32 and secured to a superficial layer of the underlying targeted tissue or organ to assist in anchoring the restraining device 10 in the proper location thereon.

FIGS. 3B-3E show various embodiments of first engaging component 12 and/or second engaging component 16 with various features to facilitate suturing and/or connection of first engaging component 12 to second engaging component 16. FIG. 3B shows an exemplary embodiment if a first and/or second engaging component 12, 16 comprising suture apertures 32 positioned therethrough. Suture apertures 32 are not limited to positioning near one or more of the ends of said first and/or second engaging component 12, 16, as such suture apertures 32 may be positioned along first and/or second engaging component 12, 16 as desired.

Figure 4A:
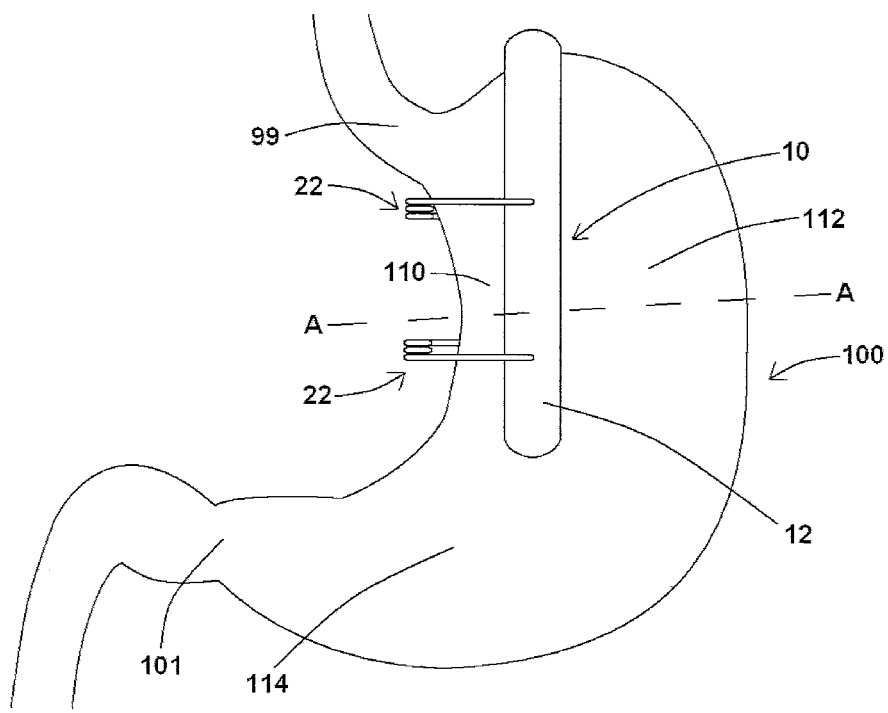
FIG. 4A shows a side view of the restraining device of FIGS. 1A and 1B applied in a longitudinal fashion to a stomach according to the present disclosure.
Figure 4B:
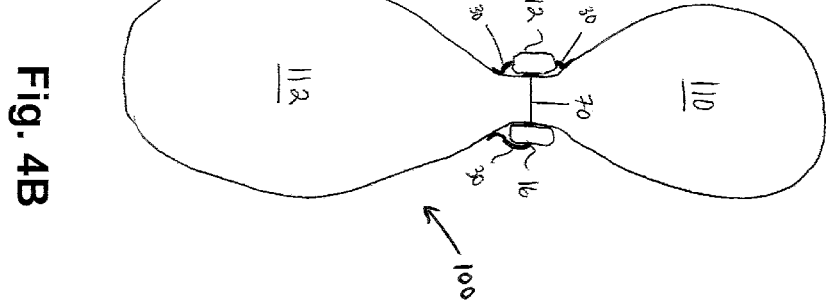
FIG. 4B shows a cross-sectional view of a restored stomach along line A-A of FIG. 4.

FIG. 3C shows an exemplary embodiment of a first and/or second engaging component 12, 16 comprising one or more strings 34 affixed thereto. In the exemplary embodiment shown in FIG. 3C, two strings 34 are shown at or near the ends of first and/or second engaging component 12, 16, noting, however, that one, two, or more strings 34 may be affixed thereto and positioned as desired. In an exemplary embodiment of a restraining device 10, and as shown in FIG. 4B, the first engaging component 12 and the second engaging component 16 may each comprise at least one string 34, whereby said strings 34 may be connected to one another to facilitate a desired placement of restraining device 10 about a stomach 100.

Additional embodiments of exemplary first and/or second engaging components 12, 16 are shown in FIGS. 3D and 3E. As shown in FIG. 3D, first and/or second engaging component 12, 16 comprises one or more suture members 36 affixed thereto, with said suture members defining an aperture to which a suture (not shown) or other restraining component may be affixed thereto. FIG. 3E shows an exemplary first and/or second engaging component 12, 16 of the present disclosure comprising pads 30 positioned at or near each end of the first and/or second engaging component 12, 16 with each pad 30 defining a suture aperture 32 therethrough. Additional embodiments of first and/or second engaging component 12, 16 comprising features to allow for a suture or other restraining component to be positioned therethrough are also contemplated by the present disclosure. For purposes of the present disclosure, the term "suturing elements" shall mean any number of elements for introducing a suture into the first and/or second engaging component 12, 16 and/or one or more pads 30 affixed thereto, including, but not limited to, one or more apertures 32, strings, 34, and/or suture members 36. In addition, any number of the features of the various exemplary first and/or second engaging components 12, 16 shown in FIGS. 3A-3E may appear in any number of embodiments of restraining devices 10 of the present disclosure.

In operation, the restraining device 10 may be applied to an organ or tissue of interest in order to restore the underlying tissue or organ into a desired configuration and/or provide support to the same. As discussed in further detail below, the restraining device 10 may be used for temporary or chronic implantation within a body without the risk of the first and second engaging components 12, 16 migrating through or damaging the underlying tissue. Furthermore, because the restraining device 10 does not require that the underlying tissue be punctured in any significant manner to achieve restoration and/or provide support thereto, implantation of the restraining device 10 is entirely reversible and, if desired, the restraining device 10 may be easily removed from the organ or tissue of interest through a laparoscopic procedure.

As previously described, the specifications of the restraining device 10 may be modified to achieve a desired result. For example, and without limitation, the dimensions of the components 12, 16 and/or the springs 22 may be chosen for a particular application and/or based on the patient. Accordingly, while certain embodiments of the restraining device 10 may be described in connection with particular tissues or organs, it will be appreciated that any of the embodiments of the restraining device 10 described herein may also be applied to any tissue or organ of interest in a similar manner and use of the particular embodiments of the restraining device 10 in lieu of others may be determined based on the patient's specifications, the specific application, and/or the tissue or organ in question.

In practice, an exemplary restraining device 10 is capable of restoring and/or supporting an underlying tissue while avoiding constriction and the excessive compression thereof. For example, the restraining device 10 may be applied to a stomach 100 as shown in FIGS. 4A and 4B. In at least one embodiment, and as shown in FIG. 4A, the springs 22 of the restraining device 10 are rotated to the substantially perpendicular position such that the interior space 70 is increased between the first and second engaging components 12, 16. Thereafter, the restraining device 10 may be advanced over the stomach 100 such that, for example, the first side 12A of the first engaging component 12 is positioned adjacent to the anterior wall of the stomach 100 and the first side 16A of the second bar 16 is positioned adjacent to the posterior wall of the stomach 100. While the restraining device 10 is shown in FIG. 4A in a longitudinal placement with respect to the stomach 100, it will be understood that the restraining device 10 may alternatively be positioned in a horizontal configuration or an angular configuration with respect to the stomach 100.

After the first and second engaging components 12, 16 are positioned in the desired location with respect to the stomach 100, the overall interior space 70 may either comprise its original native interior space 70 or a relatively larger interior space 70 due to the positioning of the restraining device 10 about the stomach 100. Therefore, various embodiments of restraining device 10 do not operate to "clamp" the stomach 100 or any other tissue or organ, as restraining device 10 merely operates, when positioned around a stomach 100, to provide a limited pressure, if any, to maintain a native size/shape of at least a portion of the stomach 100. For example, and depending upon the prescribed value of the interior space 70 as desired by a clinician, the configuration of the springs 22 can be modified to achieve a restraining device 10 that either does not compress, or only loosely compresses, the sandwiched tissue between the first and second engaging components 12, 16. In a preferred embodiment, restraining device 10, when positioned about a stomach 100, does not provide any meaningful compressive pressure upon the stomach 100, and may be held in place, for example, using one or more sutures as referenced herein. In this manner, the restraining device 10 can be employed to reversibly restore an organ or tissue without forming adhesions thereon and/or permanently restoring the same.

In at least one embodiment, and depending on the configuration of the springs 22, the springs 22 may exhibit enough elasticity to enable the first and second engaging components 12, 16 to move to some degree in conjunction with any movement of a tissue or organ positioned between the first and second engaging components 12, 16 of the restraining device 10. In this manner, the springs 22 can allow, for example, the restraining device 10 to accommodate any inherent movement in the stomach 100 such that application of the restraining device 10 does not completely inhibit the normal digestive function of the same. For example, the introduction of food into the stomach 100 may cause the outer dimensions of the stomach 100 to expand, whereby stomach 100 exerts a pressure upon restraining device 100. Furthermore, the restraining device's 10 ability to accommodate any inherent movement in the underlying organ and/or tissue increases the likelihood that the restraining device 10 will remain in its desired location on the tissue and/or organ without sheering off or sliding therefrom.

In the event it is desired that the restraining device 10 is further secured to the underlying tissue, and as previously referenced herein, a clinician can employ sutures to assist with the secure implantation of the restraining device 10 in the desired location. In the at least one embodiment of the restraining device 10 comprising the one or more pads 30, a clinician can secure the one or more pads 30 of the first and second engaging components 12, 16 to the underlying tissue through the use of superficial sutures. In this manner, the superficial sutures can be affixed through the one or more pads 30 and the surface of the underlying tissue such that the one or more pads 30 assist with anchoring the restraining device 10 in position on the tissue of interest. Conversely, and in at least one embodiment, sutures may be introduced directly to the first and/or second engaging components 12, 16 to secure a restraining device to a tissue or organ of interest as shown in FIGS. 3A-3E.

Figure 5A:
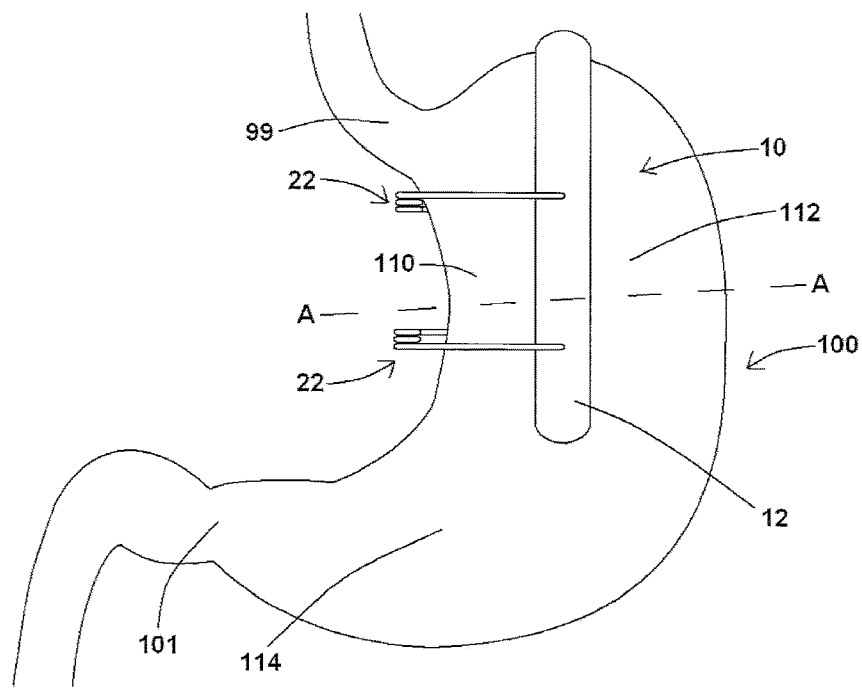
FIGS. 5A through 5D show various embodiments of restraining devices positioned about a stomach according to the present disclosure.

FIG. 4B shows a cross-sectional view of the stomach 100 of FIG. 4A taken along A-A. As shown in FIG. 4B, when the first and second engaging components 12, 16 of the restraining device 10 are longitudinally positioned on the stomach 100, the stomach 100 is "divided" into two portions—a first stomach portion 110 and a second stomach portion 112 as shown in FIGS. 4A and 4B. In the embodiment shown in FIGS. 4A and 4B, the first stomach portion 110 is relatively smaller than the second stomach portion 112. However, and as shown in FIG. 5A, the first stomach portion 110 and the second stomach portion 112 may be approximately the same size.

As the first stomach portion 110 receives ingested matter directly from the gastroesophageal junction 99 as shown in FIG. 4A, the placement of the restraining device 10 as shown in FIG. 4B thus inhibits the majority of ingested matter from moving into the second stomach portion 112. Instead, and in at least one embodiment, such ingested matter is directed through the smaller, first stomach portion 110 and into the pyloric canal 101 (as shown in FIG. 4A) where a significant portion of the ingested matter is evacuated from the stomach 100. Due to the size of the first stomach portion 110, the amount of food that the patient can consume at one time is significantly reduced and satiety is more quickly achieved.

While the delineation formed by the restraining device 10 between the first stomach portion 110 and the second stomach portion 112 is not leak-proof, the interior space 70 created between the first and second engaging components 12, 16 comprises an area that is less than the diameter of a fully extended stomach 100 (as shown in FIG. 4B). Accordingly, when the restraining device 10 is applied in a longitudinal fashion to a stomach 100, restraining device 10 provides support to the anterior and posterior walls of the stomach 100, with the expansion of stomach 100 exerting a force onto the first and second engaging components 12, 16 of restraining device 10, this preventing stomach 100 distension in that area. In this manner, most of the food matter received into the first stomach portion 110 through the gastroesophageal junction 99 is maintained therein and the patient exhibits the sensation of satiety earlier.

Referring back to FIG. 4A, and in at least one exemplary embodiment, because the restraining device 10 does not extend along the entire length of the stomach 100, an outflow tract 114 is formed caudally of the restraining device 10. This outflow tract 114 allows the portion of ingested matter that flows from the gastroesophageal junction 99 into the second stomach portion 112 to be evacuated from the stomach 100 in a controlled manner and to proceed through normal digestion. In addition, the outflow tract 114 allows any food matter or enzymes residing within the second stomach portion 112 to evacuate the stomach 100.

Figure 5B:
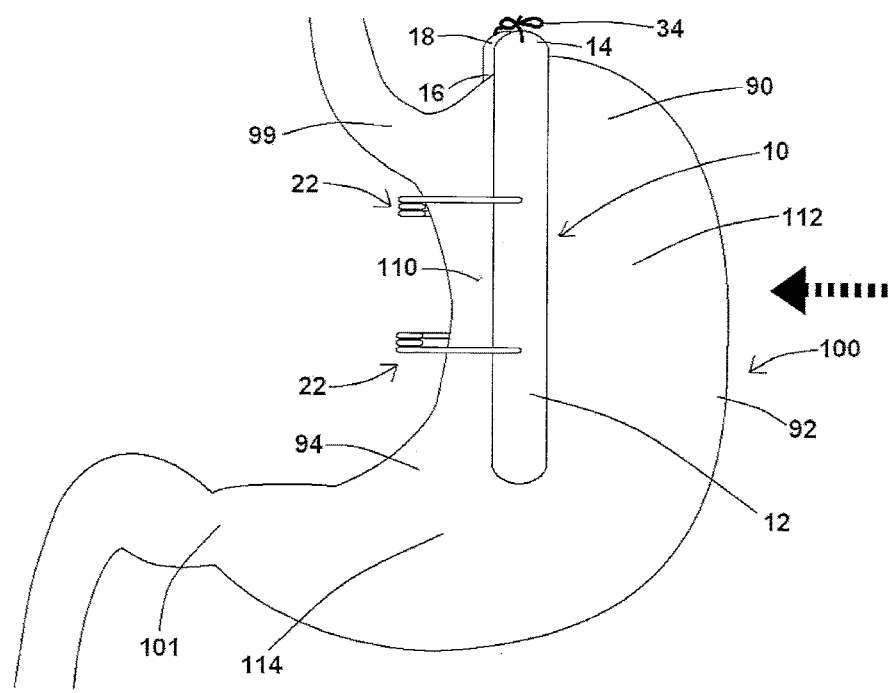
Figure 5C:
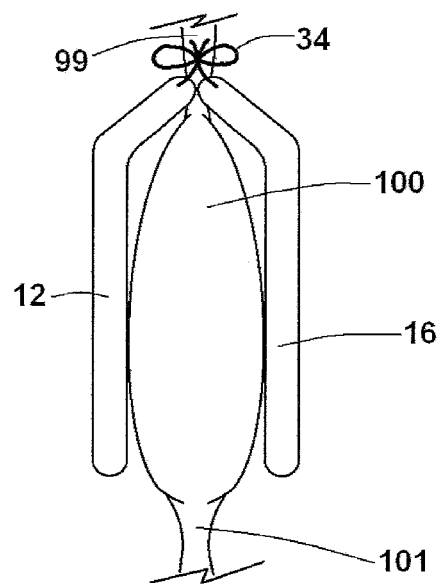

Additional embodiments of restraining devices 10 of the disclosure of the present application positioned about a stomach 100 are shown in FIGS. 5B and 5C. In the exemplary embodiment shown in FIG. 5B, restraining device 10 comprises first and second engaging components 12, 16 which are "longer" than those shown in FIG. 5A, whereby distal end 14 of first engaging component 12 and distal end 18 of second engaging component 16 extend past stomach 100. In this exemplary embodiment, strings 34 affixed to first and second engaging components 12, 16 may be connected/tied to each other after restraining device 10 has been positioned about a stomach, maintaining restraining device 10 in place.

FIG. 5C shows restraining device 10 positioned about stomach 100 viewed in the direction of the arrow shown in FIG. 5B. As shown in FIG. 5B, the tying/coupling together of strings 34 at the distal ends 14, 18 of first and second engaging components 12, 16 may cause portions of the first and second engaging components 12, 16 to angle towards one another as shown in FIG. 5C. In this particular embodiment, first and second engaging components 12, 16 are flexible or semi-flexible, and the positioning of restraining device 10 about stomach 100 serves to isolate the first stomach portion 110 from fundus 90 and greater curvature 92. This "funnel" effect, in addition to the embodiment of a restraining device 10 shown in FIG. 5D below, may also be accomplished by having springs 22 with relatively shorter rods 24 (or relatively smaller struts 700 as referenced in various embodiments herein) at one end of restraining device 10, and by having springs 22 with relatively longer rods 24 (or relatively larger struts 700 as referenced in various embodiments herein) at the other end of restraining device 10. In addition as to being substantially rigid as shown in FIGS. 1 and 2, and as shown in FIG. 5C, first and second engaging components 12, 16 may have substantially rigid center portions and one or more flexible or semi-flexible ends, or first and second engaging components 12, 16 may be flexible or semi-flexible along the entirety of said components 12, 16.

Figure 5D:
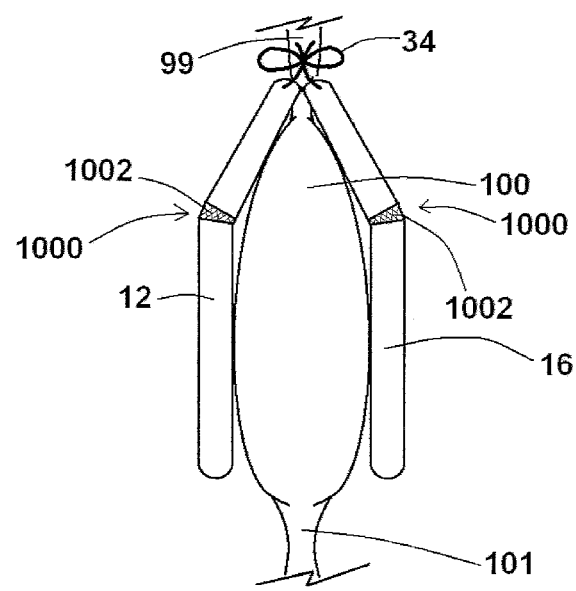

An additional embodiment of a restraining device 10 of the present disclosure positioned about stomach 100 is shown in FIG. 5D. As shown in FIG. 5D, and as also discussed herein regarding FIG. 10, restraining device 10 further comprises a pliable junction 1000 positioned within the first engaging component 12 and second engaging component 16, effectively "splitting" each component, whereby each "split" component is connected to one another by way of a flexible structure 1002. As shown in FIG. 5D, flexible structure 1002 may comprise a PTFE band or a PTFE mesh, for example, whereby any potential embodiment of flexible structure 1002, using one or more pliable materials disclosed herein or otherwise known in the art, allows the relatively or fully rigid first engaging component 12 and second engaging component 16 to better fit the stomach, allowing the patient, for example, to bend the stomach when restraining device 10 is positioned thereon.

Approximating first and second engaging components 12, 16, as shown in FIGS. 5B, 5C, and 5D, and as identified during internal testing of exemplary restraining devices 10 of the present disclosure, leads to reduced food intake (65-70% of normal food intake) as compared to positioning restraining device 10 about stomach 100 without approximating first and second engaging components 12, 16 toward one another as shown in FIG. 4A (80-85% of normal food intake). This approximation also assists with the prevention of a fistula so that the food may move down the pouch (first stomach portion 110) along antrum 94 as opposed to shunted to the fundus 90 of stomach 100.

As described herein, application of the restraining device 10 allows a clinician to restore a targeted tissue, such as a stomach 100, while avoiding constriction and excessive compression of the same. Further, the various embodiments described herein allow a clinician to tailor the restraining device 10 to multiple restoration applications and various different types of tissues. Permanent restoration of the tissue is avoided, which prevents adhesions from developing in the underlying targeted tissue and allow for the complete reversal of the restoration procedure. Additionally, the restraining device 10 is simple to deliver and, as such, the device 10 may be used in conjunction with other techniques or surgical procedures.

Regarding the application of the restraining device 10 to the stomach 100, use of the restraining device 10 in the treatment of obesity avoids the nutritional and metabolic deficiencies observed after Malabsorptive Procedures because the digestive process may continue within the stomach as with a native stomach 100. In addition, the restraining device 10 does not require more than superficial punctures to the underlying tissue, nor does it employ pins, staples or significant sutures which may lead to dehiscence or fistula formation, or produce the degree of regurgitation and vomiting observed in connection with conventional methods used to treat obesity. Moreover, each of the embodiments described herein may be inserted into the body cavity laparoscopically, thereby decreasing the patient's stress associated with the procedure and the patient's recovery time. It will be recognized that any of the devices described herein may be employed in combination with other conventional bariatric procedures.

Figure 6:
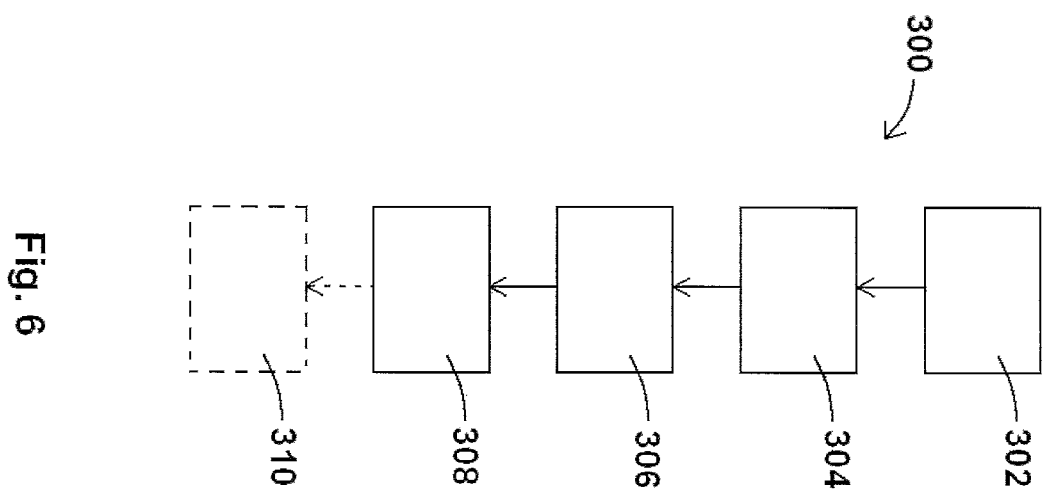
FIG. 6 shows a flow chart of a method for laparoscopically delivering embodiments of the restraining device disclosed herein to a targeted tissue according to the present disclosure.

Now referring to FIG. 6, a flow chart of a method 300 for laparoscopically delivering the restraining device 10 is shown. For ease of understanding, the steps of the related methods described herein will be discussed relative to the components of an exemplary restraining device 10. Furthermore, while the methods described herein are described in connection with embodiments of the restraining device 10 and an exemplary delivery device, it will be appreciated that various additional devices may be used to facilitate the laparoscopic delivery of the restraining device 10 such as a camera, light and/or a device for delivering a gas to a targeted area.

At step 302, the first and second engaging components 12, 16 of restraining device 10 are advanced laparoscopically into the patient's body. In at least one embodiment, the restraining device 10 may be inserted through a 15 millimeter cannula under insufflation into the appropriate cavity of the patient's body. This may be achieved through use of an exemplary delivery device known in the art. At this step 302, the springs 22 of the restraining device 10 are positioned in the substantially parallel position such that the overall diameter of the restraining device 10 is sufficiently narrow for insertion into the body.

At step 304 the restraining device 10 is advanced to a location adjacent to a targeted tissue. In the at least one embodiment of the method 300 where an exemplary delivery device is employed to facilitate delivery of the restraining device 10 to the targeted tissue, at step 304 the restraining device 10 is advanced out of the delivery device and into the body cavity. After the restraining device 10 is no longer positioned within an exemplary delivery device, the delivery device may be withdrawn from the body cavity at this step 304 or as desired by the clinician.

At step 306, the springs 22 of the restraining device 10 are rotated from the substantially parallel position to the substantially perpendicular position, separating the first and second engaging components 12, 16 from one another to a native interior space 70. Step 306 may be performed using any number of standard laparoscopic tools known in the art useful to pull and grasp portions of a tissue or a device. In this manner, neither the proximal ends 13, 17 nor distal ends 14, 18 of the first and second engaging components 12, 16 of the restraining device 10 are blocked by the springs 22 and/or rods 24, and the first and second engaging components 12, 16 may be advanced over a targeted tissue having a length that is greater than the overall length of the first and second engaging components 12, 16.

At step 308, under fluoroscopic, direct camera control or otherwise, the restraining device 10 is advanced over the targeted tissue. In at least one embodiment, and at step 308, the first side 12A of the first engaging component 12 is positioned adjacent to the desired surface of the targeted tissue and the first side 16A of the second engaging component 16 is positioned adjacent to an opposite side of the targeted tissue. As the first and second engaging components 12, 16 of the restraining device 10 are positioned adjacent to opposite sides of the targeted tissue, at this step 308 the targeted tissue is positioned within the interior space 70 formed between the first and second engaging components 12, 16. Accordingly, while the targeted tissue may experience some compressional force exerted by the first and second engaging components 12, 16 of the restraining device 10, the majority of the pressure upon the first and second engaging components 12, 16 is provided by distension/expansion of the targeted tissue (for example, expansion of a stomach 100 when food is introduced therein). Further, due to the configuration and composition of the restraining device 10, the restraining device 10 can remain within the patient's body for as long as the restoration or support treatment delivered thereby is desired.

If preferred, in at least one embodiment of the restraining device 10 that further comprises one or more pads 30 coupled with the first and/or second engaging components 12, 16, the method 300 may advance from step 308 to step 310. At step 310, a clinician can employ sutures to further anchor and secure the restraining device 10 in the desired position on the targeted tissue. These sutures need only superficially puncture the underlying tissue and therefore are not associated with the negative effects associated with suturing, stapling and/or the insertion of pins used in conventional methods.

Additional embodiments of restraining devices 10 of the disclosure of the present application is shown in FIGS. 7A and 7B. As shown in FIGS. 7A and 7B, restraining device 10 comprises a first engaging component 12 and a second engaging component 16, whereby the first engaging component 12 and second engaging component 16 are coupled to one another by way of one or more struts 700. In the exemplary embodiment shown in FIGS. 7A and 7B, four struts 700 and five struts 700 are used, respectively, but any number of struts 700 may be used as desired for a particular application. Struts 700 may comprise any number of suitable materials as otherwise described herein, including, but not limited to, nitinol and stainless steel. Struts 700, in an exemplary application, would have a pre-established "open" size and a pre-established "strength", so that restraining device, in a native "rest" configuration, would be "open" (by way of, for example, the "memory" of struts 700) and would require some sort of pressure/force to open even further. The "open" configuration would keep first engaging component 12 and second engaging component 16 a fixed distance apart to avoid gastric tissue compression when positioned about a stomach.

An exemplary restraining device 10 may further comprise a mesh curtain 702 coupled to struts 700 as shown in FIGS. 7A and 7B. Mesh curtain 702 may prevent or limit potential organ distension or remodeling when restraining device 10 is positioned about an organ of interest. A demi shaft 704, as shown in FIGS. 7A and 7B, may be positioned around at least part of struts 700 and/or mesh curtain 702 to facilitate insertion of restraining device 10 within a body. For example, and as shown in FIG. 7A, restraining device 10 may be seen as inserted within a body, noting that restraining device is somewhat compressed by demi shaft 704, to facilitate insertion through, for example, a laparoscopic port. After insertion, and as shown in FIG. 7B, demi shaft 704 may be withdrawn in the direction of the arrow (shown as partially withdrawn in the figure) to allow restraining device 10 to obtain its original, uncompressed configuration, and ultimately removed from the body. Struts 702 may have a first configuration when positioned within demi shaft 704, as shown in FIG. 7A, and may have a second configuration when demi shaft 704 is removed, as shown on the left side of FIG. 7B.

Figure 8:
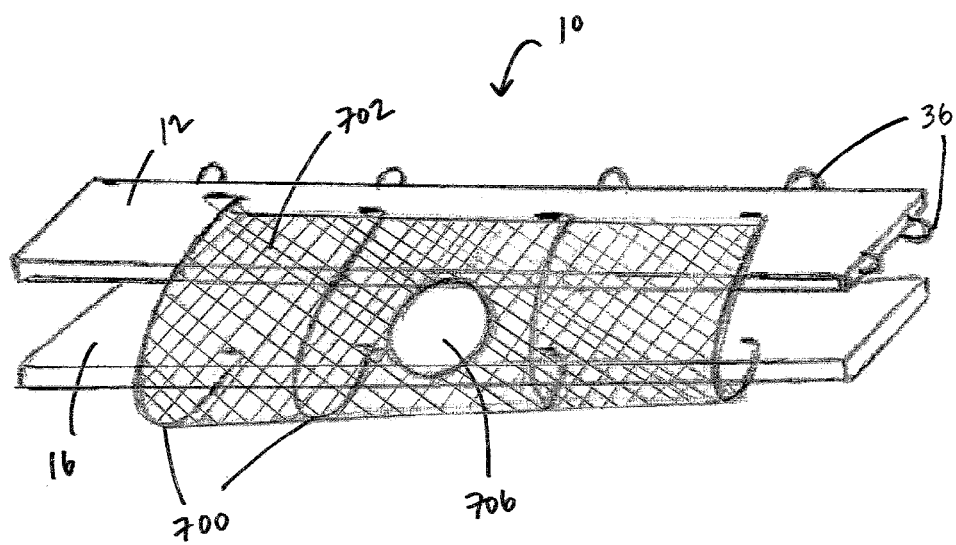

When restraining device 10 is in its native configuration, it may then be positioned about a stomach, for example, and the user positioning restraining device 10 may grasp stomach tissue using any number of laparoscopic tools through mesh aperture 706 as shown in FIGS. 7B and 8. As shown in FIG. 8, an exemplary restraining device 10 may also comprise one or more suture members 36 to allow one or more sutures (not shown) to be used to secure restraining device 10 to, for example, an anterior gastric wall.

Figure 9:
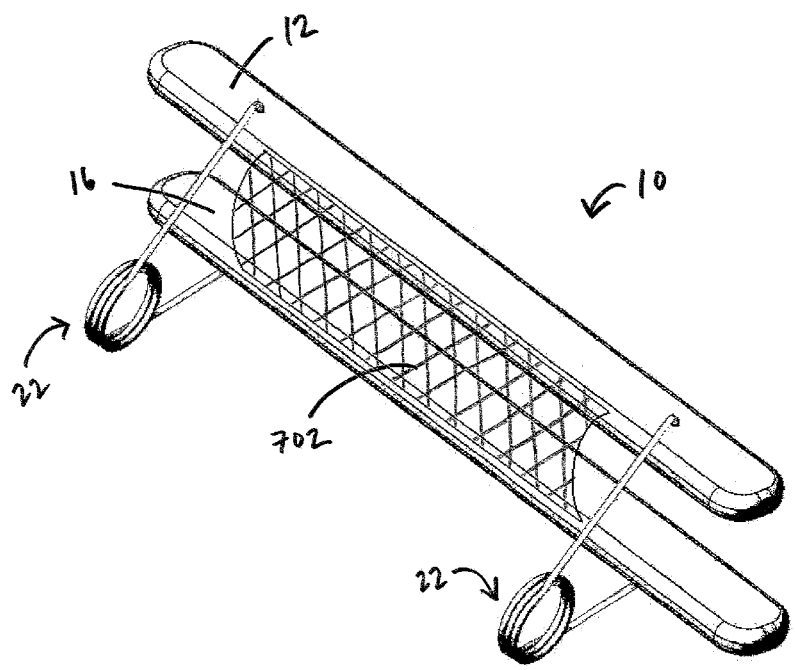
FIG. 9 shows an exemplary embodiment of a restraining device comprising two springs and a mesh curtain according to the present disclosure.

An additional embodiment of a restraining device 10 of the disclosure of the present application is shown in FIG. 9. As shown in FIG. 9, restraining device 10 comprises a first engaging component 12 and a second engaging component 16, whereby first engaging component 12 and second engaging component 16 are coupled to one another by way of one or more springs 22. In this exemplary embodiment, restraining device 10 further comprises a mesh curtain 702 coupled to first engaging component 12 and second engaging component 16, whereby mesh curtain 702 may prevent or reduce organ distension or remodeling when restraining device 10 is positioned about an organ. The flexibility/pliability of mesh curtain 702 would allow mesh curtain 702 to be closely positioned first engaging component 12 and second engaging component 16 upon insertion of restraining device 10 within a body, and may further allow mesh curtain 702 to expand in a direction of springs 22 as shown in FIG. 9, for example, to prevent organ distention.

Figure 10:
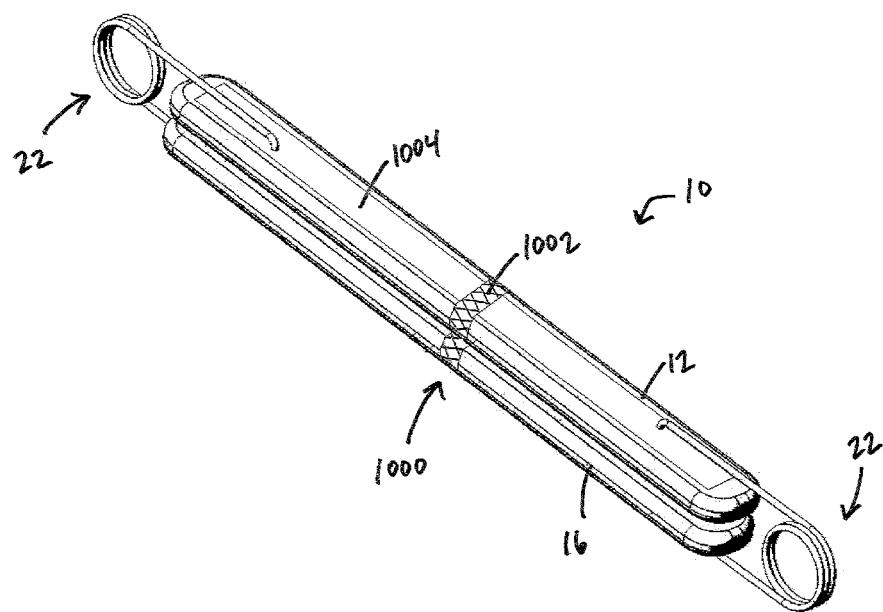
FIG. 10 shows an exemplary embodiment of a restraining device comprising a pliable junction according to the present disclosure.

FIG. 10 shows yet another embodiment of a restraining device 10 of the present application. As shown in FIG. 10, restraining device comprises a first engaging component 12 and a second engaging component 16, whereby first engaging component 12 and second engaging component 16 are coupled to one another by way of one or more springs 22. However, in this exemplary embodiment, restraining device 10 further comprises a pliable junction 1000 positioned within the first engaging component 12 and second engaging component 16, effectively "splitting" each component, whereby each "split" component is connected to one another by way of a flexible structure 1002. As shown in FIG. 10, flexible structure 1002 may comprise a PTFE band or a PTFE mesh, for example, whereby any potential embodiment of flexible structure 1002, using one or more pliable materials disclosed herein or otherwise known in the art, allows the relatively or fully rigid first engaging component 12 and second engaging component 16 to better fit the stomach, allowing the patient, for example, to bend the stomach when restraining device 10 is positioned thereon. In addition, and as shown in the exemplary embodiment in FIG. 10, restraining device 10 may further comprise a tissue cover 1004 positioned either partially or fully around either or both of first engaging component 12 and second engaging component 16.

Figure 11:
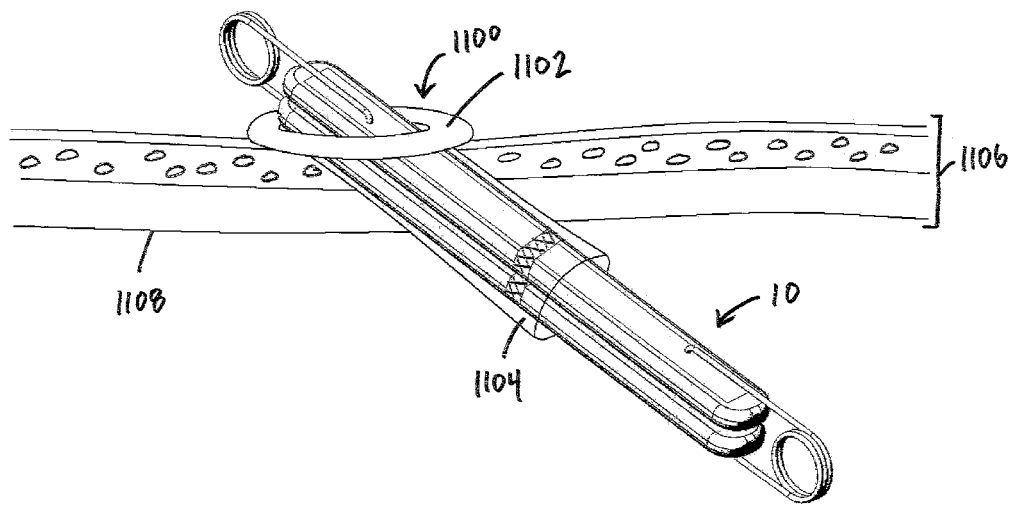
FIG. 11 shows a restraining device positioned within a laparoscopic port according to the present disclosure.

FIG. 11 shows an exemplary embodiment of a restraining device 10 of the present application positioned within a laparoscopic port. As shown in FIG. 11, restraining device 10 is shown as being inserted into a body portion by way of laparoscopic port 1100, with the exemplary laparoscopic port 1100 shown as comprising a ring 1102 and a port sleeve 1104 to facilitate introduction of restraining device 10 through an abdominal wall 1106. Viewing the figure from the outside-in, restraining device 10 is shown as being introduced into an abdomen through abdominal wall 1106, with peritoneum 1108 shown as being an innermost layer of the abdominal wall.

Figure 12A:
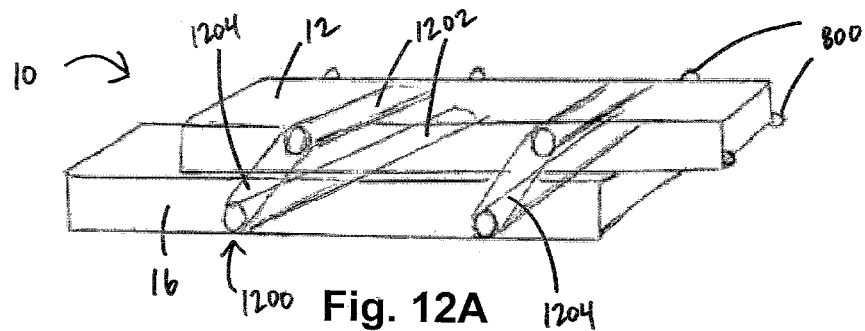
FIGS. 12A, 12B, 13A, and 13B show various embodiments of a restraining device comprising a coupler according to the present disclosure.

An additional embodiment of a restraining device 10 of the disclosure of the present application is shown in FIG. 12A. As shown in FIG. 12A, restraining device 10 comprises a first engaging component 12 and a second engaging component 16, whereby first engaging component 12 and second engaging component 16 are coupled to one another by way of one or more couplers 1200. In this exemplary embodiment, restraining device comprises two couplers 1200, shown in further detail in FIG. 12B. Couplers 1200 may comprise coupler arms 1202 connected to one another by way of a coupler bar 1204, and may comprise any number of suitable materials as described herein for various components of the present disclosure. As shown in FIG. 12A, coupler arms 1202 may be positioned within first engaging component 12 and second engaging component 16 by way of apertures 1210 (as shown in FIG. 12B) defined therein, allowing first engaging component 12 and second engaging component 16 to move relative to one another as couplers 1200 swivel when positioned at least partially within said apertures 1210.

Figure 12B:
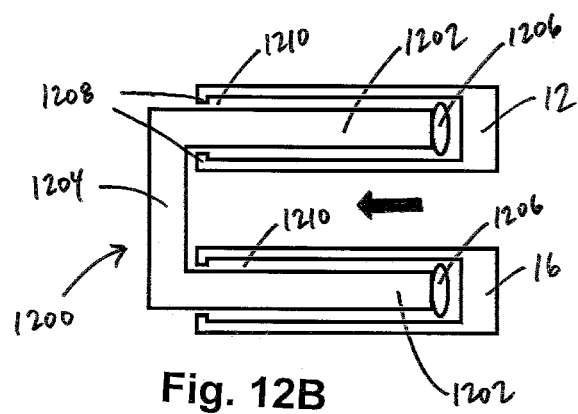

As shown in FIG. 12B, an exemplary embodiment of a coupler 1200 may comprise a coupler protrusion 1206 at or near the end of each coupler arm 1202, whereby coupler protrusions either prevent or restrict the removal of coupler 1200 from the either first engaging component 12 or the second engaging component 16 by way of stops 1208 positioned about the first engaging component 12 and the second engaging component 16 at or near the apertures 1210 defined therein. As coupler 1200 moves in the direction of the arrow shown in FIG. 12B, coupler protrusions 1206 would engage stops 1208, thus preventing or restricting the removal of coupler 1200 from the first engaging component 12 and/or the second engaging component 16.

Figure 13A:
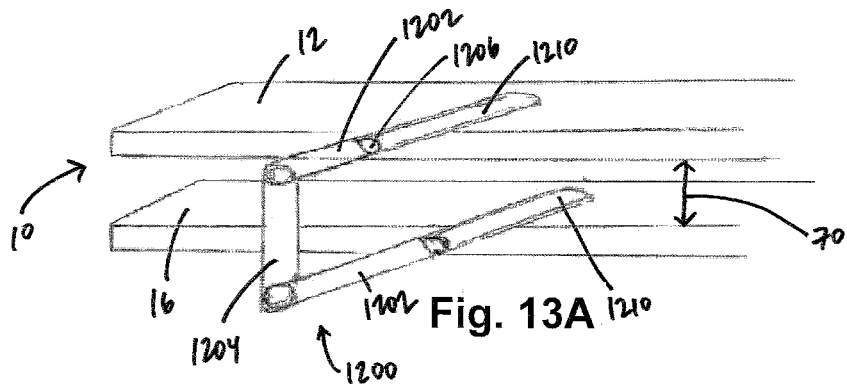
Figure 13B:
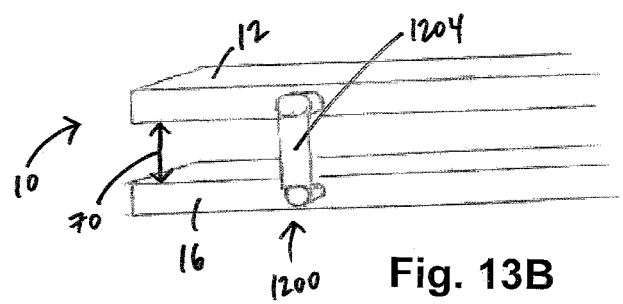

Insertion of the exemplary embodiment of the restraining device 10 shown in FIG. 12A into a body portion may be performed by inserting said restraining device 10 through a laparoscopic port with first engaging component 12 and second engaging component 16 either touching or nearly touching one another, and with couplers 1200 either mostly or fully inserted within apertures 1210 of restraining device 10. When restraining device has been inserted into a body portion, first engaging component 12 and second engaging component 16 may be separated a pre-established distance from one another my way of turning/swiveling couplers 1200. As such, couplers 1200, as well as first engaging component 12 and second engaging component 16, may be sized and shaped as desired for a particular application, FIGS. 13A and 13B show an exemplary embodiment of a restraining device 10 with a coupler 1200 positioned therein in a configuration to maximize the interior space 70 between first engaging component 12 and second engaging component 16. As such, the configuration of coupler 1200 shown in FIG. 12A may be viewed as "closed," while the configuration shown in FIG. 13A may be viewed as "open." In addition, and as described above and shown in FIG. 13A, coupler 1200 may be withdrawn from apertures of first engaging component 12 and second engaging component 16 to facilitate placement of restraining device about an organ of interest, Such withdrawal may be performed using any number of laparoscopic tools, for example, whereby coupler 1200 is withdrawn up to a point where protrusions 1206 would engage stops 1208 as shown in FIG. 12B.

Figure 14A:
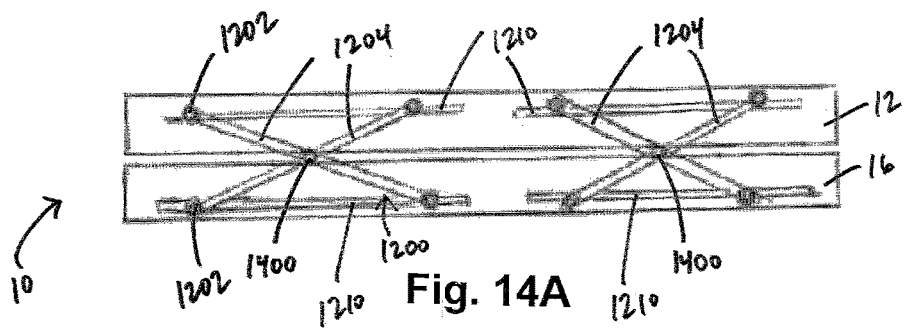
FIGS. 14A and 14B show exemplary embodiments of a restraining device comprising a coupler and a coupler pivot according to the present disclosure.
Figure 14B:
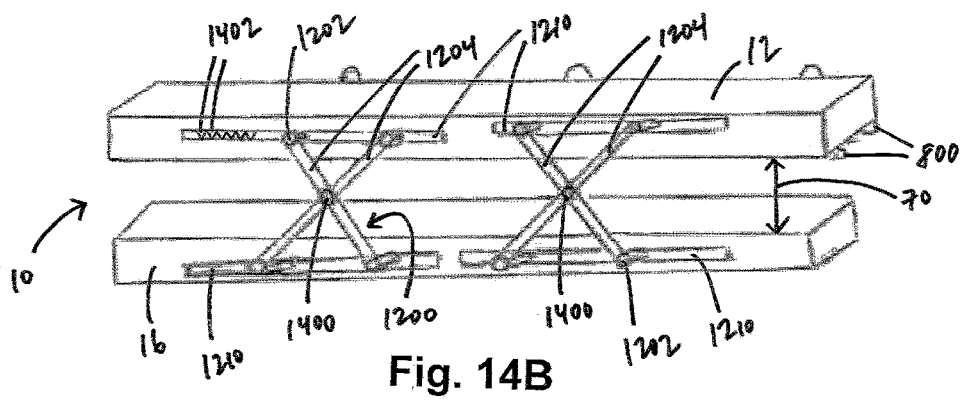

Another exemplary embodiment of a restraining device 10 of the disclosure of the present application is shown in FIGS. 14A and 14B. As shown in FIGS. 14A and 14B, restraining device 10 comprises a first engaging component 12 and a second engaging component 16, whereby first engaging component 12 and second engaging component 16 are coupled to one another by way of one or more couplers 1200. In the embodiments shown in FIGS. 14A and 14B, couplers 1200 comprise "scissor" couplers 1200, whereby at least two coupler bars 1204 are connected to one another via a pivot member 1400 so that coupler bars 1204 may pivot about one another at pivot member 1400. As coupler 1200 shifts from a "closed" configuration, as shown in FIG. 14A, to an "open" configuration, as shown in FIG. 14B, coupler bars 1204 pivot about pivot member 1400 causing coupler bars 1204 to move closer to one another in a direction opposite the direction of the length of first engaging component 12 and second engaging component 16.

Couplers 1200, as shown in FIGS. 14A and 14B, may "open" and "close" by way of movement of coupler arms 1202 (ends shown in the two figures) within apertures 1210 defined within first engaging component 12 and second engaging component 16. Apertures 1210, as shown in these exemplary embodiments, are configured as horizontal grooves to allow coupler arms 1202 to move closer to one another within the same aperture 1210 while coupler 1200 is "opening" and to allow coupler arms 1202 to move away from one another within the same aperture 1210 while coupler 1200 is "closing." As shown in FIG. 14B, restraining device 10, in a fully open position, would maximize the interior space 70 between first engaging component 12 and second engaging component 16. Protrusions 1402, such as teeth, indentations, and the like, may be positioned at or near apertures 1210, as shown in FIG. 14B, to facilitate fixation of coupler arms 1202 in a desired position, allowing a user positioning restraining device 10 within a body to measure the exact the interior space 70 between first engaging component 12 and second engaging component 16.

Upon insertion of the exemplary embodiment of restraining device 10 shown in FIGS. 14A and 14B within an abdominal cavity (through a laparoscopic port, for example), any number of laparoscopic tools may be used to grasp couplers 1200 to withdraw them from first engaging component 12 and second engaging component 16 as referenced herein regarding various other embodiments of restraining devices 10.

Figure 15B:
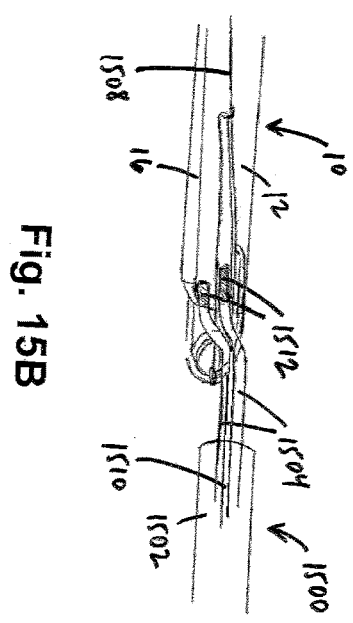
FIGS. 15A and 15B show exemplary embodiments of an apparatus for delivering a restraining device according to the present disclosure.
Figure 15A:
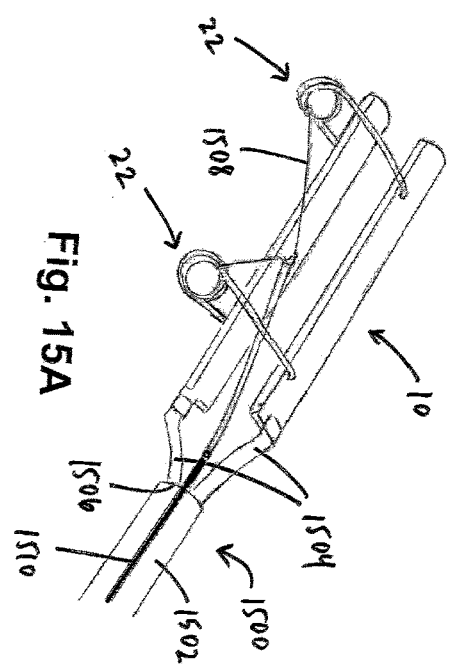

An exemplary delivery apparatus for delivering a restraining device 10 of the present application is shown in FIGS. 15A and 15B. As shown in FIG. 15A, an exemplary delivery apparatus 1500 comprises a shaft 1502 and arms 1504 at or near a distal end 1506 of shaft 1502. Apparatus 1500 may further comprise string 1508, whereby string 1508 may either be coupled to or engaged by a pull bar 1510 (an exemplary "puller" of the present disclosure) positioned within the lumen of apparatus 1500. Arms 1504 may engage an outer surface of first engaging component 12 and second engaging component 16, a protrusion (not shown) extending from said components, or by way of a groove 1512 (shown in FIG. 15B) positioned within said components.

As shown in FIG. 15A, string 1508 is coupled to springs 22 of restraining device 10, whereby a "pulling" motion of pull bar may effectively pull springs 22 from a first configuration (not shown in FIG. 15A) to a second configuration as shown in FIG. 15A so that restraining device may be positioned about an organ of interest. In an additional embodiment, string 1508 may be positioned at least partially within the lumen of apparatus 1500, whereby a user of apparatus may pull string 1508 instead of pulling pull bar 1510 to operate apparatus 1500. Various components of apparatus 1500 may comprise any number of suitable materials, including, but not limited to, the various materials referenced herein in connection with components of restraining device 10. For example, string 1508 may comprise, for example, plastic or metal thread.

For example, and in an abdominal cavity with the epiplon lesser curvature dissected, arms 1504 of apparatus 1500 may position restraining device 10 to a desired location, springs 22 of restraining device 10 may be widely opened, thus separating the first engaging component 12 and the second engaging component 16 by using pull bar 1510 to pull the strings 1508 and move springs 22 from an axial position to a 90.degree. position relative to first engaging component 12 and the second engaging component. An "opened" restraining device 10 may then be introduced through the dissected lesser curvature space in parallel position to the intragastric mannequin tube, thus creating a desired pouch size. First engaging component 12 and second engaging component 16, upon positioning restraining device 10 about a stomach, would occupy the anterior and posterior wall of the stomach. When the first engaging component 12 and the second engaging component 16 are located in the desired position, spring 22 approximates the first engaging component 12 and the second engaging component 16 to each other gradually without producing any ischemic or tissue damage. Upon moving springs 22 to their desired location and/or positioning restraining device 10 about the stomach, restraining device 10 is separated from apparatus 1500, strings 1508 are cut and apparatus 1500 is pulled out of the abdominal cavity through the port. Restraining device 10 may then be secured in the gastric tissue with superficial stitches.

FIG. 15B shows an exemplary embodiment of at least a portion of apparatus 1500 engaging a "closed" restraining device 10. As shown in FIG. 15B, arms 1504 of apparatus 1500 are shown engaging first engaging component 12 and second engaging component 16 of restraining device 10 by way of grooves 1512 positioned within said components, permitting apparatus 1500 to deliver restraining device 10 through an abdominal port.

FIGS. 16A and 16B show an exemplary embodiment of an apparatus 1500 engaging/positioning an exemplary restraining device 10 of the disclosure of the present application. As shown in FIGS. 16A and 16B, arms 1504 of apparatus 1500 may engage the first engaging component 12 and the second engaging component 16 of restraining device 10, whereby the "opening" of arms 1504 would facilitate the "opening" of restraining device from a "closed" configuration (as shown in FIG. 16A) to an "open" configuration (as shown in FIG. 16B).

"Opening" restraining device 10, as shown in FIG. 16B, may be performed as follows. In the abdominal cavity with the epiplon lesser curvature dissected, the arms 1504 of apparatus 1500 may be widely opened, thus separating the first engaging component 12 and the second engaging component 16 of restraining device 10. A surgeon, for example and with the aid of laparoscopic graspers, may then "pull" out couplers 1200, placing couplers 1200 in a withdrawn configuration as shown in FIG. 16B. Restraining device 10, in an "open" configuration, may be introduced through the dissected lesser curvature space in parallel position to the intragastric mannequin tube, thus creating the desired stomach pouch size. First engaging component 12 and second engaging component 16, when positioned about a stomach, would occupy the anterior and posterior wall of the stomach. When the first engaging component 12 and the second engaging component 16 are located in the desired position, the user/operator may then approximate the plates to each other gradually (millimetrically) using apparatus 1500 device without producing any ischemic or tissue damage. When the user/operator has positioned restraining device 10, apparatus 1500 would then be separated from restraining device and pulled out of the abdominal cavity through the port. If desired, restraining device may also be secured in the gastric tissue with superficial stitches.

FIGS. 17A and 17B show another exemplary embodiment of an apparatus 1500 engaging/positioning an exemplary restraining device 10 of the disclosure of the present application. As shown in FIGS. 17A and 17B, arms 1504 of apparatus 1500 may engage the first engaging component 12 and the second engaging component 16 of restraining device 10, whereby the use of string 1508 connected to the first engaging component 12 and the second engaging component 16 may be used by an operator of apparatus 1500 to "open" and/or "close" said components. One or more strings 1508, in such exemplary embodiments, may be coupled at their first ends to the first engaging component 12 and/or the second engaging component 16, and may be coupled at their second ends to a string rotator 1700 (another exemplary "puller" of the present disclosure) as shown in FIGS. 17A and 17B. Operation/rotation of string rotator 1700 may then facilitate the "opening" of restraining device 10 from a "closed" configuration (as shown in FIG. 17A) to an "open" configuration (as shown in FIG. 17B). In such an embodiment, arms 1504 may also be positioned upon the first engaging component 12 and/or the second engaging component 16 at or near the center of said components (forming a "pivot" area), and the string rotator 1700 and strings 1504 affixed thereto may operate to keep said components in their axial position. Ultimate restraining device 10 delivery may be performed using one or more methods described herein.

Figure 18:
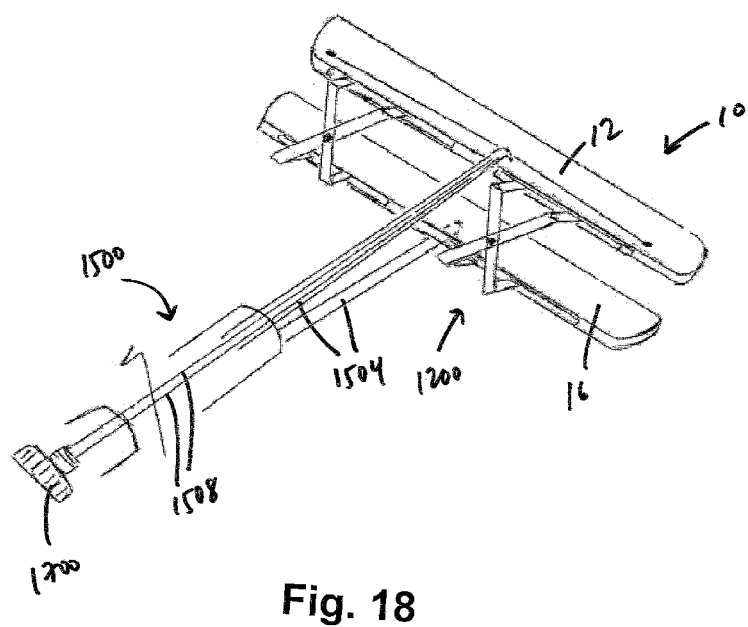
FIG. 18 shows an exemplary embodiment of an apparatus perpendicularly engaging a restraining device according to the present disclosure.

Restraining device 10 may also be positioned "perpendicularly" using apparatus 1500 as shown in FIG. 18. As shown in FIG. 18, arms 1504 and strings 1508 are shown positioned about the first engaging component 12 and the second engaging component 16 "perpendicularly" so that restraining device 10 and apparatus 1500 are not aligned with one another. Rotation of string rotator 1700, as described above, may facilitate the opening and/or closing of restraining device 10.

The various embodiments of restraining devices 10 of the present disclosure may be introduced into a body cavity through, for example, a laparoscopic port. Such restraining devices 10 would be inserted while "compressed" (as shown in FIGS. 1, 7A, 10, 11, 12A, and 14A, for example), and when inserted, would be "opened" or "deployed" (as shown in FIGS. 2, 7B, 8, 9, 13A, 13B, and 14B, for example) prior to being positioned about a stomach 100. In addition, a user of such a restraining device 10 may adjust the opening/deployed dimensions of restraining device 10 prior to positioning it about a stomach, and may further tailor the open/deployed dimensions of restraining device 10 after it has been positioned as desired.

Furthermore, any number of exemplary embodiments of restraining devices 10 of the present application may be wholly or partially resorbable by the body. For example, and using the exemplary restraining device 10 shown in FIGS. 1 and 2 as an example, first and second engaging components 12, 16 may not be resorbable by the body, while springs 22 may be resorbable. In such an embodiment, restraining device 10, once positioned about a stomach 100, may slowly begin the process of total or partial resorption. Resorbable materials suitable for one or more portions of restraining devices 10 may include, but are not limited to, polyglycolide (PGA), polylactide (PLA), l-lactide (LPLA), poly(dl-lactide) (DLPLA), poly(.epsilon.-caprolactone) (PCL), poly (dioxanone) (PDO), polylglycolide-trimethylene carbonate (PGA-TMC), poly(d,l-lactide-co-glycolide) (DLPLG), or combinations thereof.

In a situation where it is desired to have restraining device 10 serve as a reversible bariatric device, and if it is desired not to engage in a subsequent procedure to, for example, laparoscopically remove some or all of restraining device 10 from a body, some or all of restraining device 10 may be resorbed. By way of example, an exemplary restraining device comprising resorbable springs 22 may be positioned about a stomach, and first and second engaging components 12, 16 may slowly become coated with various fibrotic tissue. As springs 22 resorb, springs 22 will eventually no longer operate to connect first and second engaging components 12, 16 to one another, which will effectively cause the various portions of restraining device 10 to no longer serve as a restraining mechanism. Springs 22 may also become coated, in part or in their entirety, by fibrotic tissue, so that when springs 22 resorb, first and second engaging components 12, 16 remain positioned about stomach 100, but the introduction of food into a stomach 100, for example, does not exert any pressure on springs 22 by way of first and second engaging components 12, 16 as first and second engaging components 12, 16 are no longer connected to one another by way of springs 22. Furthermore, first and second engaging components 12, 16 may be resorbable and springs 22 may not, so as first and second engaging components 12, 16 resorb within the body, springs 22 no longer serve to connect first and second engaging components 12, 16 to each other, and restraining device 10 no longer performs any restraining function. Additional embodiments of restraining devices 10 may be resorbable, including, but not limited to, struts 700 and mesh curtain 702.

Regarding removal of exemplary embodiments of restraining devices 10 of the present application, said restraining devices 10 may be removed in whole or in part, for example, by way of a laparoscopic procedure. Reversibility of restraining devices 10, as referenced in the present application, pertains to the ability to position a restraining device 10 about a tissue or organ, and at some time thereafter, have some or all of restraining device 10 resorb within a body or remove some or all of restraining device from the body so that restraining device 10 no longer functions to restrain a tissue or organ. For example, and referencing the exemplary embodiments shown in FIGS. 1 and 2, a laparoscopic procedure to remove springs 22 from the restraining device 10 and the body, but not to remove first and second engaging components 12, 16 from the body, would have the effect of "reversing" the procedure of placing said restraining device 10 about a tissue or organ. Similarly, and as shown in FIGS. 7A, 7B, and 8, removal of struts 700 from restraining device 10 would also have the effect of "reversing" the placement of restraining device 10 about a tissue or organ.

Figure 19:
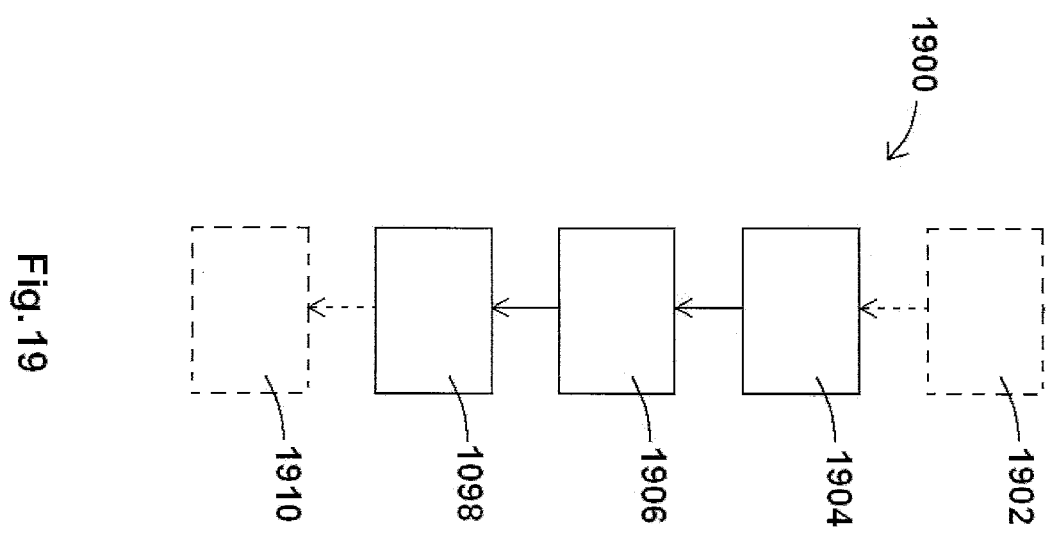
FIG. 19 shows a flow chart of a method for laparoscopically removing embodiments of the restraining device disclosed herein from a targeted tissue according to the present disclosure.

Furthermore, and if desired, the entirety of restraining device 10 may be removed laparoscopically by, for example, reversing the steps used to insert said restraining device 10 within a body. For example, a method 1900 for removing a restraining device 10 from a body as shown in FIG. 19 may comprise the steps of withdrawing restraining device 10 from a tissue or organ (withdrawal step 1904), configuring restraining device 10 to fit within a laparoscopic port (configuration step 1906), and removing restraining device 10 from the body through a laparoscopic port (removal step 1908). Such an exemplary method may be preceded by positioning a laparoscopic port within a body to facilitate removal of restraining device 10 (port insertion step 1902), and may be followed by removing said laparoscopic port from the body after removal step 1908 (port removal step 1910).

Figure 20:
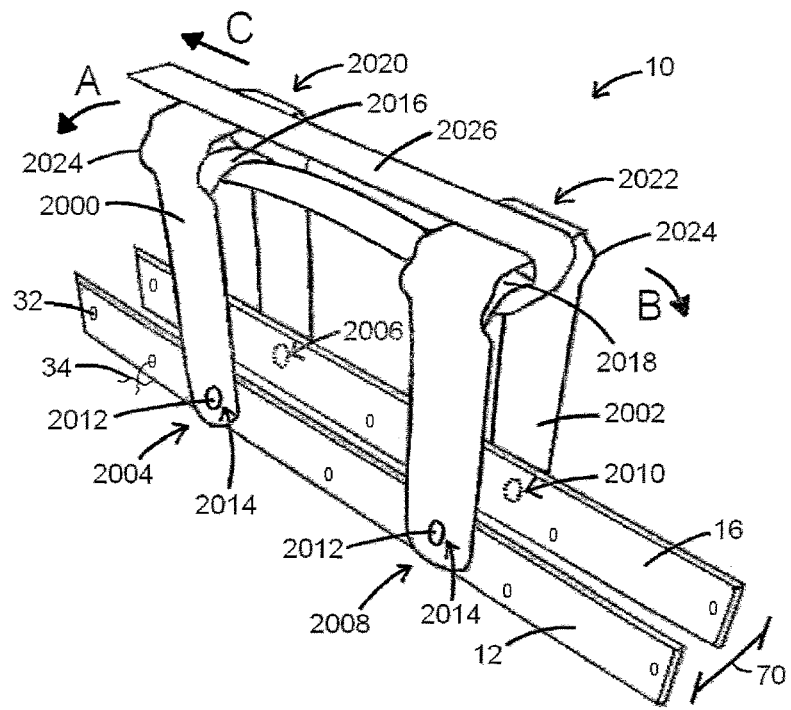
FIG. 20 shows a perspective view of at least another embodiment of a restraining device for restoring and/or supporting a tissue or organ of the present disclosure.
Figure 23:
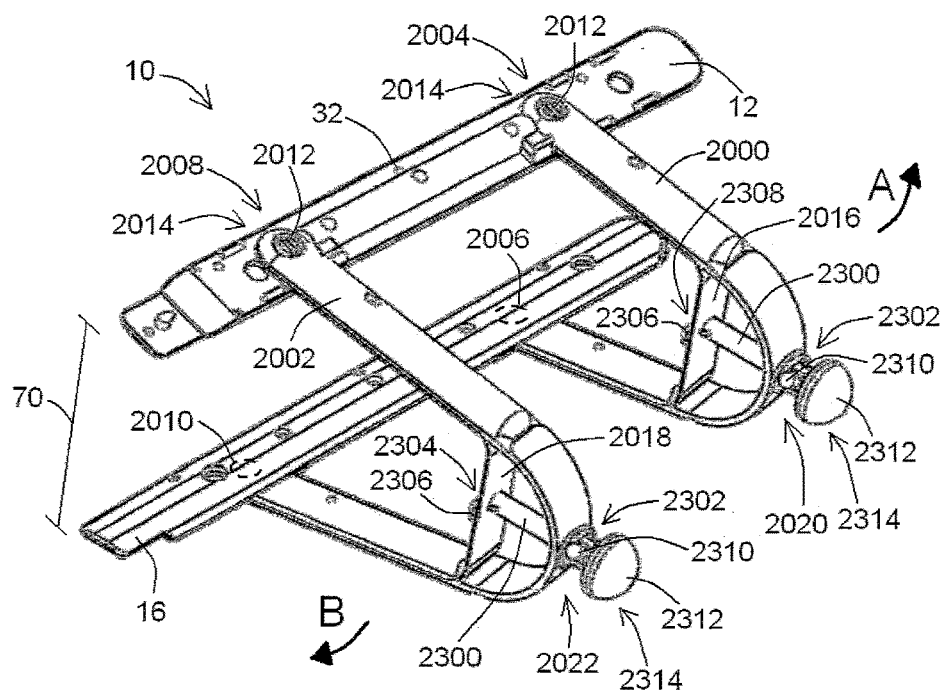
FIG. 23 shows a perspective view of at least another embodiment of a restraining device for restoring and/or supporting a tissue or organ of the present disclosure.

Additional embodiments of restraining devices 10 of the present disclosure are shown in FIGS. 20 and 23. As shown in the embodiments shown in FIGS. 20 and 23, restraining devices 10 comprise a first engaging component 12 and a second engaging component 16, such as those provided in various other embodiments herein. First engaging component 12 and second engaging component 16, in such an exemplary embodiment, are positioned relatively parallel to one another. A first swivel arm 2000 and a second swivel arm 2002 are pivotally connected to first engaging component 12 and second engaging component 16, so that first swivel arm 2000 engages first engaging component 12 at pivot point 2004 and engages second engaging component 16 at pivot point 2006, and so that second swivel arm 2002 engages first engaging component 12 at pivot point 2008 and engages second engaging component 16 at pivot point 2010. First swivel arm 2000 and second swivel arm 2002 may swivel in the directions shown in arrows A and B in FIGS. 20 and 23, noting that first swivel arm 2000 and second swivel arm 2002 may move in opposite directions, so that one moves in the direction of arrow A and the other moves in the direction of arrow B, or first swivel arm 2000 and second swivel arm 2002 may move in the same direction.

First engaging component 12 and/or second engaging component 16 may present studs 2012, as shown in FIGS. 20 and 23, whereby studs 2012 permit first swivel arm 2000 and/or second swivel arm 2002 to be engaged thereto and permit swiveling/rotation about the various pivot points. In at least one embodiment, studs 2012 have a bulbous component relatively larger than a non-bulbous portion, so that a first swivel arm 2000 and/or a second swivel arm 2002 presenting one or more apertures 2014 therethrough may engage studs 2012. Any number of other means to couple first swivel arm 2000 and/or second swivel arm 2002 to first engaging component 12 and/or second engaging component 16 may be used, such as pins, rivets, snaps, screws, and/or other fasteners or coupling means.

First swivel arm 2000 and second swivel arm 2002, as shown in FIGS. 20 and 23, may further comprise a first interconnection arm 2016 and a second interconnection arm 2018 positioned relative to bends 2020, 2022 of said arms. Bends 2020, 2022, as shown in FIGS. 20 and 23, are positioned in the relative middle (somewhere between the relative ends) of first swivel arm 2000 and a second swivel arm 2002, so that first swivel arm 2000 and second swivel arm 2002 form a relative "U-shape" within restraining device 10. First swivel arm 2000 and/or a second swivel arm 2002 may further comprise various additional curvatures 2024, such as shown in FIG. 20, such that bends 2020, 2022 and/or curvatures 2024 define a native U-shaped configuration as previously described.

An interior space 70 between the first engaging component 12 and the second engaging components 16, as shown in FIGS. 20 and 23, may change depending on various factors and/or configurations of restraining device 10. For example, and during insertion of an embodiment of a restraining device 10 such as shown in FIG. 20 or 23 through a laparoscopic port, first swivel arm 2000 and a second swivel arm 2002 may be relatively parallel to, or in the same relative plane as, first engaging component 12 and second engaging component 16, so that the interior space 70 is relatively small. After insertion, and after swiveling first swivel arm 2000 and a second swivel arm 2002 about first engaging component 12 and second engaging components 16, the interior space 70 may either stay the same or increase to facilitate placement of restraining device 10 about a stomach, for example. Furthermore, the use of a tape 2026 positioned about one or more of the first swivel arm 2000 and the second swivel arm 2002, as shown in FIG. 20, may further adjust the amount of interior space 70 between the first engaging component 12 and the second engaging components 16 depending on the amount of relative tension (pull) is applied to tape 2026. For example, if tape 2026 is positioned about one or more of the first swivel arm 2000, and the second swivel arm 2002 so that pulling tape 2026 in a direction shown by arrow C in FIG. 20 causes portions of tape 2026 to press against first interconnection arm 2016 and/or second interconnection arm 2018 causing the relative ends of each of first swivel arm 2000 and a second swivel arm 2002 to move toward each other, the amount of interior space 70 between first engaging component 12 and second engaging component 16 may be reduced. In such an embodiment, restraining device 10 could be inserted into a mammalian body, positioned around a bodily organ without applying pressure to said organ, and tape 2026 could be pulled so that the amount of interior space 70 is adjusted as desired for the particular application. In a bariatric application, for example, it is desired not to have portions of restrictive device 10 apply any pressure about the stomach, but tape 2026 could be pulled/adjusted so first engaging component 12 and second engaging component 16 properly engage the stomach and be sutured thereto as desired. Distention of the stomach, such as by the introduction of solid and/or liquid food or water into the stomach, would cause the stomach to exert a force/pressure against the first engaging component 12 and second engaging component 16, forming a first stomach portion 110 and a second stomach portion 112 as shown in FIGS. 4A and 4B referenced above and FIG. 21 referenced below.

In addition, and as shown in the exemplary embodiments of restraining devices 10 of the present disclosure shown in FIGS. 20 and 23, various portions of restraining device 10, such as the first engaging component 12, the second engaging component 16, the first swivel arm 2000, and/or the second swivel arm 2002 may have one or more suture apertures 32 defined therethrough to facilitate the placement of one or more sutures 34 (also referred to herein as strings 34) to couple restraining device 10 to a portion of a mammalian body, such as a stomach. In various embodiments, one or more of the relative ends of the first engaging component 12 and the second engaging component 16 may be rounded and/or tapered to improve overall patient comfort when a restraining device is positioned within the patient's body.

Figure 21:
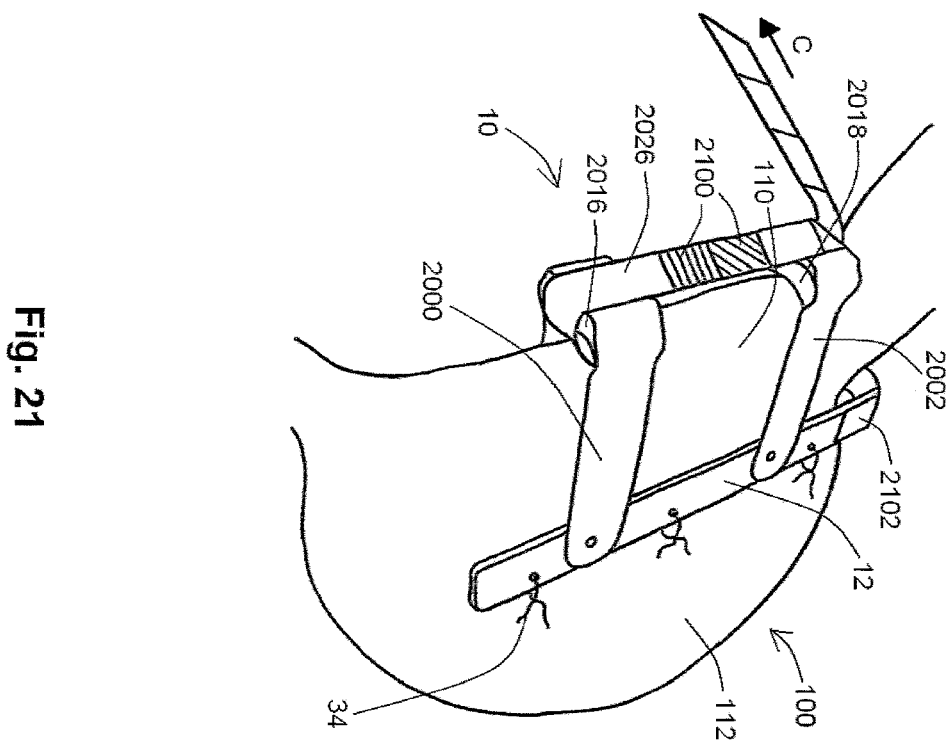
FIG. 21 shows an exemplary embodiment of a restraining device positioned about a stomach according to the present disclosure.

FIG. 21 shows an exemplary embodiment of a restraining device 10, such as shown in FIG. 20, positioned about a stomach. As shown in FIG. 21, device 10 may be positioned about stomach 100 similar to placement of restraining device 10 about stomach 100 as shown in FIG. 5B, so that the first engaging component 12 and the second engaging component 16 (not shown in FIG. 21) may engage opposite sides of stomach 100. Restraining device 10 may be secured to stomach 100 using one or more sutures 34 to couple restraining device 10 to stomach 100, and restraining device 100 may be further positioned about stomach 100 by way of adjusting tape 2026 positioned around restraining device 10. As shown in FIG. 21, tape 2026 is positioned about restraining device 10 so to engage first interconnection arm 2016 and second interconnection arm 2018, whereby pulling tape 2026 in a direction shown by arrow C would cause first engaging component 12 and second engaging component 16 to move closer to one another. Tape 2026 may have one or more detectable portions 2100 positioned/imprinted thereon, so that a user of restraining device 10 can "see" the adjustment of tape 2026 by way of fluoroscopy (if detectable portions 2100 are radioopaque), camera, or other means whereby portions of a device positioned within a body can be visualized, either directly or through some sort of technological means, to allow a user of such a device to adjust the same.

Furthermore, and as shown in FIG. 21, restraining device 10 may have a cover flap 2012 positioned thereon to assist maintaining the placement of restraining device 10 about stomach 100. Cover flap 2012, as shown in FIG. 21, may be ultimately coupled to first engaging component 12 and second engaging component 16 (not shown in FIG. 21), so that after restraining device 10 is positioned about a stomach 100, cover flap 2012 may be closed (initially secured to first engaging component 12 and closed by way of securing cover flap 2012 to second engaging component 16, or vice versa) about an upper portion of stomach 100.

As referenced above, restraining device 10 is positioned about stomach 100 so not to exert pressure upon stomach 100, but when stomach 100 becomes distended, stomach 100 exerts pressure/force upon first engaging component 12 and second engaging component 16 of restraining device 10.

Figure 22:
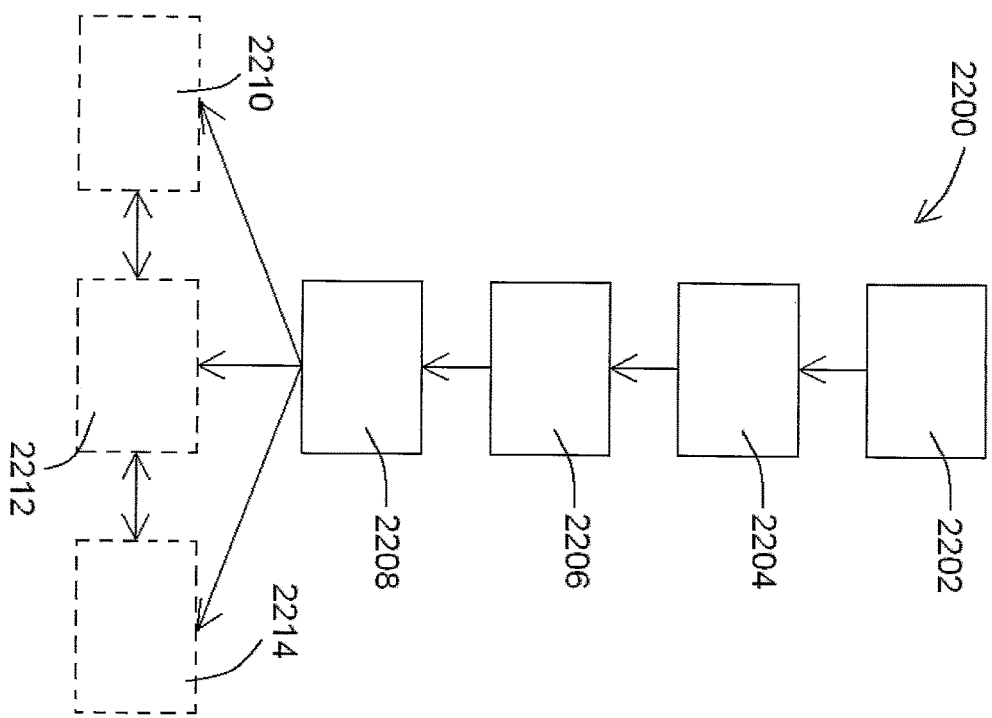
FIG. 22 shows steps of an exemplary method of inserting, delivering, and placing a restraining device about a targeted tissue according to the present disclosure.

Steps of a method for delivering and positioning an embodiment of a restraining device 10, such as the embodiment shown in FIGS. 20 and 21, are shown in FIG. 22. As shown in FIG. 22, exemplary method 2200 comprises the step of laparascopically inserting/advancing restraining device 10 into a patient's body (an exemplary insertion step 2202). In at least one embodiment, the restraining device 10 may be inserted through a 15 millimeter cannula under insufflation into the appropriate cavity of the patient's body. This may be achieved through use of an exemplary delivery device known in the art. At step 2202, first swivel arm 2000 and second swivel arm 2002 of restraining device 10 are swiveled/positioned in the substantially parallel position such that the overall diameter of the restraining device 10 is sufficiently narrow for insertion into the body.

At step 2204, restraining device 10 is advanced to a location adjacent to a targeted tissue, such as a stomach 100 (an exemplary advancement step 2204). At step 2206 (an exemplary swivel step), first swivel arm 2000 and second swivel arm 2002 of restraining device 10 are swiveled from a substantially parallel position to a substantially perpendicular position, separating the first and second engaging components 12, 16 from one another to a native interior space 70. Step 2206 may be performed using any number of standard laparoscopic tools known in the art useful to pull and grasp portions of a tissue or a device. In this manner, neither the proximal ends 13, 17 nor distal ends 14, 18 of the first and second engaging components 12, 16 of restraining device 10 are blocked by first swivel arm 2000 and second swivel arm 2002, and the first and second engaging components 12, 16 may be advanced over a targeted tissue, such as a stomach 100.

At step 2208, and under fluoroscopy, direct camera control or otherwise, restraining device 10 is positioned over the targeted tissue (an exemplary positioning step). In at least one embodiment, and at step 2206, the first side 12A of the first engaging component 12 is positioned adjacent to the desired surface of the targeted tissue and the first side 16A of the second engaging component 16 is positioned adjacent to an opposite side of the targeted tissue. As the first and second engaging components 12, 16 of the restraining device 10 are positioned adjacent to opposite sides of the targeted tissue, at this step 2208 the targeted tissue is positioned within the interior space 70 formed between the first and second engaging components 12, 16. Further, due to the configuration and composition of restraining device 10, restraining device 10 can remain within the patient's body for as long as the restoration or support treatment delivered thereby is desired.

After restraining device 10 is positioned about a targeted tissue (by way of performing positioning step 2208), method 2200 may further comprise the optional steps of securing one or more sutures to connect restraining device 10 to the targeted tissue (an exemplary suturing step 2210), and may further comprise the step of securing cover flap 2012 to further secure restraining device about the targeted tissue (an exemplary cover flap step 2212). In addition, and as shown in FIG. 22, method 2200 may further comprise the step of adjusting tape 2026 to control/adjust the interior space 70 between the first engaging component 12 and the second engaging component 16 whereby at least a portion of the targeted tissue is positioned therebetween (an exemplary tape adjustment step 2214).

In the exemplary embodiment of a restraining device 10, as shown in FIG. 23, restraining device 10 comprises one or more adjustment rods 2300 coupled to the first swivel arm 2000 and the second swivel arm 2002. In the embodiment shown in FIG. 23, for example, adjustment rods 2300 are coupled to first swivel arm 2000 and second swivel arm 2002 at or near bends 2020, 2022, and are further coupled to a first interconnection arm 2016 and a second interconnection arm 2018, respectively. As shown in FIG. 23, at in at least one embodiment, adjustment rods 2300 are coupled to first swivel arm 2000 and second swivel arm 2002 through swivel arm apertures 2302 defined therethrough, and are further coupled to first interconnection arm 2016 and second interconnection arm 2018 through interconnection arm apertures 2304 defined therethrough.

Figure 24:
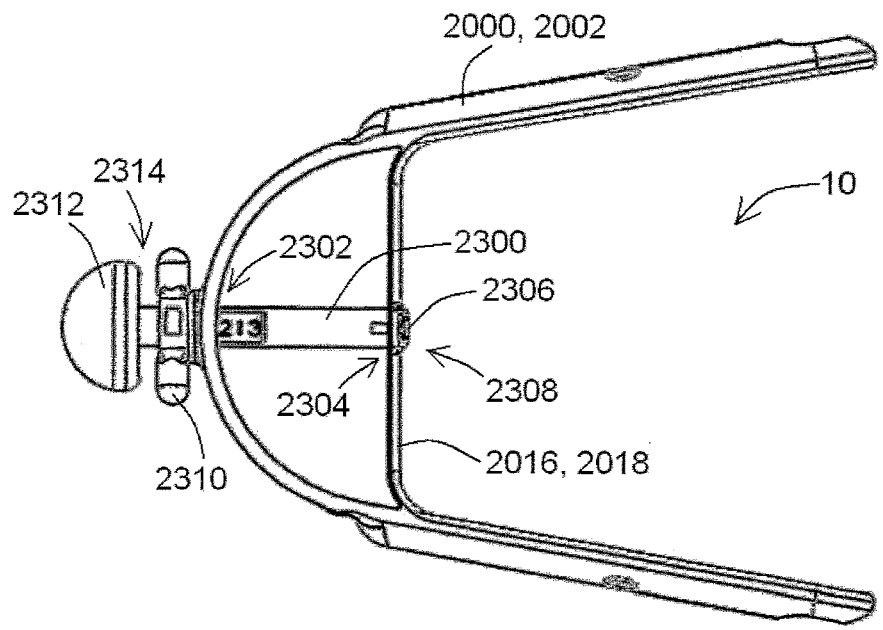
FIG. 24 shows a side view of the embodiment of a restraining device shown in FIG. 23.
Figure 25:
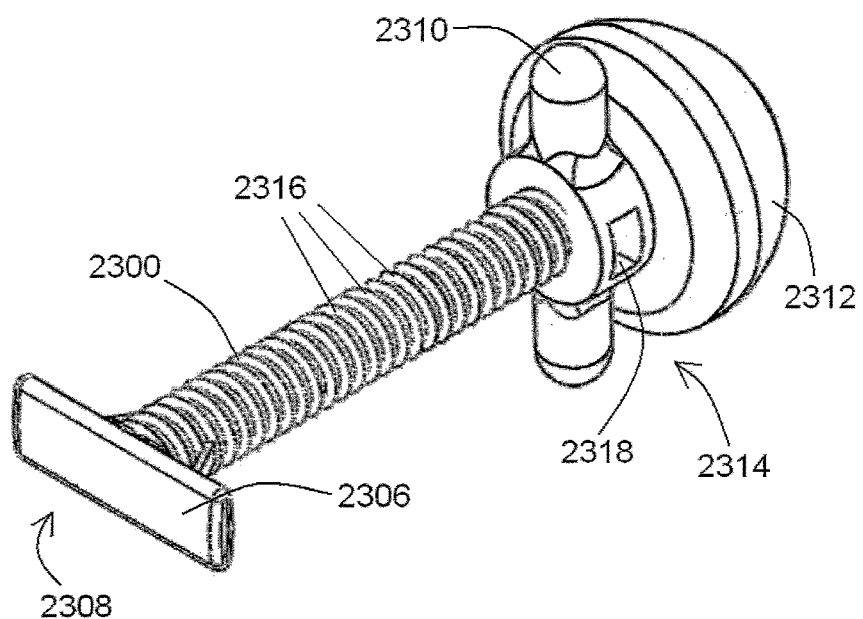
FIG. 25 shows a perspective view of an embodiment of an adjustment rod of the present disclosure.

Adjustment rods 2300, as shown in FIGS. 23 and 25, further comprise a bar 2306 coupled to adjustment rods 2300 at or near a distal end 2308 of adjustment rod 2300. Bar 2306, as shown in FIG. 24, is positioned distal to first interconnection arm 2016/second interconnection arm 2018, so that adjustment of a dial 2310 coupled to adjustment rod 2300 causes movement of first engaging component 12 and second engaging component 16 toward or away from one another. As shown in FIG. 24, first interconnection arm 2016 and second interconnection arm 2018, in various embodiments, may extend either completely or substantially along the length of first swivel arm 2000 and second swivel arm 2002 distal to first interconnection arm 2016 and second interconnection arm 2018, so that adjustment of dial 2310 facilitates movement of first swivel arm 2000 and second swivel arm 2002, thus facilitating movement of first engaging component 12 and second engaging component 16.

As shown in FIGS. 23-25, adjustment rod 2300 may further comprise a cap 2312 coupled thereto at or near a proximal end 2314 of adjustment rod 2300. Cap 2312, as shown in FIGS. 23-25, may prevent dial 2310 from disengaging adjustment rod 2300 so that when restraining device 10 is positioned within a body, dial 2310 remains upon restraining device 10. Cap 2312, in at least one embodiment, may be bulbous/rounded at one end for comfort when restraining device 10 is positioned within a body.

As shown in FIG. 24, dial 2310 may facilitate adjustment of device 10 by way of threads 2316 positioned along adjustment rod 2300. In such an embodiment, rotation of dial 2310 in a first direction would cause first engaging component 12 and second engaging component 16 to move toward one another, and rotation of dial 2310 in a second/opposite direction would cause first engaging component 12 and second engaging component 16 to move away from one another. As such, restraining device 10 may be positioned within a body about a stomach, for example, and be adjusted using dial 2310 so that restraining device 10 is optimally positioned about the stomach.

Figure 26:
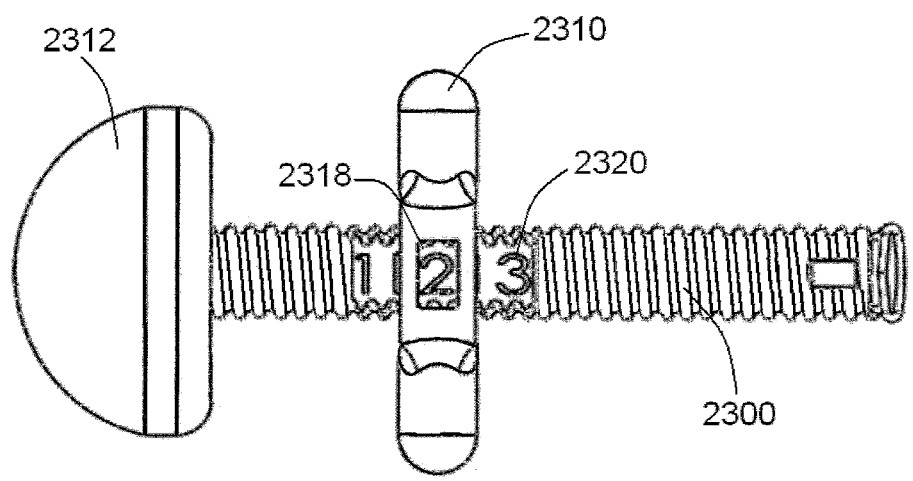
FIG. 26 shows a side view of the embodiment of an adjustment rod shown in FIG. 25.

As shown in the exemplary embodiments in FIGS. 25 and 26, dial 2310 may define a dial aperture 2318, whereby indicia 2320 upon adjustment rod 2300 may be viewed therethrough. As shown in FIG. 26, for example, as dial 2310 is rotated, one or more indicia 2320 may be visible through dial aperture 2318, so that a user of such an embodiment of a restraining device 10 of the present disclosure may identify a level of adjustment. Indicia 2320 may be one or more numbers, letters, lines and/or other indicia 2320 useful to identify a level of adjustment of restraining device 10.

Figure 27:
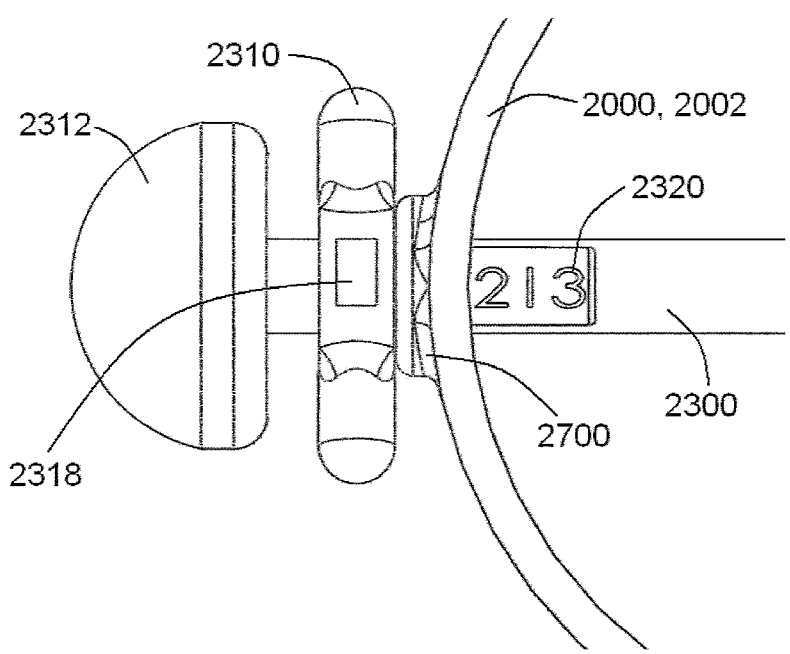
FIG. 27 shows a side view of an embodiment of an adjustment rod coupled to at least another component of an exemplary restraining device of the present disclosure.

As shown in FIG. 27, and in at least one embodiment of a restraining device 10 of the present disclosure, restraining device 10 further comprises at least one flange 2700 coupled to first swivel arm 2000 and/or second swivel arm 2002. Flange 2700 defines an aperture therethrough so that adjustment rod 2300 may fit therethrough, providing physical support for dial 2310 as dial 2310 engages said flange 2700.

Figure 28:
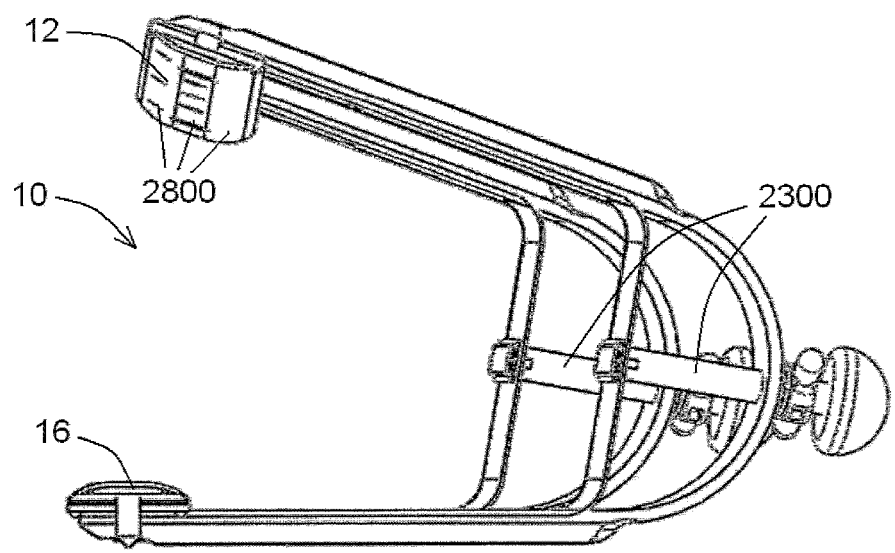
FIG. 28 shows another perspective view of the embodiment of a restraining device shown in FIG. 23.

An exemplary embodiment of a restraining device 10 of the present disclosure having adjustment rods 2300 is shown in FIG. 28. As shown in FIG. 28, first engaging component 12 and/or second engaging component 16 may define one or more facets 2800 along at least part of the length of said components 12, 16, whereby facets 2800 provide a generally arcuate profile as shown therein. Facets 2800 may further improve the overall comfort of restraining device 10 when it is positioned with a patient's body.

Figure 29:
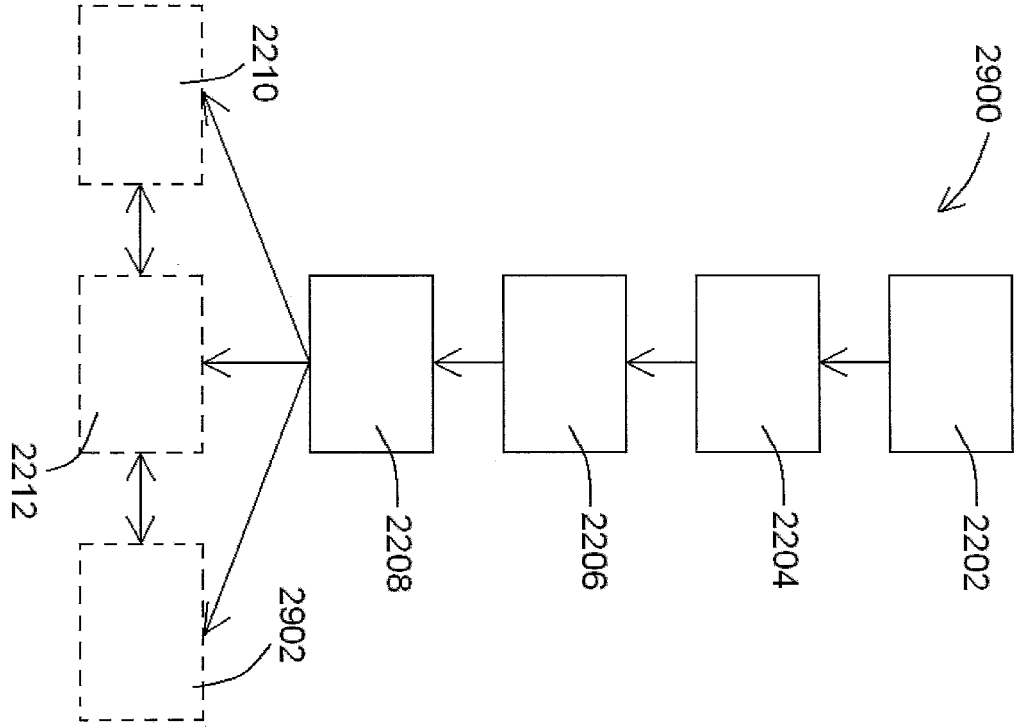
FIG. 29 shows steps of another exemplary method of inserting, delivering, and placing a restraining device about a targeted tissue according to the present disclosure.

Steps of a method for delivering and positioning an embodiment of a restraining device 10, such as the embodiment shown in FIG. 23, are shown in FIG. 29. As shown in FIG. 29, exemplary method 2900 comprises the step of laparascopically inserting/advancing restraining device 10 into a patient's body (an exemplary insertion step 2202) as previously discussed herein. At step 2202, first swivel arm 2000 and second swivel arm 2002 of restraining device 10 are swiveled/positioned in the substantially parallel position such that the overall diameter of the restraining device 10 is sufficiently narrow for insertion into the body.

At step 2204, restraining device 10 is advanced to a location adjacent to a targeted tissue, such as a stomach 100 (an exemplary advancement step 2204). At step 2206 (an exemplary swivel step), first swivel arm 2000 and second swivel arm 2002 of restraining device 10 are swiveled from a substantially parallel position to a substantially perpendicular position, separating the first and second engaging components 12, 16 from one another to a native interior space 70 as previously discussed herein.

At step 2208, and under fluoroscopy, direct camera control or otherwise, restraining device 10 is positioned over the targeted tissue (an exemplary positioning step) as previously referenced herein. After restraining device 10 is positioned about a targeted tissue (by way of performing positioning step 2208), method 2900 may further comprise the optional steps of securing one or more sutures to connect restraining device 10 to the targeted tissue (an exemplary suturing step 2210), and regarding an embodiment of restraining device 10 of the present disclosure comprising a cover flap 2012, method 2900 may further comprise the step of securing cover flap 2012 to further secure restraining device about the targeted tissue (an exemplary cover flap step 2212). In addition, and as shown in FIG. 29, method 2900 may further comprise the optional step of rotating dial 2310 to control/adjust the interior space 70 between the first engaging component 12 and the second engaging component 16 whereby at least a portion of the targeted tissue is positioned therebetween (an exemplary dial adjustment step 2902).

Figure 30:
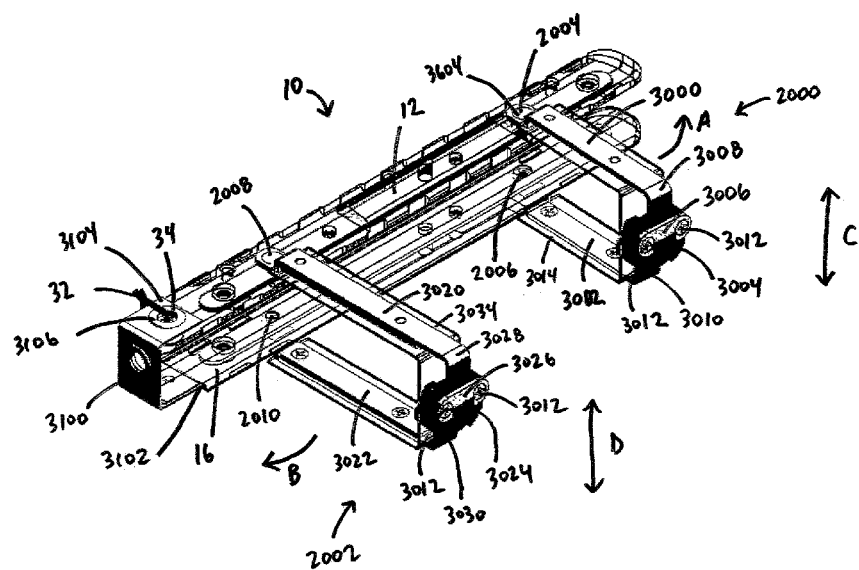
FIG. 30 shows a perspective view of an exemplary embodiment of a restraining device of the present disclosure in a relatively open configuration.
Figure 31:
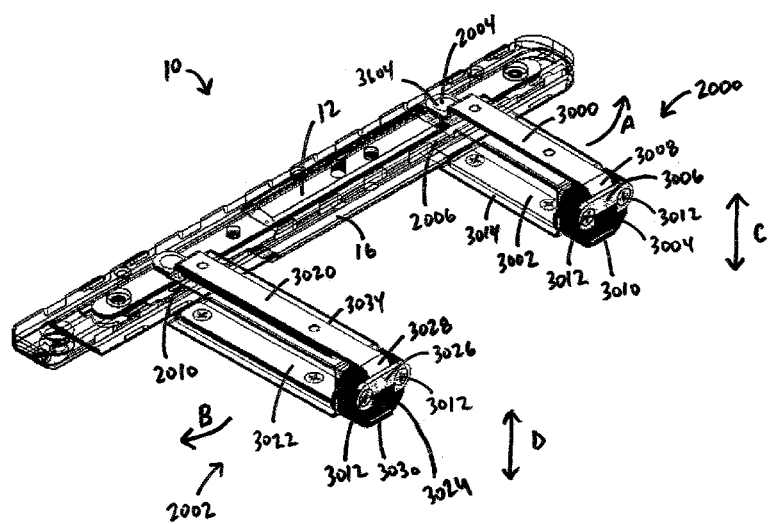
FIG. 31 shows a perspective view of an exemplary embodiment of a restraining device of the present disclosure in a relatively open configuration.

An additional embodiment of a restraining device 10 of the present disclosure is shown in FIGS. 30 and 31. As shown in FIGS. 30 and 31, restraining devices 10 each comprise a first engaging component 12 and a second engaging component 16, such as those provided in various other embodiments herein. First engaging component 12 and second engaging component 16, in such exemplary embodiments, are positioned relatively parallel to one another. A first swivel arm 2000 and a second swivel arm 2002 are pivotally connected to first engaging component 12 and second engaging component 16, so that first swivel arm 2000 engages first engaging component 12 at pivot point 2004 and engages second engaging component 16 at pivot point 2006, and so that second swivel arm 2002 engages first engaging component 12 at pivot point 2008 and engages second engaging component 16 at pivot point 2010. First swivel arm 2000 and second swivel arm 2002 may swivel in the directions shown in arrows A and B in FIGS. 30 and 31, noting that first swivel arm 2000 and second swivel arm 2002 may move in opposite directions, so that one moves in the direction of arrow A and the other moves in the direction of arrow B.

As shown in FIGS. 30 and 31, first swivel arm 2000 may comprise a first arm member 3000 and a second arm member 3002, and second swivel arm 2002 may comprise a first arm member 3020 and a second arm member 3022. First arm members 3000, 3020 and second arm members 3002, 3022 may each couple to a hub 3004, 3024 as shown in FIGS. 30 and 31. In at least one embodiment, and as shown in FIGS. 30 and 31, second arm members 3002, 3022 may be fixedly coupled to hubs 3004, 3024, and first arm members 3000, 3020 may slidingly engage said hubs 3004, 3024, whereby portions of first arm members 3000, 3020 are positioned between hubs 3004, 3024 and hub brackets 3006, 3026. First arm members 3000, 3020 may each have at least one bend 3008, 3028 therein, as shown in FIGS. 30 and 31, to facilitate said engagement of first arm members 3000, 3020 to hubs 3004, 3024. First arm members 3000, 3020, in at least one embodiment, are capable of movement relative to hubs 3004, 3024 in the directions shown in arrows C and D in FIGS. 30 and 31, whereby first arm members 3000, 3020 move in a first direction until they contact hubs 3004, 3024, for example, and move in a second direction until arm flanges 3010, 3030 of first arm members 3000, 3020 contact hub brackets 3006, 3026, for example. First arm members 3000, 3020 and second arm members 3002, 3022 may be referred to as "fixed arms" if they are fixed to one of hubs 3004, 3024, and may be referred to as "expandable arms" if they are coupled to hubs 3004, 3024 by way of hub brackets 3006, 3026 to facilitate movement relative thereto.

In at least one embodiment of an exemplary restraining device 10 of the present disclosure, and as shown in FIGS. 30 and 31, hub brackets 3006, 3026 may be coupled to hubs 3004, 3024 by way of one or more fasteners 3012, such as one or more screws, pins, rivets, and the like. Similarly, second arm members 3002, 3022 may be coupled to hubs 3004, 3024 by way of one or more fasteners 3012. In at least one embodiment, first arm members 3000, 3020 and/or second arm members 3002, 3022 are comprised of stainless steel (such as 316LVM, or implant-grade stainless steel) hubs 3004, 3024 are comprised of one or more polyaryletherketones (PEEKs), and hub brackets 3006, 3026 are also comprised of stainless steel. First engaging component 12 and second engaging component 16 may, in at least one embodiment, comprise stainless steel which may then be coated/overmolded with a biocompatible polymer, such as polyurethane (PX205, for example) or tecothane (TT-1075D-M, for example).

In various embodiments of restraining devices 10 of the present disclosure, restraining devices 10 may comprise one or more pads 3014, 3034 coupled to first arm members 3000, 3020 and/or second arm members 3002, 3022. Said pads 3014, 3034 may comprise any number of biocompatible polymers and/or other materials that are suitable for contacting an organ, such as a stomach, and which may provide some sort of cushioning effect. In at least one embodiment, pads 3014, 3034 may be comprised of a biocompatible polymer such as carbothane (such as PC-3595A), for example, and may be coupled to first arm members 3000, 3020 and/or second arm members 3002, 3022 using one or more fasteners 3012. In at least one embodiment, fasteners 3012, as referenced herein, may be comprised of stainless steel.

Regarding the exemplary embodiment of restraining device 10 shown in FIGS. 30 and 31, restraining device is shown in an open configuration in FIG. 30 and in a closed configuration in FIG. 31. As shown in FIG. 31, an exemplary restraining device 10 of the present disclosure may comprise a strap 3100 coupled thereto at first engaging component 12 and second engaging component 16. In at least one embodiment, strap 3100 is fixedly coupled to one or both of first engaging component 12 and second engaging component 16, and in another embodiment, strap is removably coupled to one or both of first engaging component 12 and second engaging component 16 by way of one or more sutures 32 (such as a 2-0 silk suture, for example), as shown in FIG. 31. As shown in the embodiment of restraining device 10 in FIG. 31, a first end 3102 of strap 3100 is fixedly coupled to second engaging component 16, and a second end 3104 of strap 3100 is removably coupled to first engaging component 12 by way of suture 32. In practice, suture 32 may not be positioned within suture aperture(s) 34 defined within one or more components of restraining device 10 until after restraining device 10 has been inserted into a mammalian body. In at least one embodiment, one or more suture apertures 34 defined within one or more components of restraining device 10 may comprise/define one or more eyelets 3106, whereby said eyelets 3106 provide additional reinforcement/strength, and may also provide a more smooth, rounded contour than suture apertures 34 so not to cause unintended wear, and potential breakage, of one or more sutures 32 positioned therethrough. In at least one embodiment, strap 3100 comprises carbothane (PC-3595A), and eyelets 3106 are comprised of nickel. In at least another embodiment, strap 3100, or portions thereof, may be radiopaque.

Figure 32:
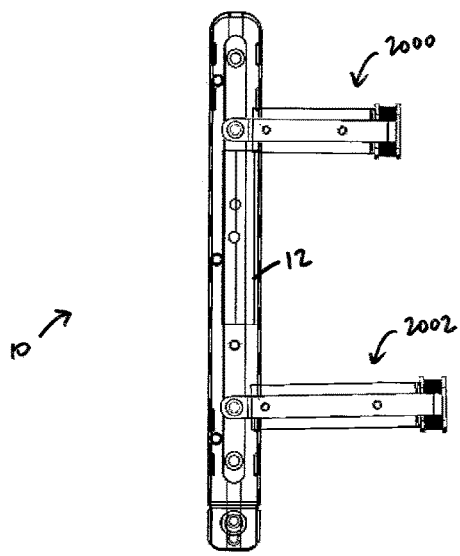
FIGS. 32 and 33 show top views of an exemplary embodiment of a restraining device of the present disclosure.
Figure 33:
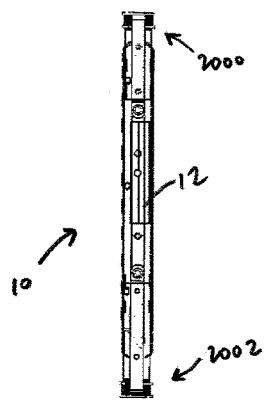
Figure 40:
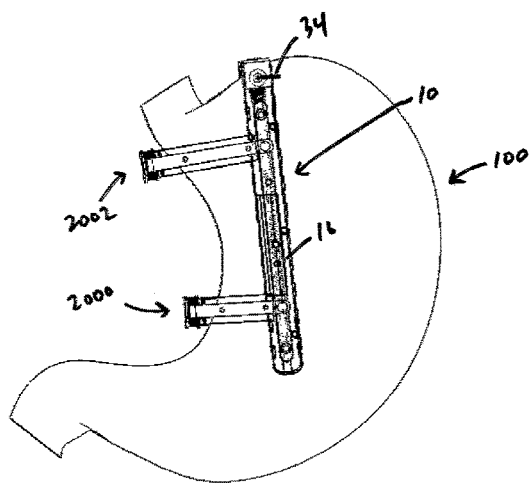
FIGS. 40, 41, and 42 show exemplary embodiments of restraining devices of the present disclosure positioned about a stomach.
Figure 41:
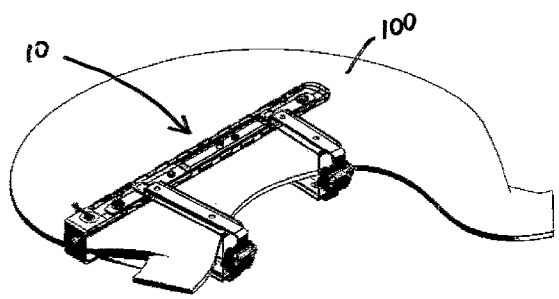
Figure 42:
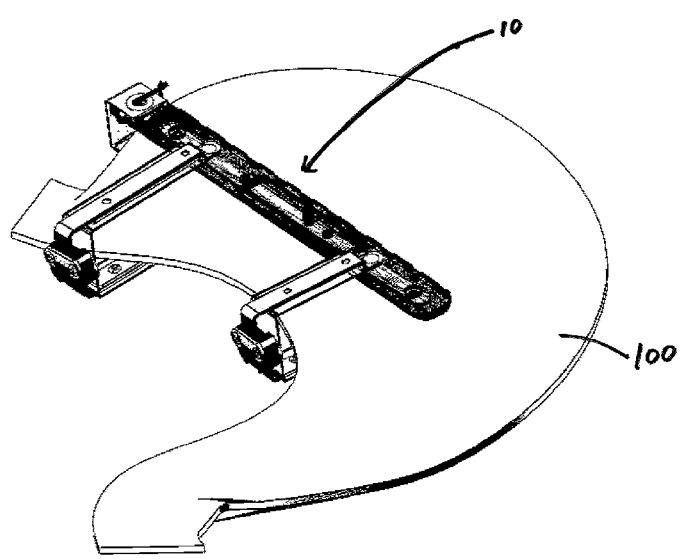

FIGS. 32 and 33 show top views of exemplary restraining devices 10 of the present disclosure. As shown in FIG. 32, restraining device 10 is shown with first swivel arm 2000 and second swivel arm 2002 in a positioned whereby said arms 2000, 2002 are at least substantially perpendicular to first engaging component 12. As shown in FIG. 32, and in at least one embodiment of a restraining device 10 of the present disclosure, first swivel arm 2000 is relatively shorter than second swivel arm 2002, whereby such a configuration allows for placement of restraining device 10 about a stomach, for example, as shown in FIGS. 40, 41, and 42.

Figure 34:
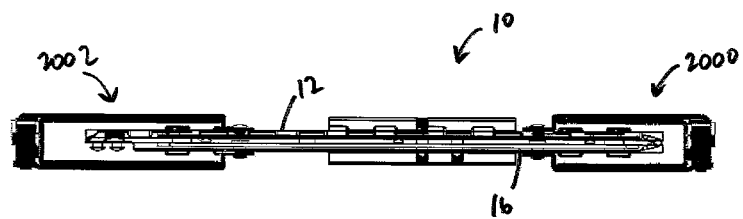
FIG. 34 shows a side view of an exemplary embodiment of a restraining device of the present disclosure in a relatively closed configuration.
Figure 35:
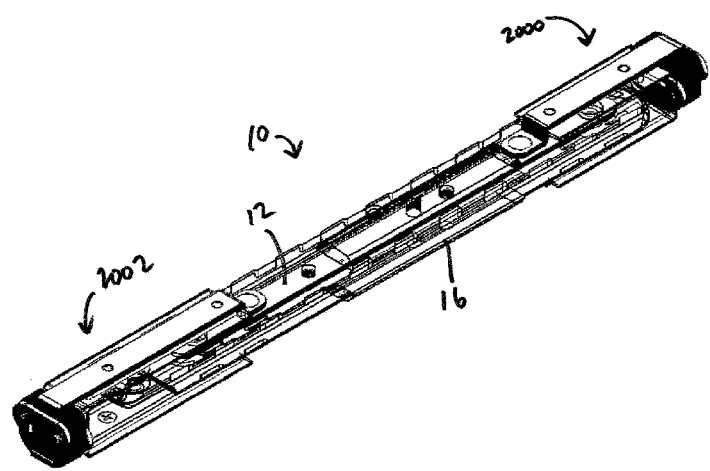
FIG. 35 shows a perspective view of an exemplary embodiment of a restraining device of the present disclosure in a relatively closed configuration.

FIG. 33 shows an exemplary restraining device 10 whereby first swivel arm 2000 and second swivel arm 2002 share a common linear axis with first engaging component 12. In the configuration shown in FIG. 33, for example, restraining device 10 may fit within a bodily laparoscopic port for eventual swiveling of arms 2000, 2002 and placement of restraining device 10 about an organ. FIG. 34 shows a front view of an exemplary restraining device 10 of the present disclosure in a similar configuration as shown in FIG. 33, and FIG. 35 shows a perspective view of restraining device 10 in the same configuration.

Figure 36:
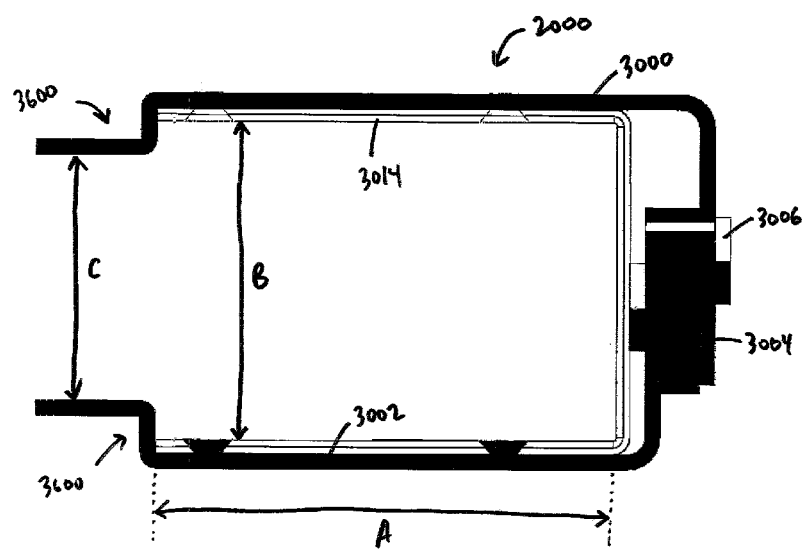
FIG. 36 shows a side view of an exemplary swivel arm of the present disclosure.
Figure 37:
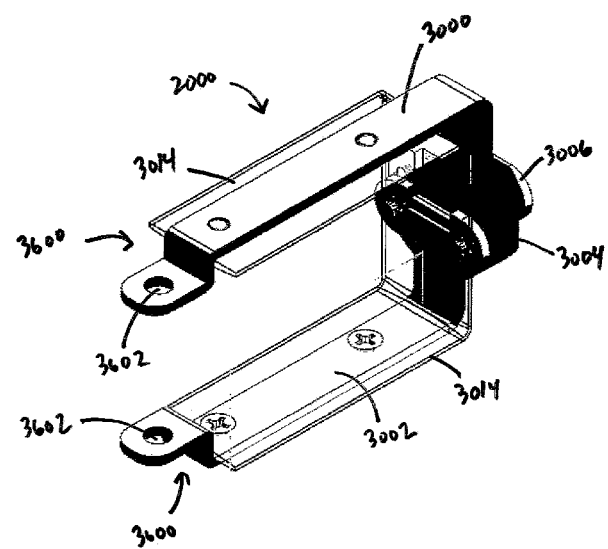
FIG. 37 shows a perspective view of an exemplary swivel arm of the present disclosure.

FIGS. 36 and 37 show a side view and a perspective view, respectively, of an exemplary first swivel arm 2000 of the present disclosure. In at least one embodiment, and as shown in FIG. 36, first swivel arm 2000 has an interior length (as indicated by arrow A in the figure) of about 26.5 mm, and has an expanded interior height (as indicated by arrow B in the figure) of about 19.1 mm. In other embodiments, the interior length and interior height may be greater or lesser than those shown in the figure.

As shown in FIGS. 36 and 37, an exemplary first swivel arm 2000 may have one or more distal arm flanges 3600, which, in at least one embodiment, are bent relatively down/up and then out, as shown in the figures, so that exemplary first swivel arm 2000 may engage first engaging component 12 and second engaging component 16 while maintaining integrity of first swivel arm 2000 and/or providing additional clearance for an organ positioned therebetween. In at least one embodiment, and as shown in FIG. 36, distal arm flanges 3600 result in an expanded flange height (as indicated by arrow C in the figure) of less than the expanded interior height. The relative distal ends of first swivel arm 2000, which may themselves comprise distal arm flanges 3600, may comprise one or more arm apertures 3602 configured to receive, for example, one or more rivets 3604 (as shown in FIGS. 30 and 31) therethrough to couple first swivel arm 2000 to a first engaging component 12 and a second engaging component 16. In at least one embodiment, rivets 3604 are comprised of stainless steel. In at least another embodiment, another type of fastener 3012, as described herein, aside from a rivet 3604 may be used.

Figure 38:
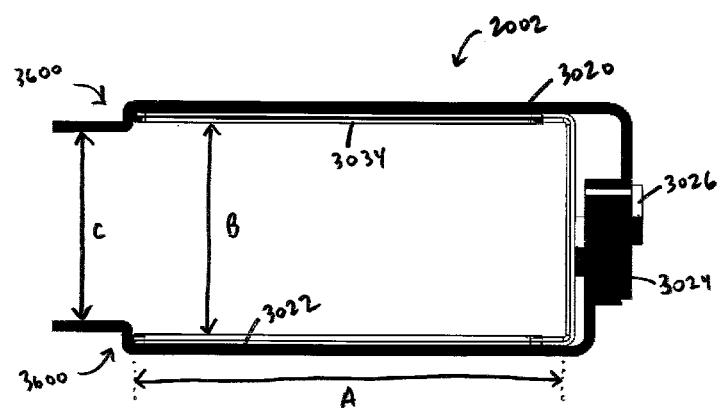
FIG. 38 shows a side view of another exemplary swivel arm of the present disclosure.
Figure 39:
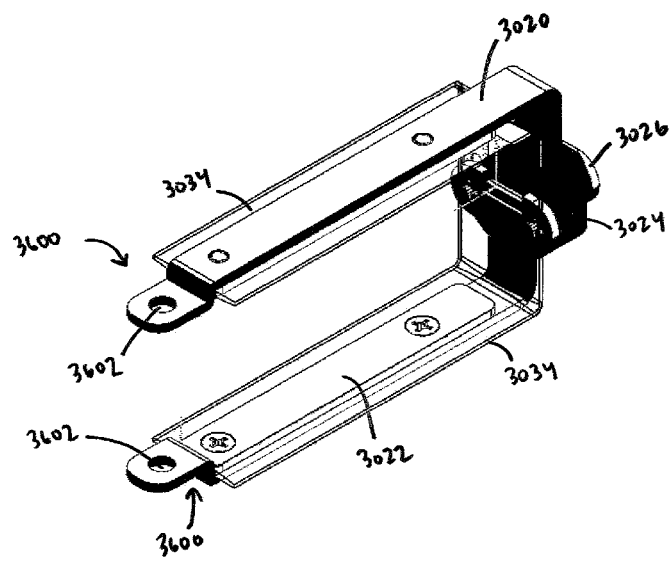
FIG. 39 shows a perspective view of another exemplary swivel arm of the present disclosure.

FIGS. 38 and 39 show a side view and a perspective view, respectively, of an exemplary second swivel arm 2002 of the present disclosure. In at least one embodiment, and as shown in FIG. 38, second swivel arm 2002 has an interior length (as indicated by arrow A in the figure) of about 37 mm, and has an expanded interior height (as indicated by arrow B in the figure) of about 18 mm. In other embodiments, the interior length and interior height may be greater or lesser than those shown in the figure.

As shown in FIGS. 38 and 39, an exemplary second swivel arm 2002 may also have one or more distal arm flanges 3600, which, in at least one embodiment, are bent relatively down/up and then out, as shown in the figures, so that exemplary second swivel arm 2002 may engage first engaging component 12 and second engaging component 16 while maintaining integrity of second swivel arm 2002 and/or providing additional clearance for an organ positioned therebetween. In at least one embodiment, and as shown in FIG. 38, distal arm flanges 3600 result in an expanded flange height (as indicated by arrow C in the figure) of less than the expanded interior height. The relative distal ends of second swivel arm 2002, which may themselves comprise distal arm flanges 3600, may comprise one or more arm apertures 3602 configured to receive, for example, one or more rivets 3604 (as shown in FIGS. 30 and 31) therethrough to couple second swivel arm 2002 to a first engaging component 12 and a second engaging component 16.

FIG. 40 shows an exemplary embodiment of a restraining device 10, such as shown in FIGS. 30 and 31, positioned about a stomach. As shown in FIG. 40, device 10 may be positioned about stomach 100 similar to placement of restraining device 10 about stomach 100 as shown in FIGS. 5B and 21, for example, so that the first engaging component 12 (not shown in FIG. 40) and the second engaging component 16 may engage opposite sides of stomach 100. Restraining device 10 may be secured to stomach 100 using one or more sutures 34 to couple restraining device 10 to stomach 100, or one or more sutures 34 may be positioned within suture aperture(s) 34 within strap 3100 and one or both of first engaging first engaging component 12 and second engaging component 16 to secure restraining device 100 about a stomach 100. FIGS. 41 and 42 show additional views of an exemplary restraining device 10 positioned about a stomach 100.

Figure 43:
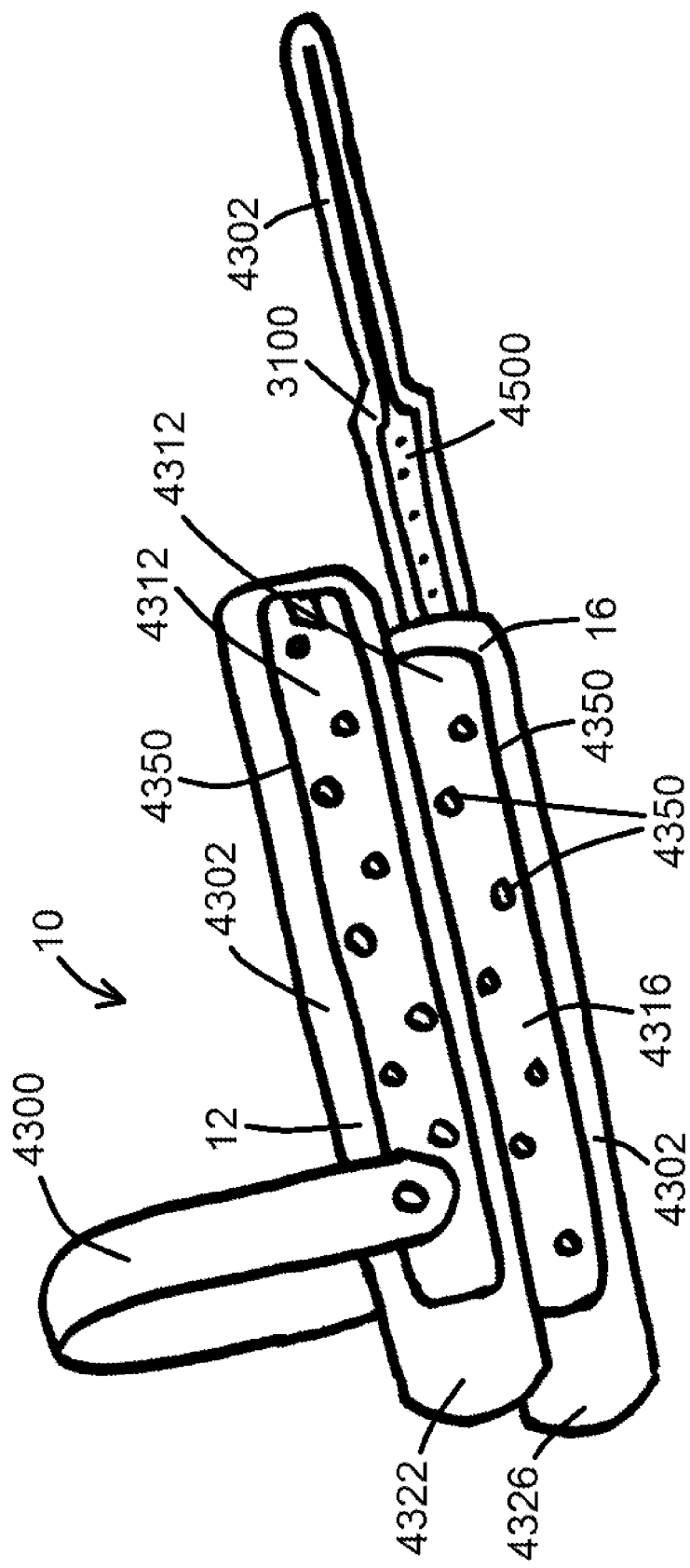
FIGS. 43 and 44 show perspective views of devices, according to exemplary embodiments of the present disclosure.

An exemplary embodiment of a restraining device 10 of the present disclosure is shown in FIG. 43. As shown therein, restraining device 10 comprises a first c-ring 4300 (which may also be referred to herein as an inferior c-ring (and also whereby the various c-rings 4300 or other c-rings of the present disclosure may be exemplary swivel arms 2000, 2002 or other couplers used to couple two engaging components 12, 16 of the present disclosure to one another, as generally described and shown herein)), whereby an inferior c-ring 4300 is relatively rigid and load-carrying in various embodiments, and whereby a superior c-ring 4400 (shown in FIG. 44), in various embodiments, is relatively rigid on one axis and flexible on another axis. Engaging components 12, 16 may be relatively stiff and coated with some sort of coating 4302 (such as an elastomer coating or other coating) as tissue interface material. The flexible coating 4302 can be flexible around the relative edges of the engaging components 12, 16, and excess flexible coating 4302, extending sufficiently from the inner rigid plates 4312 and 4316, as shown in FIG. 43, can gradually distribute any forces of the plates to the tissue (such as the stomach). The coating 4302 (which may also be referred to as a mattress or cushion) also helps prevent shearing and migration of the device 10 with respect to the device 10 rubbing against the tissue or organ. As shown in FIG. 43, for example, coating 4302 extends beyond a perimeter 4530 of each rigid plate 4312, 4316. As the stomach 100 distends, for example, when an exemplary device 10 of the present disclosure is positioned therein, stomach tissue 100 can "roll" relative to coating 4302, preventing migration of portions of device 10 into stomach 100 tissue.

Figure 46:
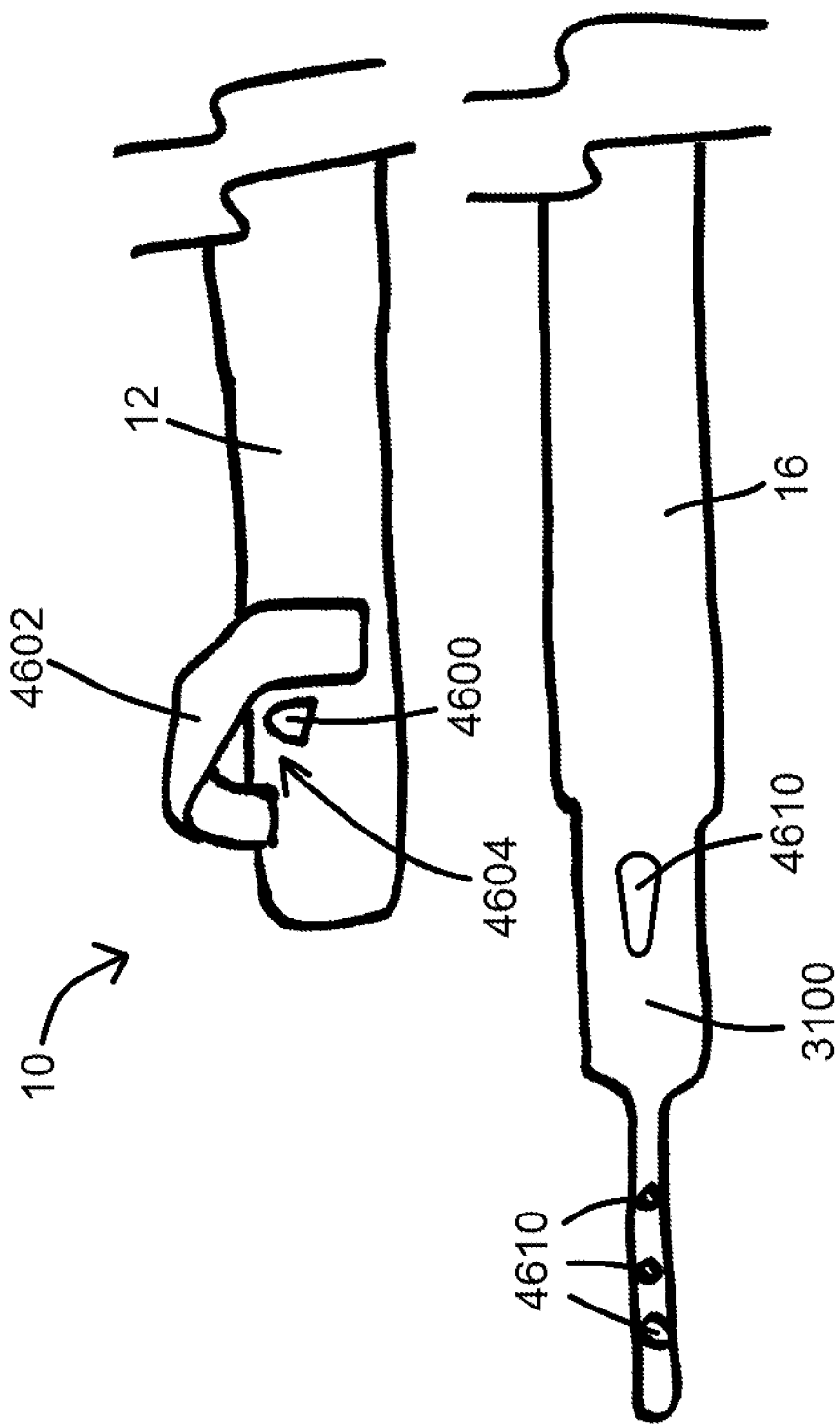
FIG. 46 shows portions of engaging components and a strap, according to an exemplary embodiment of the present disclosure.

Engaging components 12, 16 may also each comprise a tail 4322, 4326 at one end that is relatively flexible and generally comprising a coating material 4302 and not any sort of rigid material (such as used with rigid plates 4312, 4316) therein. The tails 4322, 4326 are shown in FIG. 43. The strap 3100 (also referred to herein as a "fundus strap") shown therein may comprise an embedded, load-carrying element (rigid inner portion 4500) inside of a silicone coating (an exemplary coating 4302). For example, nylon, PEEK mesh, and stainless steel foil can each be exemplary embedded elements 433) within a coating 4302 and still operate as a fundus strap 3100 consistent with the present disclosure. After the device 10 is positioned about a stomach 100 and a fundus strap 3100 wrapped around an upper portion of the stomach 100 (such as from behind stomach 100) and locked into place, excess fundus strap 3100 may be cut off. The fundus strap 3100 can be coupled to the anterior engaging component 16 and lock onto the other engaging component 12. A hook or other mechanism (an exemplary tab 4600, as shown in FIG. 46) may be used to lock a portion of the fundus strap 3100 to the plate (engaging component 12 or 16) that does not have the fundus strap 3100 initially coupled thereto. Use of a fundus strap 3100, in various embodiments, is also to effectively exclude the fundus 90 region from the flow of food into the stomach 100, further directing food to the channel (such as first stomach portion 110 referenced herein) created using the device 10 and not to the fundus 90 area. Regarding overall load-carrying, at least one purpose of using metal (or another rigid material) within the flexible/pliable coating 4302 (such as silicone) is to provide additional strength and also to limit stretch of the portion of device 10 (engaging components 12 and/or 16, fundus strap 3100, and/or c-arms, c-rings 4300 or 4400, or other connectors), so that the same do not distend over time. As referenced herein, such a rigid material can be used with rigid inner plate 4312 and/or 4412 and/or other components as referenced herein.

Figure 44:
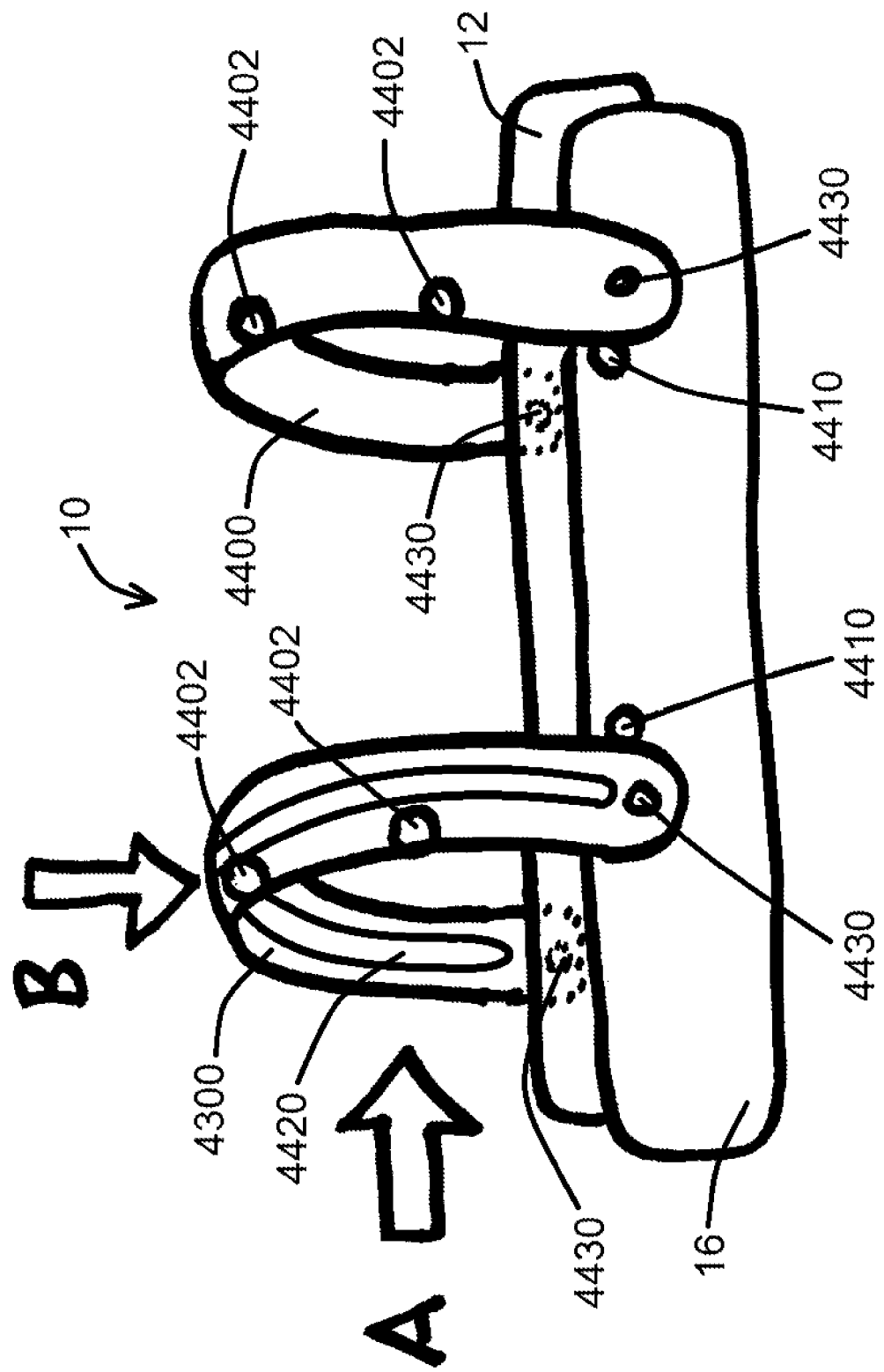

Each c-ring 4300, 4440 may have one, two, or three or more suture features 4402 (such as and/or similar to suture members 36 having suture apertures 32, for example, or other types of suture features) therein as shown in FIG. 44, such as one at a relative apex (middle) of one or both c-rings 4300, 4400, and one between the apex and one end on an anterior side of the device 10 when viewed as positioned upon a stomach 100. Suture features 4402 would allow one or more sutures 34 (also referred to herein as strings 34) to pass therethrough. The engaging components 12, 16 may comprise a stiff inner portion (namely rigid inner plates 4312, 4316, comprising material such as metal) and a flexible or compressible outer coating 4302, such as silicone. Various holes 4350 can be defined within the engaging components 12, 16 or within rigid inner plates 4312, 4316 as shown in FIG. 43, or a fundus strap 3100 stiff inner portion, which can reduce the weight of the device 10 and allow the coating 4302 material to enter the holes 4350 and help with overall binding of the coating 4302 to said components.

The c-rings 4300, 4400 can swivel about engaging components 12, 16, such as about 90°, less, or more. Optional stops 4410 positioned on an engaging component 12 and/or 16 can be used to prevent c-rings 4300, 4400 from swiveling further than desired.

A superior c-ring 4400 and/or an inferior c-ring 4300 can have one or more suture holes (such as suture apertures 32 of suture members 36 and/or suture features 4402) to allow sutures 34 to connect the device 10 to the stomach 100. The superior c-ring 4400 and/or the inferior c-ring 4300 can have an insert 4420, which can be flexible and/or metal, surrounded by silicone or another flexible/pliable material (such as coating 4302) for tissue contact. Rivet holes 4430 can be defined at the relative ends of the superior c-ring 4400 to fasten the same to the engaging components 12, 16. The same or different coating 4302 can be used to coat/surround rigid inner plate 4312, 4316, and/or metal insert(s) 4420.

The superior c-ring 4400 and/or the inferior c-ring 4300 can be flexible in one plane but not two planes. For example, and as shown in FIG. 44, c-ring 4400 can be relatively stiff when pushed in a direction shown by arrow "A", and can be relatively flexible when pushed in a direction shown by arrow "B".

Figure 45:
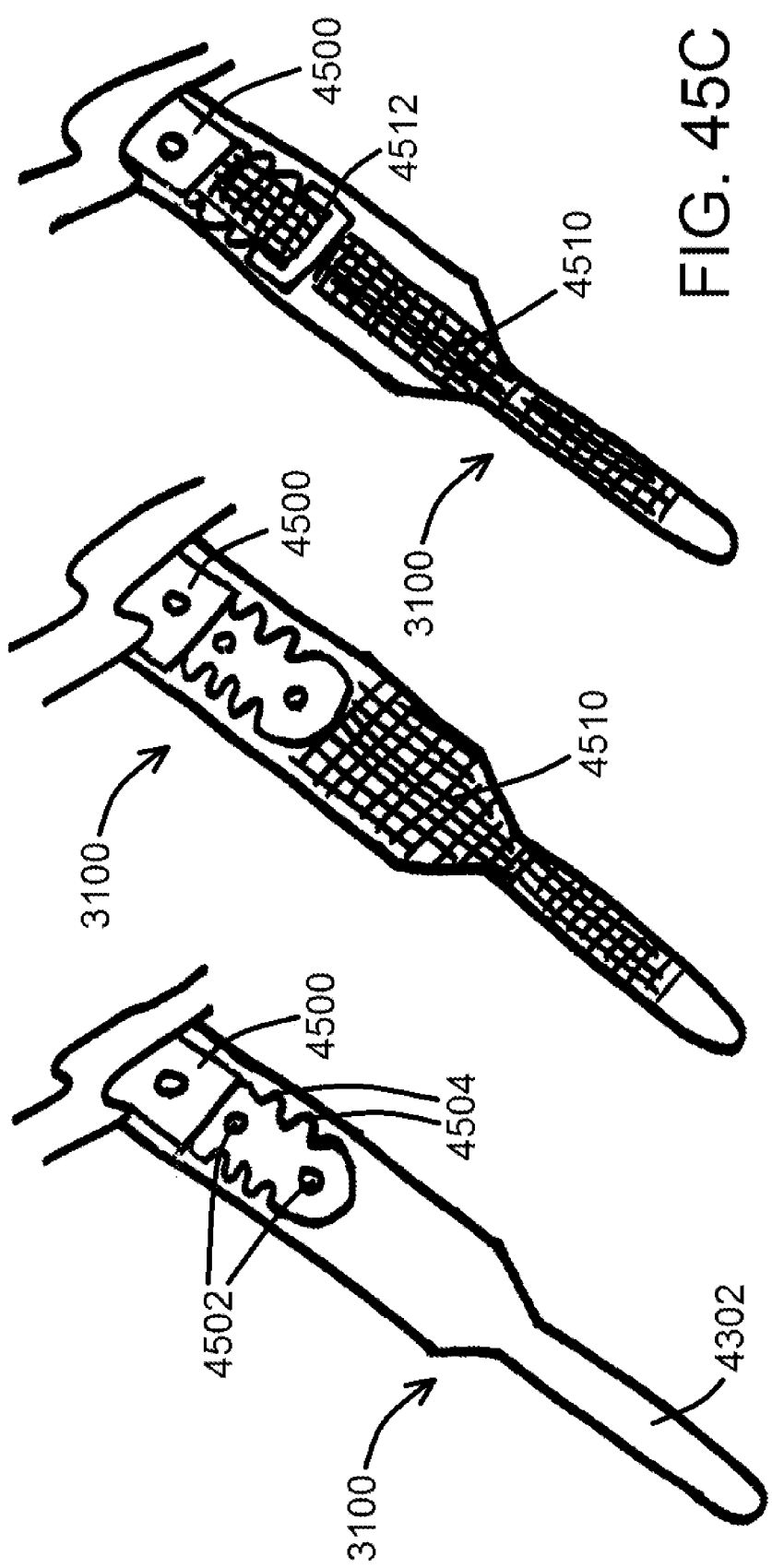
FIGS. 45A, 45B, and 45C show portions of straps, according to exemplary embodiments of the present disclosure.

Distal portions of exemplary fundus straps 3100 are shown in FIGS. 45A, 45B, and 45C. As shown in FIG. 45A, distal portion of fundus strap 3100 has a rigid inner portion 4500 (such as metal) and optionally one or more apertures 4502 or ridges 4504 defined therein, allowing a flexible polymer outer coating 4302 to better adhere and remain in contact with the rigid inner portion 4500. An optional inner mesh 4510 (such as a nylon mesh), as shown in FIG. 45B, can be embedded within the flexible polymer outer coating 4302 to provide additional support to the distal end of the fundus strap 3100. A portion of the rigid inner portion 4500/mesh 4510 may have a mesh aperture 4512 defined therein, as shown in FIG. 45C, whereby a portion of the inner mesh 4510 can be positioned therethrough to further hold the mesh 4510 in place. The various inner portion apertures 4502, ridges 4504, and mesh apertures 4512 can be laser welded, for example.

FIG. 46 shows ends of two engaging components 12, 16, with one having a fundus strap 3100 coupled thereto. The engaging component 12 or 16 that does not have the fundus strap 3100 coupled thereto (engaging component 12, for example, as shown in FIG. 46), and in at least one exemplary device 10 embodiment of the present disclosure, has a loop 4602 and an optional tab 4600 coupled thereto, whereby the loop 4602 defines an opening 4604 sized and shaped to receive a portion of the fundus strap 3100 thereto, and wherein the fundus strap 3100 defines one or more tab apertures 4610 configured to receive the tab 4600. Use of the loop 4602 and/or tab 4600 can secure the end of the fundus strap 3100 to the other engaging component (such as engaging component 12, as shown in FIG. 46). In use, the end of the fundus strap 3100 can be positioned in the loop opening 4604 and either pushed or pulled therethrough until a desired amount of connection is obtained, and further locked into place using tab 4600 and tab aperture 4610. Tab 4600 can be angled or otherwise configured to receive and secure the fundus strap 3100. The loop 4602 can be made of metal or plastic. One of the purposes of such a design, and other designs of the present disclosure, is to aid in laparoscopic placement and ease of handling and placement for the physician placing the device 10 within the patient.

Figure 47A:
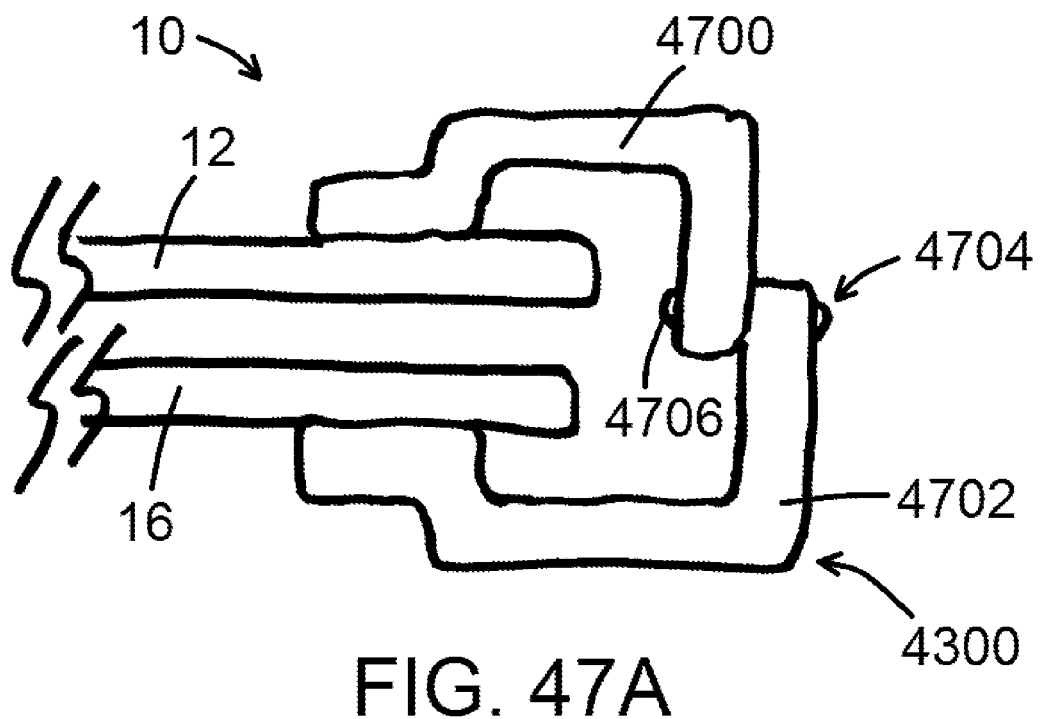
FIGS. 47A-52B show first and second c-ring portions coupled to or configured for coupling to each other, according to exemplary embodiments of the present disclosure.
Figure 47B:
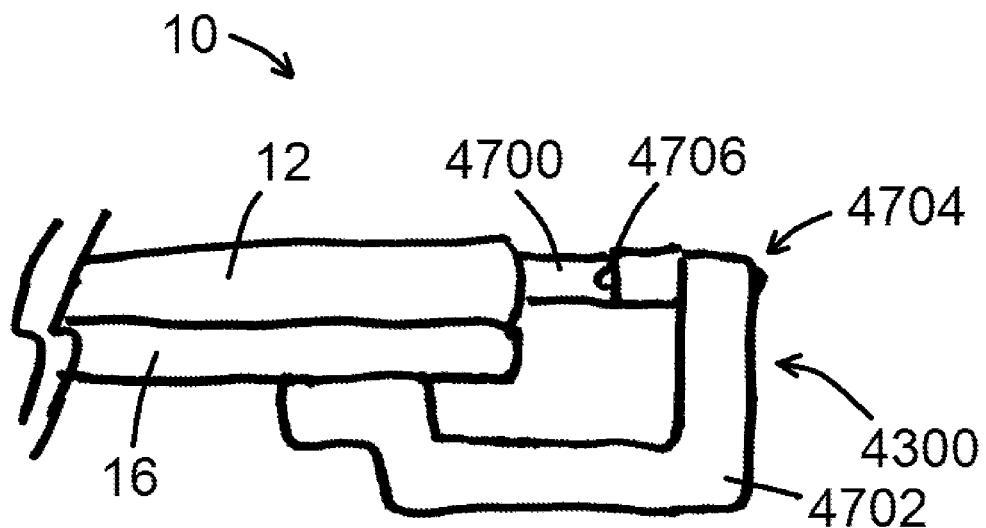

In various device 10 embodiments of the present disclosure, relatively rectangular c-rings 4300, 4400 can fit through a 15 mm trocar and carry the necessary load to maintain a desired engaging component gap. For example, FIGS. 47A and 47B show portions of exemplary restraining devices 10, whereby one or both c-rings 4300, 4310 (one c-ring (4300 chosen for example) shown therein) has/have a first c-ring portion 4700 and a second c-ring portion 4702 connected at a pivot point 4704 using a coupler 4706. Such an embodiment allows the first c-ring portion 4700 to pivot relative to the second c-ring portion 4702 to reduce an overall cross-sectional size of the device 10, such as from changing from a relatively open swivel configuration shown in FIG. 47A to a relatively closed swivel position shown in FIG. 47B.

Figure 48A:
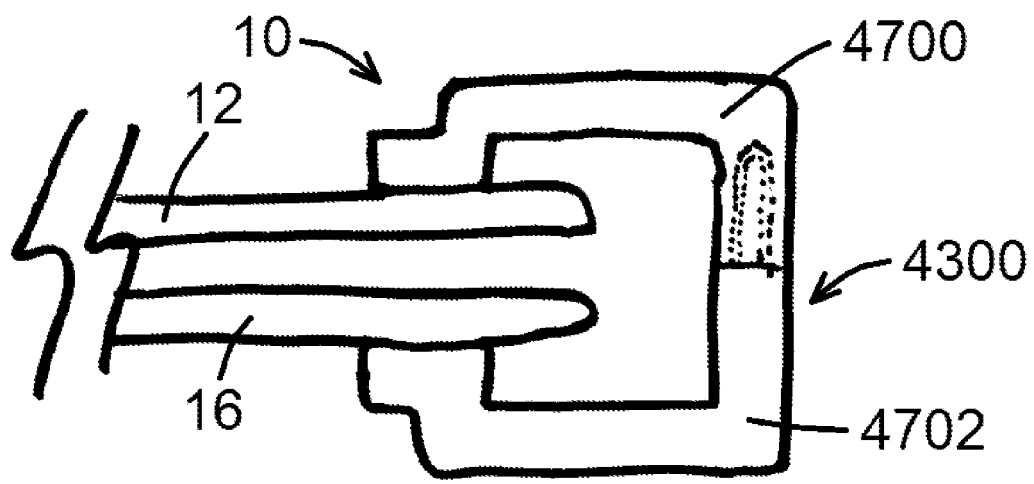
Figure 48B:
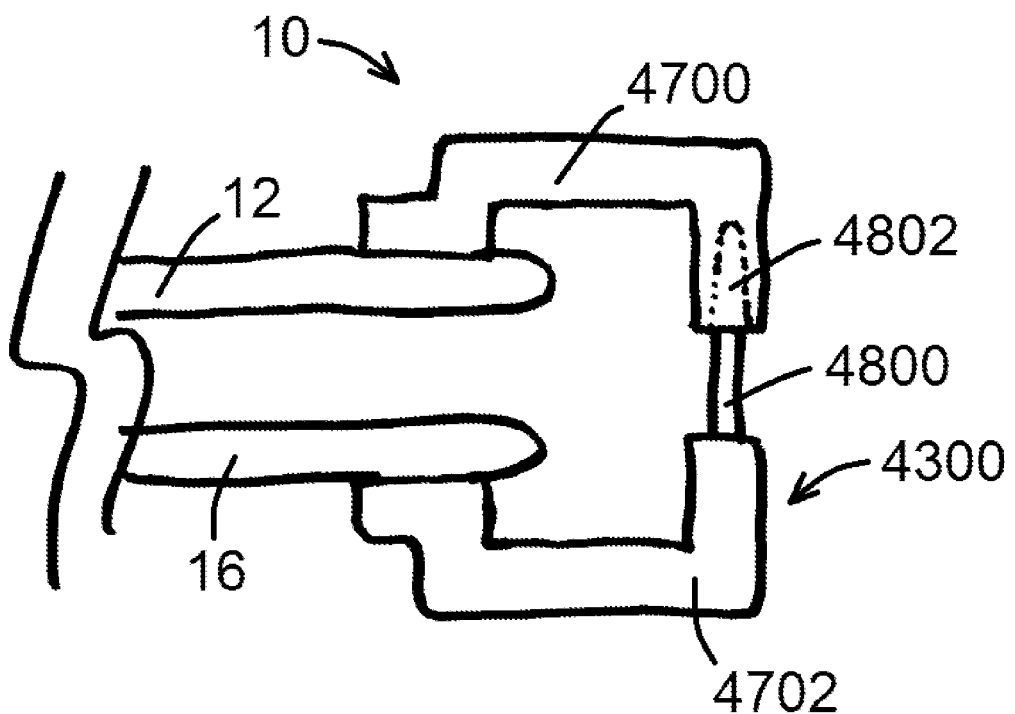

FIGS. 48A and B shows another embodiment of a portion of a device 10, whereby one or both c-rings 4300, 4400 (one shown, namely 4300 for example, in FIGS. 48A and 48B) are configured to expand from a relatively closed configuration (FIG. 48A), such as for delivery through a trocar, to a relatively open configuration (FIG. 48B), for placement about a stomach 100. In such an embodiment, the c-rings 4300, 4400 may have a first c-ring portion 4700 and a second c-ring portion, and one portion (such as, for example, second c-ring portion 4702 shown in FIG. 48B) may have a c-ring post 4800, and the other portion (such as, for example, first c-ring portion 4700 shown in FIG. 48B) may have a c-ring post aperture 4802 to receive the post 4800, allowing for such an expansion to occur.

Figure 49A:
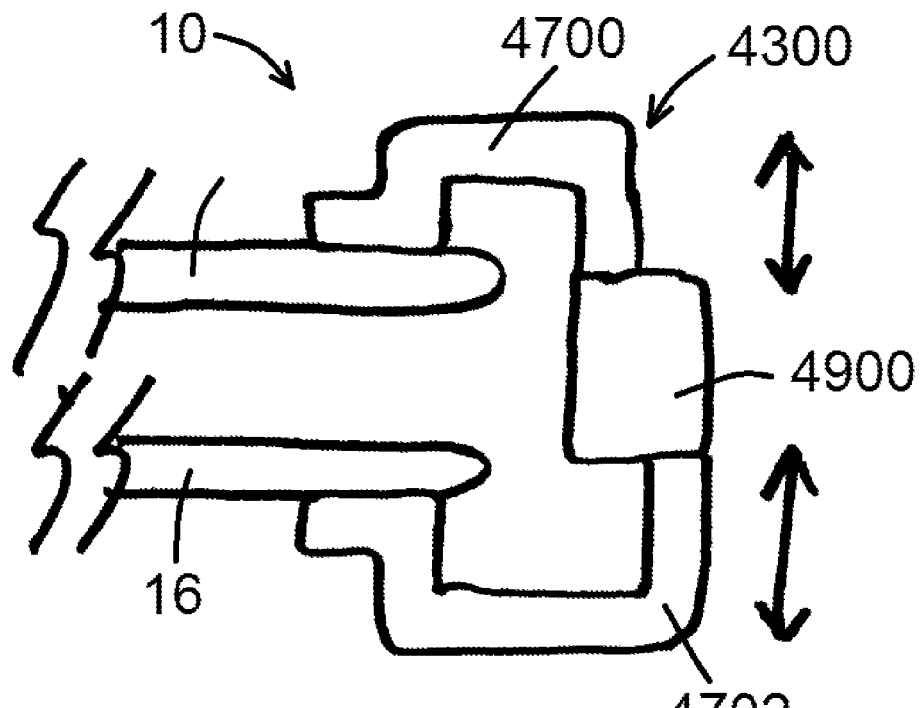
Figure 49B:
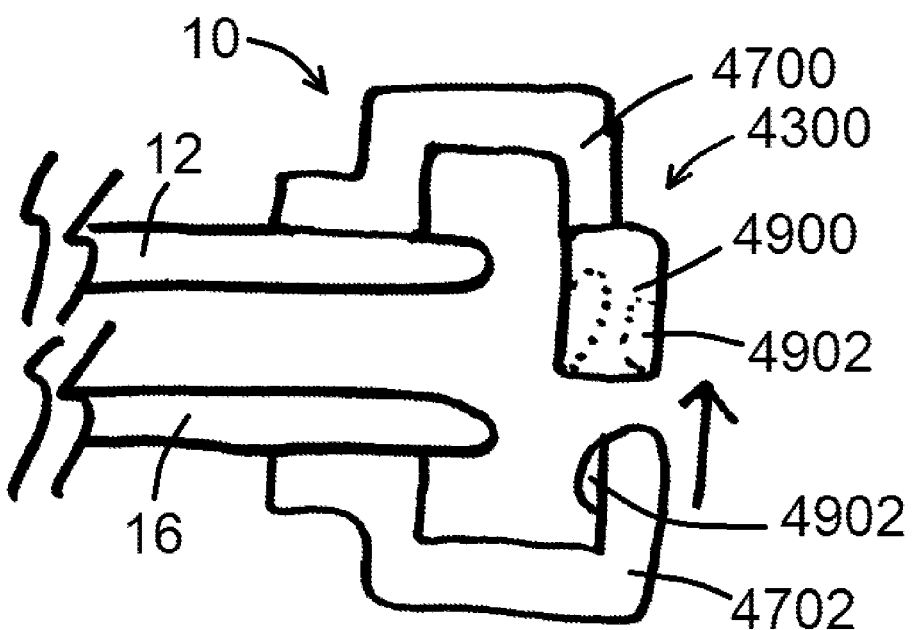

A slider coupler 4900, such as shown in FIGS. 49A and 49B, may also be used in connection with first and second c-ring portions. As shown in FIG. 49A, slider coupler 4900 is configured to receive, and slidingly engage, and retain (at least temporarily) at least one of the first ring portion 4700 and/or the second c-ring portion 4702, allowing one or both to move in the relative directions shown by the bold arrows in the figure. One or both c-ring portions (such as the second c-ring portion 4702 shown in FIG. 49B) can be separate from slider coupler 4900 and positioned therein after delivery through the trocar. An engagement mechanism 4902 within slider coupler 4902 or coupled to a c-ring 4300 can be used to maintain engagement of one or both c-rings 4300, 4400 within slider coupler 4900.

Figure 50B:
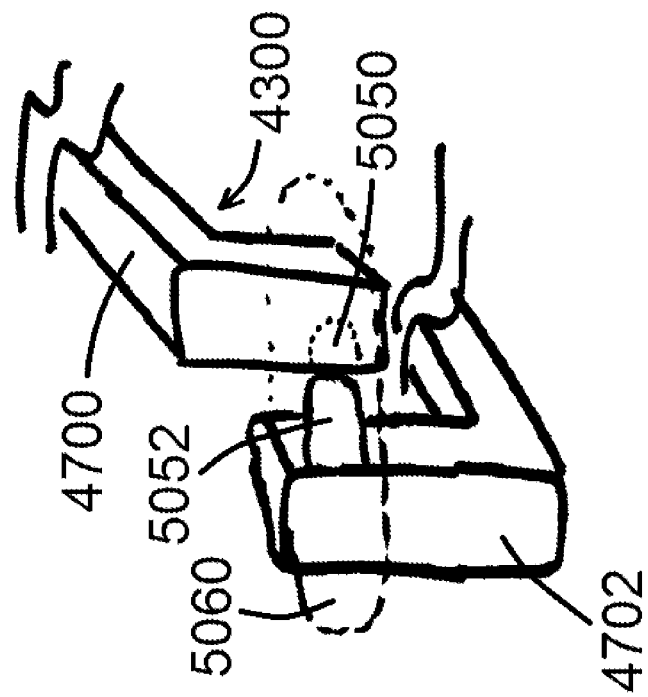
Figure 50A:
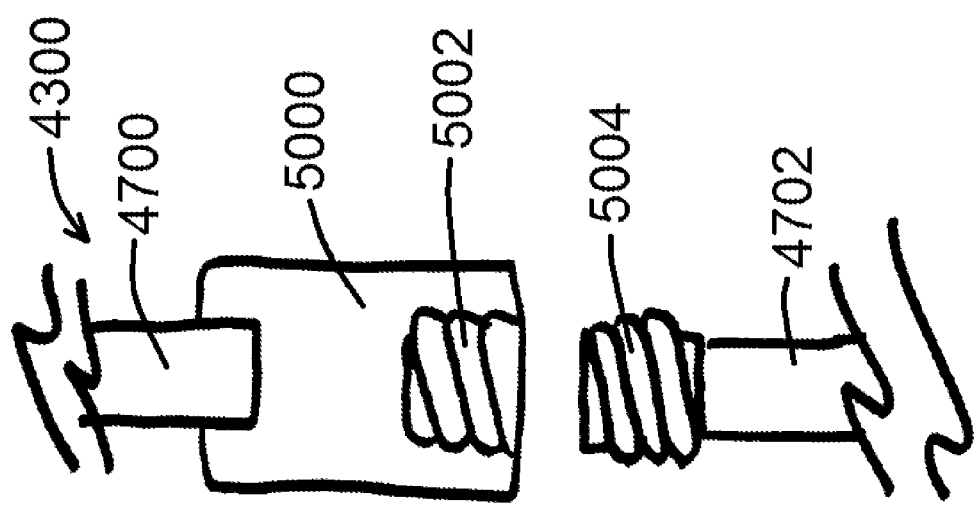

FIG. 50A shows yet another embodiment of portions of an exemplary c-ring 4300, 4400 (with first c-ring 4300 shown in the figure), whereby a first c-ring portion 4700 is coupled to, or forms a portion of, a joiner 5000, with said joiner 5000 defining an inner threaded portion 5002 therein. The inner threaded portion 5002 would be configured to receive an outer threaded portion 5004 of a second c-ring portion 4702, either by twisting the joiner 5000 or one of the c-rings 4300, 4400, or by pushing the c-rings 4300, 4400 toward one another. Another mechanism for coupling two c-ring portions 4300, 4400 to one another may be, as shown in FIG. 50B, by defining a c-ring stub aperture 5050 (which may also be referred to as a tab aperture) in one and having a c-ring stub 5052 (which may also be referred to as a tab) extending from another, the c-ring stub aperture 5050 configured to receive the c-ring stub 5052. Once coupled together, a cover 5060 (such as a tubing portion, for example) could be placed around the two c-ring portions 4300, 4400 to further hold the two portions 4300, 4400 together.

Figure 51A:
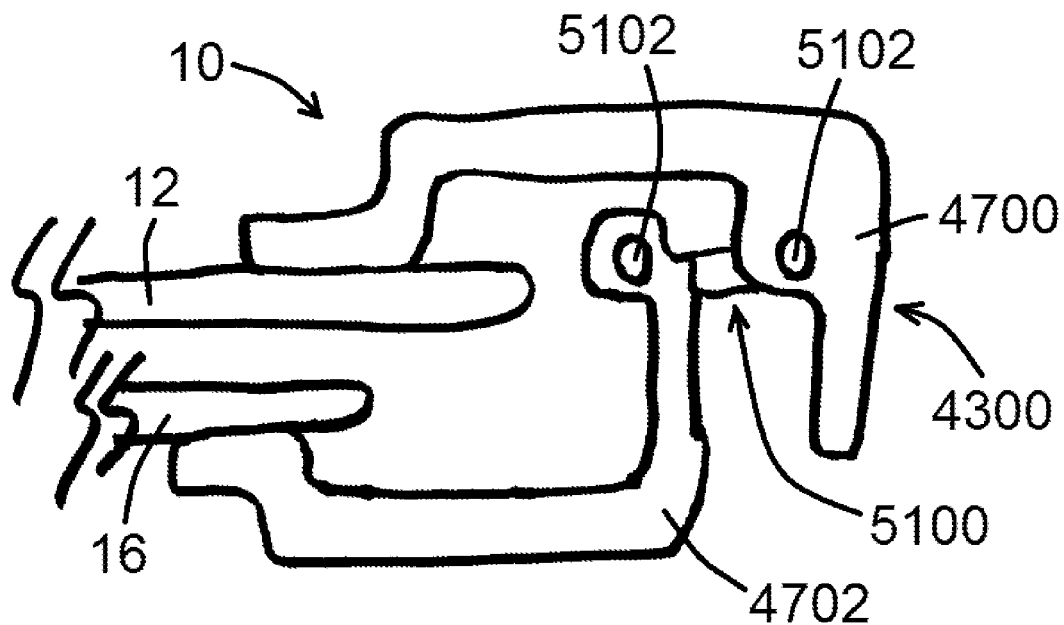
Figure 51B:
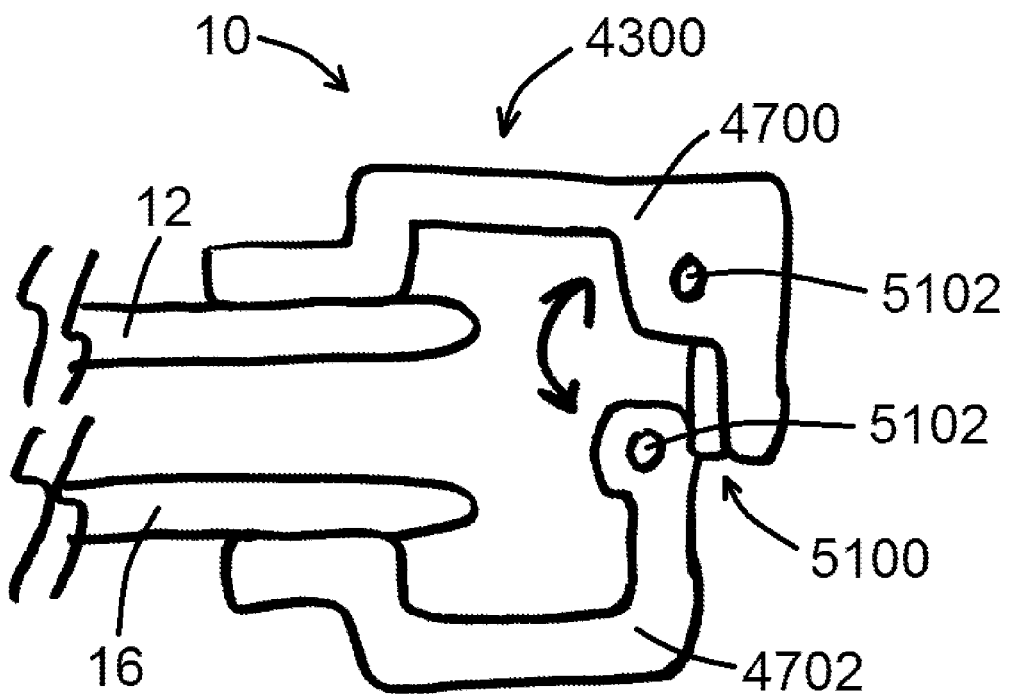
Figure 52A:
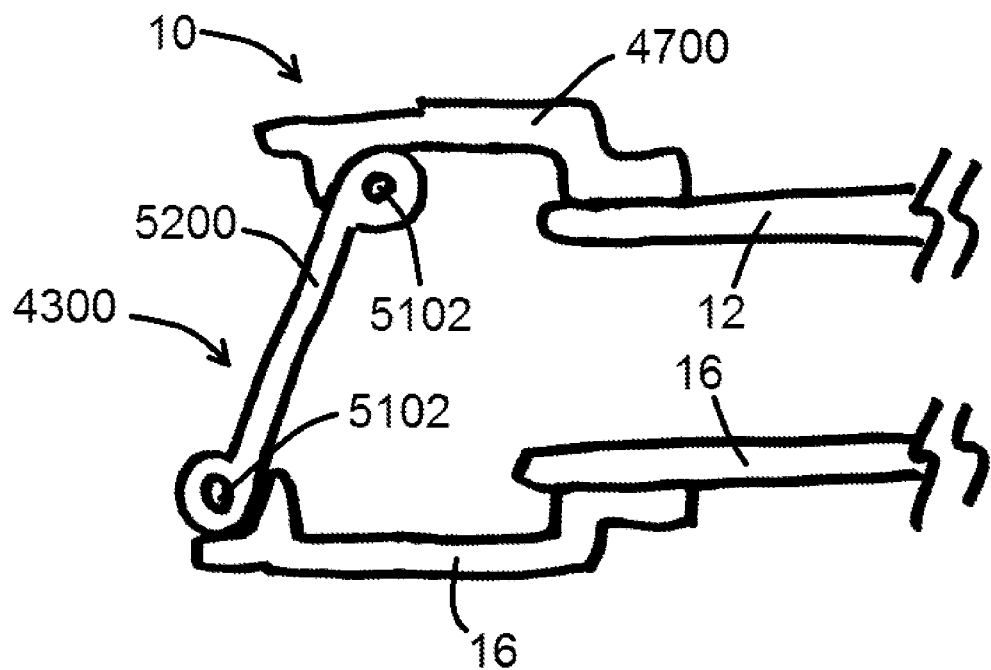
Figure 52B:
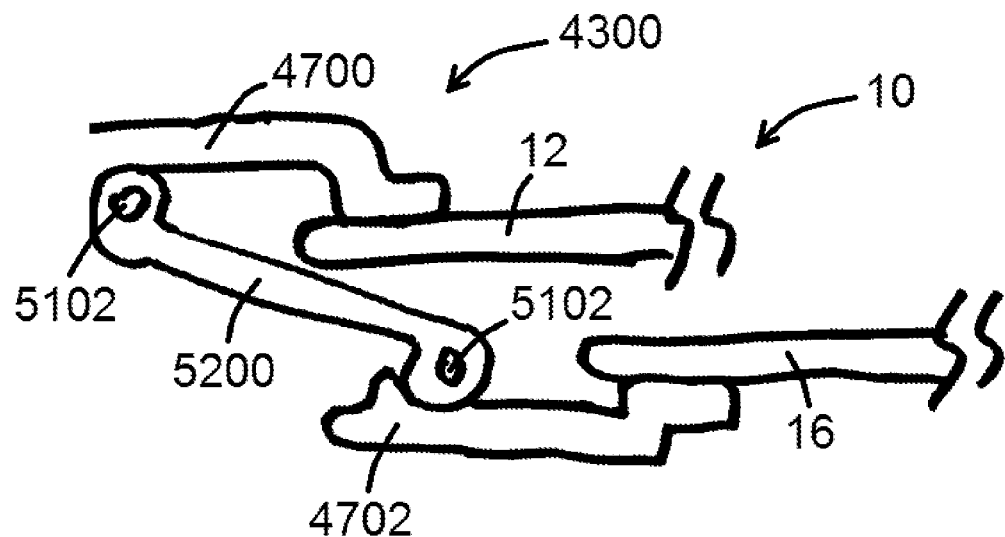

FIGS. 51A and 51B show c-ring portions 4700, 4702 having a two-part hinge 5100 therein, whereby pivot points 5102 defined therein allow one c-ring portion 4700 to pivot about a second c-ring portion 4702 at two locations, allowing a portion of device 10 to move from a relatively closed configuration (shown in FIG. 51A) to a relatively open configuration (shown in FIG. 51B), in a direction shown by the bold arrow in FIG. 51B. Another embodiment, shown in FIGS. 52A and 52B, show c-ring portions 4300, 4400 (with c-ring portion 4300 shown in the figures) connected to one another by way of a hinge unit 5200 configured to swivel about two pivot points 5102 so that the device 10 can move from a relatively open configuration (shown in FIG. 52A) to a relatively closed configuration (shown in FIG. 52B).

Figure 53A:
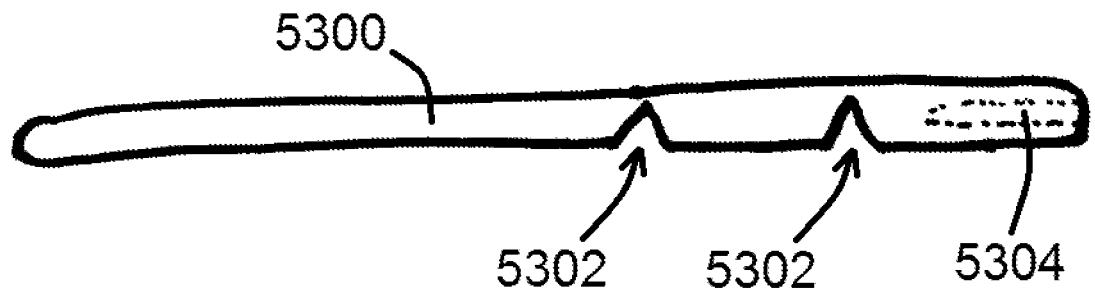
FIGS. 53A and 53B show a first elongated coupler and a first elongated coupler coupled to a second elongated coupler, respectively, according to exemplary embodiments of the present disclosure.
Figure 53B:
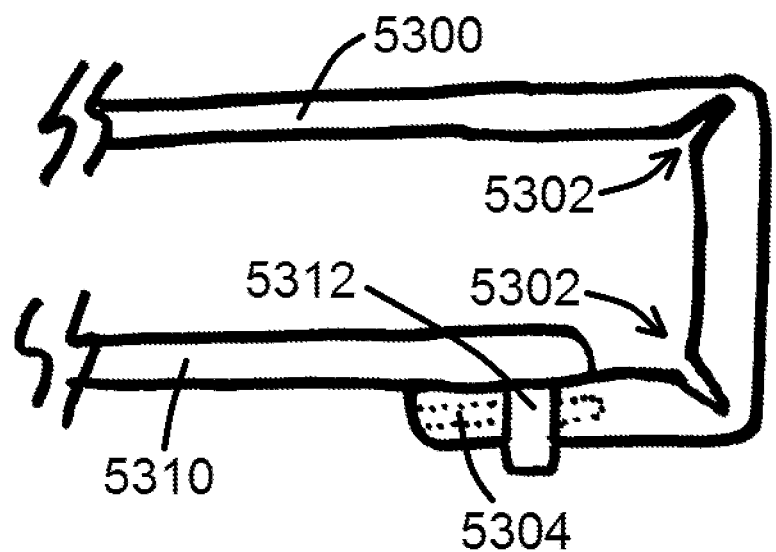

FIGS. 53A and 53B show an exemplary elongated coupler 5300 of the present disclosure with two living hinges 5302 defined therein. Living hinges 5302 allow the elongated coupler 5300 to flex in various ways, from a relatively straight configuration shown in FIG. 53A, to a relatively closed configuration in FIG. 53B, shown in FIG. 53B as coupled to a second elongated coupler 5310. A first coupler slot 5304 defined within the first elongated coupler 5300 can allow a portion of the second elongated coupler 5310 to pass therethrough, and a second coupler loop 5312 can be configured to receive a portion of the first elongated coupler 5300. Elongated couplers 5300, 5310, can connect to engaging components 12, 16.

The different configurations shown in FIGS. 47A-53B are intended, in various embodiments, to alter a cross-sectional size of the device 10 so that the relative cross-sectional size is smaller during delivery of the device 10 into a patient and larger when the device 10 is positioned around part of a stomach 100 or other bodily tissue.

Figure 54:
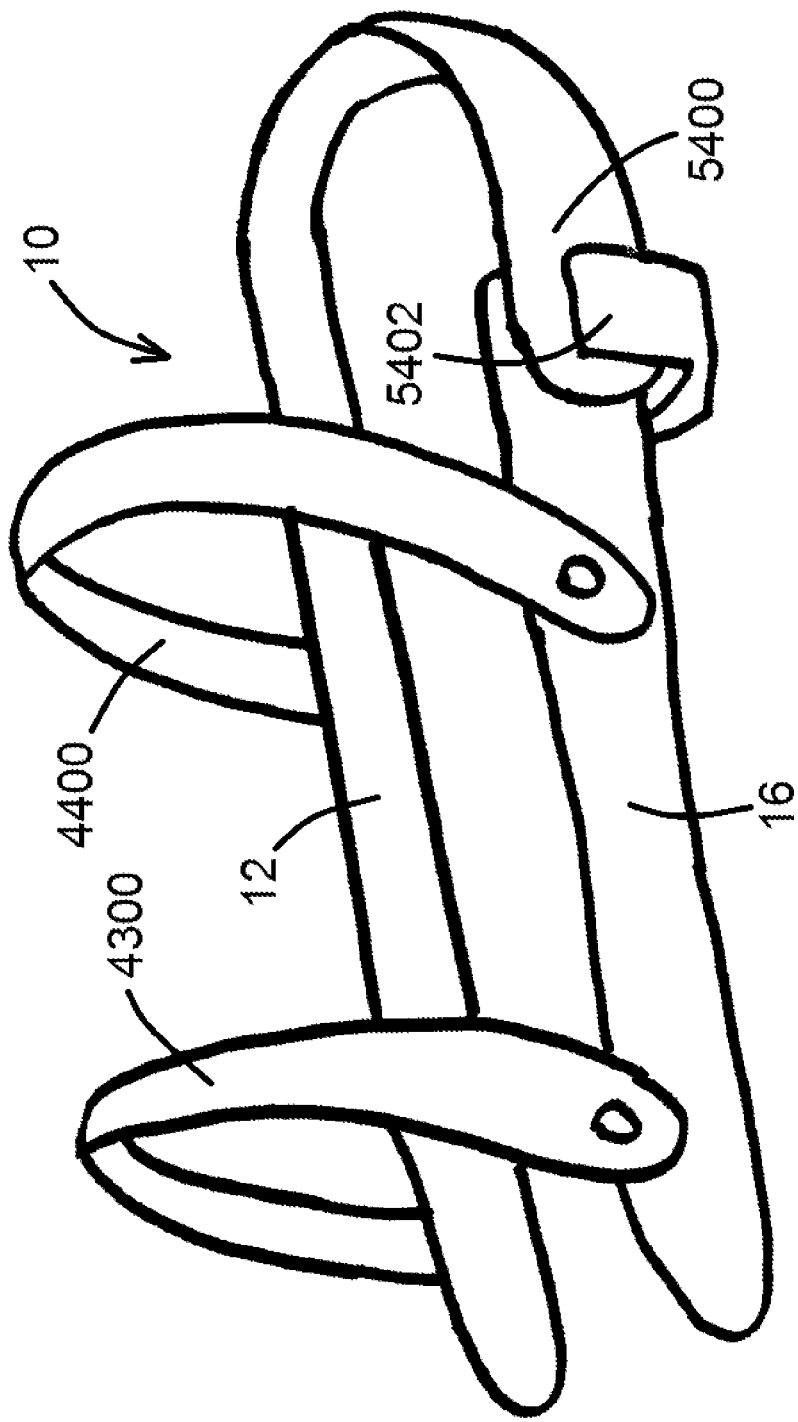
FIG. 54 shows a perspective view of a device, according to an exemplary embodiment of the present disclosure.

FIG. 54 shows yet another device 10 embodiment of the present disclosure, whereby the one of the engaging components 12, 16 (shown as first engaging component 12) loops around and couples to the other engaging component (shown as second engaging component 16). A component tab 5400 defined at one end of the first engaging component 12 may optionally engage a tab receiver 5402 of the second engaging component 16 to couple the two engaging components 12, 16 to one another.

Figure 55A:
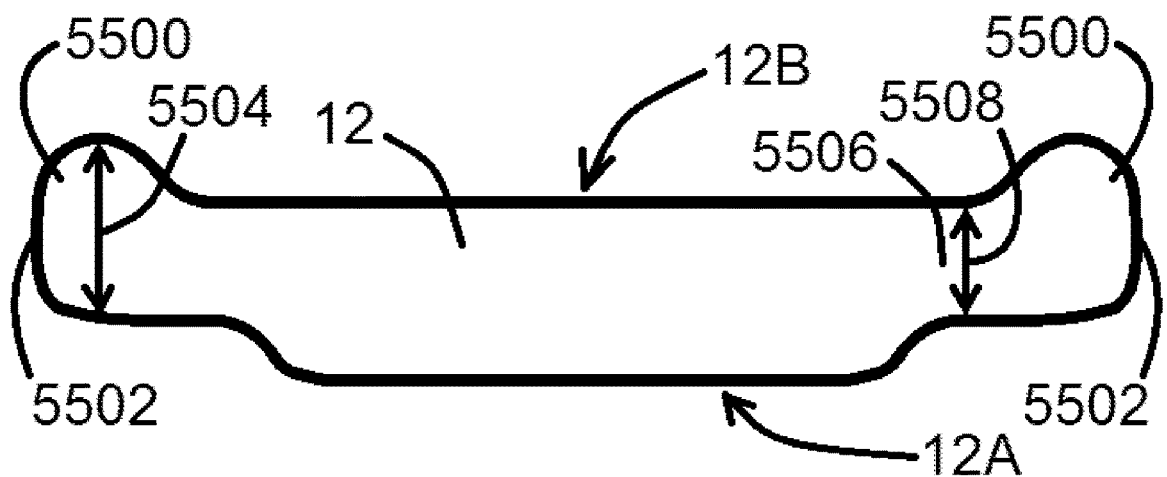
FIGS. 55A and 55B show cross-sectional views of exemplary engaging components, according to exemplary embodiments of the present disclosure.
Figure 55B:
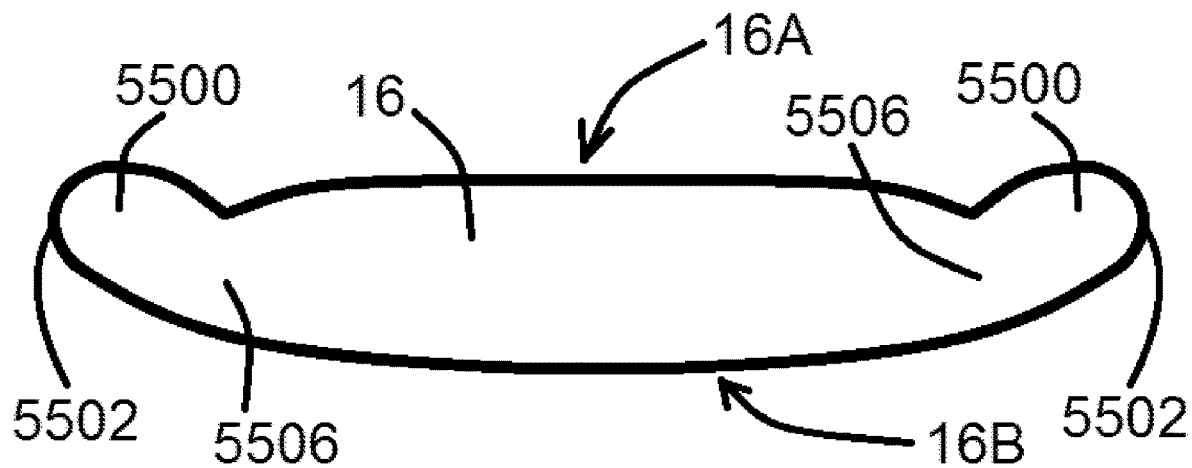

FIGS. 55A and 55B show cross-sectional end views of exemplary engaging components of the present disclosure.

FIG. 55A shows a cross-sectional end view of an exemplary engaging component 12, with first side 12A (the side that would contact a tissue, such as stomach 100) shown on the bottom and second side 12B (the side that would not contact a tissue) shown at the top. As shown therein, lobes 5500 of coating 4302 can be formed/present at the relative sides 5502 of engaging component 12, with lobes 5500 having a relatively larger cross-section 5504 than another portion of component 12, such as necks 5506 adjacent to lobes 5500, which have a relatively smaller cross-section 5508. Exemplary engaging components 12 of the present disclosure can also comprise a protrusion 5508, positioned at or near first side 12A, configured to provide additional potential comfort to a user of device 10. FIG. 55B shows a cross-sectional end view of an exemplary engaging component 16, with first side 16A (the side that would contact a tissue, such as stomach 100) shown on the bottom and second side 16B (the side that would not contact a tissue) shown at the top. As shown therein, lobes 5500 of coating 4302 can be also formed/present at the relative sides 5502 of engaging component 12 adjacent to necks 5506 as shown therein. Lobes 5500, as shown in FIG. 55B, may extend toward first side 16A, noting the difference between lobes 5500 shown in FIG. 55A, which extend away from first side 12A. Exemplary engaging components 16 of the present disclosure can also comprise a protrusion 5508, positioned at or near first side 16A, configured to provide additional potential comfort to a user of device 10.

Various c-rings, c-arms, couplers, and/or swivel arms described herein and/or shown in the figures may relate to the same type of componentry, so features described for one may apply to the others in various embodiments.

The various embodiments of restraining devices 10 described herein provide numerous benefits over the devices and systems of the prior art. An exemplary restraining device 10 may be inserted laparoscopically and/or endoscopically, is minimally invasive, completely reversible and available for chronic placement without the risk of complications. Furthermore, use of a restraining device 10 to treat and/or support a targeted tissue or organ produces a reduced amount of negative side effects than the procedures of the prior art for similar indications. While embodiments of restraining devices 10 are presented with respect to specific anatomy and treatment examples, the various restraining devices 10 and methods 300 may be expanded for use in treating any organ, limb or body structure that would benefit from reshaping, restoring, or added support provided through a reversible, easy to use and easy to implement technique for chronic placement.

Prior art focuses on creating a restrictive line through "clamps" to mimic the gastric sleeve. The disclosure of the present application provides various loosely-fitting restraints (to prevent migration) and to affect motility of the stomach 100. The contractility or motility curve of the gastric tissue is substantially attenuated by an external restraint (as discussed below), thus affecting the movement of bolus through the stomach 100. Hence, the food volume will remain in the pouch longer and lead to earlier distension which affects neuroactivity and mechanosensory elements of satiety. Hence, the principle of the restraining devices 10 of the present disclosure is based on flow (motility) unlike previous art that focuses on restrictive which risks migration and erosion.

As described herein, placement of exemplary restraining devices 10 through the lower curvature can be easily implemented as opposed to procedures which approach the greater curvature where the liver and diaphragm are in the proximity. Furthermore, various clips, clamps, or perforated plates known in the art which transverse the stomach 100 (as opposed to sleeve) can lead to substantial remodeling of the fundus which would lead to weight regain after a period of time. As such, the various connectors of the disclosure of the present application operate to prevent overall stretch of stomach 100 and hence prevent remodeling. The stretch that leads to mechanosensory satiety in the restraining devices 10 of the present disclosure occurs locally between the restraining springs or bars while still restraining the overall pouch. No such global containment of the gastric tissue is known in the prior art. Finally, various clips, clamps, or perforated plates known in the art would exert significant local stresses on the tissue which can lead to erosion or migration as the substantially restricted stomach 100 would attempt to distend. Conversely, the first engaging component 12 and the second engaging component 16 of the restraining devices 10 of the present disclosure distribute the stress more uniformly over the plate and only restrain a relatively small pouch rather than a more substantial portion of the stomach 100 transversely.

While various embodiments of implantable restraining devices, systems, and methods for using the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A device, comprising:
 a first engaging component comprising a first rigid inner plate at least partially surrounded by a first flexible coating;
 a second engaging component;
 a first c-ring coupled to the first engaging component at a first pivot point and coupled to the second engaging component at a second pivot point; and
 a cover flap coupled to either the first engaging component or the second engaging component, the cover flap capable of either further coupling to the second engaging component when initially coupled to the first engaging component or further coupling to the first engaging component when initially coupled to the second engaging component;
 wherein each of the first engaging component and the second engaging component define a longitudinal axis;
 wherein the device is further configured for placement around at least part of a stomach; and
 wherein the first c-ring is configured to swivel from a first position that is substantially coplanar with the longitudinal axis of the first engaging component and the longitudinal axis of the second engaging component to a second position that is substantially perpendicular with the longitudinal axis of the first engaging component and the longitudinal axis of the second engaging component.

2. The device of claim 1, wherein the second engaging component comprises a second rigid inner plate at least partially surrounded by a coating selected from the group consisting of the first flexible coating and the second flexible coating.

3. The device of claim 2, wherein the first flexible coating extends beyond a perimeter of the first rigid plate and wherein the second flexible coating extends beyond a perimeter of the second rigid plate.

4. The device of claim 3, wherein when the first flexible coating extends beyond a perimeter of the first rigid plate and when the second flexible coating extends beyond a perimeter of the second rigid plate, the first flexible coating and the second flexible coating prevents shearing and migration of the device when the first engaging component and the second engaging component contact the stomach.

5. The device of claim 2, wherein the cover flap comprises a first material surrounded at least substantially by a coating selected from the group consisting of the first flexible coating, the second flexible coating, and a third coating.

6. The device of claim 1, further comprising:
a second c-ring coupled to the first engaging component at a third pivot point and coupled to the second engaging component at a fourth pivot point.

7. The device of claim 6, wherein when the first c-ring and the second c-ring are not positioned within the interior space between the first engaging component and the second engaging component when in the second position when the device is open.

8. The device of claim 6, wherein at least one of the first c-ring and the second c-ring comprises at least one suture feature.

9. The device of claim 6, wherein at least one of the first c-ring and the second c-ring comprises a first c-ring portion and a second c-ring portion, and wherein the first c-ring portion and the second c-ring portion are configured to couple to one another by way of a mechanism selected from the group consisting of a coupler, a post, a slider coupler, a joiner, a c-ring stub, a hinge, and an elongated coupler.

10. The device of claim 6, wherein at least one of the first c-ring and the second c-ring comprises a metal insert at least substantially surrounded by a coating selected from the group consisting of the first flexible coating, the second flexible coating, and a third coating.

11. The device of claim 1, further comprising:
a first swivel stop positioned along at least one of the first engaging component and the second engaging component, the first swivel stop configured to limit swiveling of the first c-ring.

12. The device of claim 1, wherein at least one tab aperture is defined within the cover flap, wherein one of the first engaging component and the second engaging component further comprises a tab, and wherein the tab is configured for insertion into the tab aperture.

13. The device of claim 12, wherein one of the first engaging component and the second engaging component further comprises a loop coupled thereto, wherein at least a portion of the cover flap is configured to fit within the loop.

14. The device of claim 1, wherein one of the first engaging component and the second engaging component comprises a component tab configured to fit within a tab receiver of at the other of the first engaging component and the second engaging component.

15. An implantable device, comprising:
a first engaging component comprising a first rigid inner plate at least partially surrounded by a first flexible coating;
a second engaging component;
a first c-ring coupled to the first engaging component at a first pivot point and coupled to the second engaging component at a second pivot point; and
a cover flap coupled to either the first engaging component or the second engaging component, the cover flap capable of either further coupling to the second engaging component when initially coupled to the first engaging component or further coupling to the first engaging component when initially coupled to the second engaging component;
wherein each of the first engaging component and the second engaging component define a longitudinal axis;
wherein the device is further configured for placement around at least part of a stomach;
wherein the first c-ring is configured to swivel from a first position that is substantially coplanar with the longitudinal axis of the first engaging component and the longitudinal axis of the second engaging component to a second position that is substantially perpendicular with the longitudinal axis of the first engaging component and the longitudinal axis of the second engaging component;
wherein the first flexible coating extends beyond a perimeter of the first rigid plate and wherein the second flexible coating extends beyond a perimeter of the second rigid plate; and
wherein at least one tab aperture is defined within the cover flap, wherein one of the first engaging component and the second engaging component further comprises a tab, and wherein the tab is configured for insertion into the tab aperture.

16. A method for using an implantable device, the method comprising the steps of:
inserting an implantable device into a mammalian body, the implantable device comprising:
a first engaging component comprising a first rigid inner plate at least partially surrounded by a first flexible coating,
a second engaging component,
a first c-ring coupled to the first engaging component at a first pivot point and coupled to the second engaging component at a second pivot point, and
a cover flap coupled to either the first engaging component or the second engaging component, the cover flap capable of either further coupling to the second engaging component when initially coupled to the first engaging component or further coupling to the first engaging component when initially coupled to the second engaging component,
wherein each of the first engaging component and the second engaging component define a longitudinal axis,
wherein the device is further configured for placement around at least part of a stomach, and
wherein the first c-ring is configured to swivel from a first position that is substantially coplanar with the longitudinal axis of the first engaging component and the longitudinal axis of the second engaging component to a second position that is substantially perpendicular with the longitudinal axis of the first engaging component and the longitudinal axis of the second engaging component;

advancing the implantable device to a location within the mammalian body adjacent to a targeted tissue;

swiveling the first c-ring so that the first c-ring is substantially perpendicular to the first engaging component and the second engaging component; and positioning the first engaging component and the second engaging component over the targeted tissue such that at least a portion of the targeted tissue is positioned therebetween.

17. The method of claim 16, wherein when the targeted tissue expands in a direction between the first engaging component and the second engaging component, the targeted tissue exerts a force upon the first engaging component and the second engaging component.

18. The method of claim 16, wherein the step of positioning is performed to position the first engaging component and the second engaging component over at least part of the stomach.

19. The method of claim 18, wherein the method is performed to reduce a potential amount of food intake by reducing or eliminating an amount of food that can enter a fundus of the stomach.

20. The method of claim 18, further comprising the step of:

securing the cover flap over a fundus of the stomach so that the cover flap is secured to the first engaging component and the second engaging component.

* * * * *